United States Patent
Kent et al.

(10) Patent No.: US 11,197,854 B1
(45) Date of Patent: Dec. 14, 2021

(54) INHIBITORS FOR TARGETING FLAVIVIRUSES

(71) Applicant: National Technology & Engineering Solutions of Sandia, LLC, Albuquerque, NM (US)

(72) Inventors: Michael S. Kent, Albuquerque, NM (US); Susan Rempe, Albuquerque, NM (US); Juan M. Vanegas, Burlington, VT (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 246 days.

(21) Appl. No.: 16/684,445

(22) Filed: Nov. 14, 2019

Related U.S. Application Data

(60) Provisional application No. 62/767,323, filed on Nov. 14, 2018.

(51) Int. Cl.
| | |
|---|---|
| A61K 31/69 | (2006.01) |
| A61K 31/435 | (2006.01) |
| A61K 31/335 | (2006.01) |
| A61K 31/35 | (2006.01) |
| A61P 31/14 | (2006.01) |
| A61K 31/4745 | (2006.01) |
| G01N 33/68 | (2006.01) |
| A61K 45/06 | (2006.01) |
| A61K 31/351 | (2006.01) |
| A61K 31/366 | (2006.01) |
| A61K 31/7032 | (2006.01) |
| A61K 31/12 | (2006.01) |
| A61K 31/121 | (2006.01) |
| A61K 31/122 | (2006.01) |
| A61K 31/201 | (2006.01) |

(52) U.S. Cl.
CPC .......... *A61K 31/4745* (2013.01); *A61K 31/12* (2013.01); *A61K 31/121* (2013.01); *A61K 31/122* (2013.01); *A61K 31/201* (2013.01); *A61K 31/351* (2013.01); *A61K 31/366* (2013.01); *A61K 31/7032* (2013.01); *A61K 45/06* (2013.01); *A61P 31/14* (2018.01); *G01N 33/6893* (2013.01); *G01N 2800/26* (2013.01)

(58) Field of Classification Search
CPC .... A61K 31/69; A61K 31/435; A61K 31/335; A61P 31/14
USPC .................... 514/64, 292, 453, 460
See application file for complete search history.

(56) References Cited

U.S. PATENT DOCUMENTS

| | | | |
|---|---|---|---|
| 5,603,985 | A | 2/1997 | Kent et al. |
| 8,586,626 | B2 | 11/2013 | Powis |
| 9,242,210 | B1 | 1/2016 | Jiang et al. |
| 9,486,742 | B1 | 11/2016 | Rempe et al. |
| 10,130,916 | B1 | 11/2018 | Rempe et al. |
| 2014/0275234 | A1 | 9/2014 | Millard et al. |
| 2016/0213759 | A1 | 7/2016 | Rempe et al. |
| 2017/0207485 | A1 | 7/2017 | Fenton et al. |
| 2019/0002490 | A1 | 1/2019 | Kent |

FOREIGN PATENT DOCUMENTS

| | | |
|---|---|---|
| WO | WO 2003/024183 | 3/2003 |
| WO | WO 2015/038639 | 3/2015 |

OTHER PUBLICATIONS

Acosta EG et al., "Cell entry of dengue virus," *Futur. Virol.* 2008:3:471-479.
Akçay G et al., "Inhibition of Mcl-1 through covalent modificatios of a noncatalytic lysine side chain," *Nat. Chem. Biol.* 2016;12:931-936.
Allison SL et al., "Mutational evidence for an internal fusion peptide in flavivirus envelope protein E," *J. Virol* 2001;75:4268-4275.
An

(56) References Cited

OTHER PUBLICATIONS

Berendsen HJC et al., "The missing term in effective pair potentials," *J. Phys. Chem.* 1987;91:6269-6271.

Budvytyte R et al., "Structure and properties of tethered bilayer lipid membranes with unsaturated anchor molecules," *Langmuir* 2013;29:8645-8656.

Cal PMSD et al., "Iminoboronates: a newstratecy for reversible protein modificaton," *J. Am. Chem. Sec.* 2012;134:10299-10305.

Cheeseman MD et al., "Exploiting protein conformational change to optimize adenosine-derived inhibitors of HSP70," *J. Med. Chem.* 2016;59:4625-4636.

Chernomordik L et al. "Protein-lipid interplay in fusion and fission of biological membranes," *Annu. Rev. Biochem.* 2003;72:175-207.

Chernomordik L et al., "The hemifusion intermediate and its conversion to complete fusion: regulation by membrane composition," *Biophys. J.* 1995;69:922-929.

Chernomordik LV et al., "The pathway of membrane fusion catalyzed by influenza hemagglutinin: restriction of lipids, hemifusion, and lipidic fusion pore formation," *J. Cell. Biol.* 1998:140:1369-1382.

Chiu SW et al., "An improved united atom force field for simulation of mixed lipid bayers," *J. Phys. Chem. B* 2009;113:2748-2763.

Choi S et al., "Chemoselective Small molecules that covalently modify one Lys in a non-enzyme protein in plasma," *Nat. Chem. Biol.* 2010;6:133-139.

Christian EA et al., "Atomic-level functional model of dengue virus envelope protein infectivity." *Proc. Natl. Acad. Sci. USA* 2013;110:18662-18667.

Corvet J et al., "Membrane fusion activity of tick-bome encephalitis virus and recombinant subviral particles in a liposcmal model system," *Virology* 2000;269:37-46.

Davies TG et al., "Stucture-based design of a potent purine-based cyclin-dependent kinase inhibitor," *Nature Struct. Biol.* 2002;9:745-749.

Deng J et al., "Discovery of novel small molecule inhibitors of Dengue viral NS25-NS3 protease using virtual screening end scaffold hopping," *J. Med Chem.* 2012;55:6278-6293.

Deng YO et al., "A broadly flavivirus cross-neutralizing monoclonal antibody that recognizes a novel epitope within the fusion loop of E protein," *PloS ONE* 2011;6:e16059 (8 pp.).

Epand RM, "Fusion peptides and the mechanism of viral fusion," *Biochim. Biophys. Acta* 2003;1614:116-121.

Everts M et al., "Accelerating drug development: antiviral therapies for emerging viruses as a model," *Annu. Rev. Pharmacol. Toxicol.* 2017;57:155-169.

Green N et al., "Cell-based assays to identity inhibitors of viral disease," *Expert Opin Drug Discov.* 2008;3:671-676.

Gollins SW et al., "pH-dependent fusion between the flavivirus West Nile and liposomal model membranes."*J. Gen. Virol.* 1986;67:157-166.

Gushwa NN et al., "Selective targetng of distinct active site nucleophiles by irreversible Src-family kinase inhibitors," *J. Am. Chem. Soc.* 2012;134:20214-20217.

Hacker SM et al., "Global profiling of lysine reactivity and ligandability in the human proteome," *Nat Chem.* 2017;9:1181-1190.

Hed G et al., "Initiation and dynamics of hemifusion in lipid bilayers," *Biophys. J.* 2003;85:381-389.

Heinrich F et al., "Myristoylation restricts orientation of the GRASP domain on membranes and promotes membrane tethering," *J. Biol. Chem.* 2014;289:9683-9691.

Hoppmann C et al., "Proximity-enabled bioreactivity to generate covalent peptide inhibitors of p53-Mdm4," *Chem Commun.* 2016;52:5140-5143.

Huang CYH et al., "The dengue virus type 2 envelope protein fusion peptide is essential for membrane fusion," *Virology* 2010;396:305-315.

Hung WC et al. "The condensing effect of cholesterol in lipid layers," *Biophys. J.* 2007;92:3980-3967.

Johnson SM et al., "Toward optimization of the linker substructure common to transthyretin amyloidogenesis inhibitors using biochemical and structural studies," *J. Med. Chem.* 2008;51:6348-6358.

Harrison SC, "Viral membrane fusion," *Nat. Struct. Mol Biol.* 2008;15:690-698.

Heinrich F et al., "A new lipid anchor for sparsely tethered bilayer lipid membranes," *Langmuir* 2009;25:4219-4229.

Heinrich F et al., "Zooming in on disordered systems: neutron reflection studies of proteins associated with fluid membranes," *Biochim. Biophys. Acta* 2014;1838:2341-2349.

Kent MS et al., "Study of insertion of Dengue E into lipid bilayers by neutron reflectvity and molecular dynamics simulatons," Sandla Report No. SAND2017-4932C, 25 pp.

Kiellan M. "Class II virus membrane fusion proteins," *Virology* 2006;344:38-47.

Kiellan M et al., "Virus membrane-fusion proteins: more than one way to make a hairpin," *Nat. Rev. Microbiol.* 2005:4:67-76.

Kikhney AG et al., "A practical guide to small angle X-ray scattering (SAXS) of flexible and intrinsically disordered proteins," *FEBS Lett.* 2015;589:2570-2577.

Kirby BJ et al., "Phase-sensitive specular neutron reflectometry for imaging the nanometer scale composition depth profile of thin-film materials," *Curr. Opin. Colloid Interface Sci.* 2012;17:44-53.

Klein DE et al., "Structure of a dengue virus envelop protein late-staqe fusion intermediate," *J. Virol* 2013;87:2287-2293.

La Bauve E et al., "Method for measuring ths unbinding energy of strongly-bound membrane-associated proteins," *Biochim. Biophys Acta* 2016:1858:2753-2762.

Larsson P et al., "Lipid tall protrusion in simulations predicts fusogenic activity of influenza fusion peptide mutants and conformational models," *PLoS Comput. Biol.* 2013:9:e1002950 (9 pp.).

Leyssen P et al., "Perspectives for the treatment of infections with Flaviviridae," *Clin. Microbiol. Rev.* 2000;13:67-82.

Li L et al., "Structure-guided discovery of a novel non-peptide inhibitor of Dengue virus NS2B-NS3 protease," *Chem. Biol. Drug Des.* 2015;86:255-264.

Liao M et al., "In vitro reconstition reveals key intermediate states of timer formation by the dengue virus membrane fusion protein," *J. Virol*, 2010;84:5730-5740.

Lomize Al et al., "The role of hydrophobic interactions in positioning of peripheral proteins in membranes," *BMS Struct. Biol.* 2007;7:44 (30 pp.).

Longo ML et al., "Interaction of the influenza hemagglutinin fusion peptide with lipid bilayers: area expansion and permeation," *Biophys. J.* 1997;73:1430-1439.

Lonsdale R et al., "Structure-based design of targeted covalent inhibitors," *Chem. Soc. Rev.* 2018;47:3816-3830.

Luca VC st al., "Stucture of the St. Louis encephalitis virus postfusion envelope trimer." *J. Virol.* 2013;87:818-828.

McGillivray DJ et al., "Structure and functional *Staphylococcus aureus* alpha-hemolysin channels in tethered bilayer lipid membranes," *Biophys. J.* 2009;96:1547-1553.

Melikyan GB et al., "inner but not outer membrane leaflets control the transition from glycosylphosphatidylinositol-anchored influenza hemagglutinin-induced hemifusion to full fusion," *J. Cell. Biol.* 1997;136:995-1005.

Melo MN et al., "Interaction of the dengue virus fusion peptide with membranes assessed by NMR: the essential role of the envelope protein Trp101 for membrane fusion." *J. Mol. Biol.* 2009:392:736-746.

Mirjanian D et al., "Splaying gf allphatic tails plays a central role in barrier crossing during Tiposome fusion," *J. Phys. Chem. B* 2010;114:11061-11068.

Modis Y et al., "Structure of the dengue virus envelope protein after membrane fusion," *Nature* 2004;427:313-319.

Morgan HP et al., "A new family of covalent inhibitors block nucleotide binding to the active site of pyruvate kinase." *Biochem. J.* 2012;448:67-72.

Narayanan A et al., "Sulfonyl fluorides as privileged warheads in chemical biology." *Chem Sci.* 2015;6:2650-2659.

(56) References Cited

OTHER PUBLICATIONS

Olsson MHM et al., "PROPK3: consistent treatment of internal and surface residues in empirical pKa predictions," *Chem. Theory Comput.* 2011;7:525-537.

Pal PK et al., "Affinity labeling of the inhibitory DPNH site of bovine ver glutamate dehydrogenase by 5'-fluorosulfonyl benzoyl adenosine." *J. Biol. Chem.* 1975;250:8140-8147.

Pan J et al., "Synthetic fusion peptides of tick-bome encephalitis virus as models for membrane fusion," *Biochemist* 2010;49:287-296.

Peitzsch RM st al., "Binding of acylated peptides and fatty acids to phospholipid vesicles: pertinence to mryistoylated proteins," *Biochemistry* 1993;32:10436-10443.

Penfold J et al., "The application of the specular relection of neutrons to the study of surfaces and interfaces," *J. Phys. Condens. Matter* 1990;2:369-1412.

Pettinger J et al., "An irreversible inhibitor of HSP72 that unexpectedly tablets lysine-56," *Angew. Chem, Int. Ed.* 2017;56(13)3536-3540.

Pettinger J et al., "Lysine-targeting covalent inhibitors," *Angew. Chem. Int. Ed.* 2017;26:115200-15209.

Pronk S et al., "GROMACS 4.5: a high-throughput and highly parallel open source molecular simulation toolkit" *Bioinformatics* 2013;29:845-854.

Raul R et al., "A small molecule inhibitor of dengue virus type 2 protease inhibits the replication of all four dengue virus serotypes in cell culture," *Virol. J.* 2015;12:16 (7 pp.).

Resh MD, "Trafficking and signaling by fatty-acylated and prenlated proteins." *Nat. Chem. Biol.* 2006;2:584-590.

Rodenhuis-Zybert IA et al., "Dengue virus life cycle: viral and host factors modulating infectivity," *Cell. Mol. Life Sci.* 2010;67:2773-2786.

Rogers DM et al., "Molecular basis of endesomal-membrane association for the dengue virus envelope protein," *Biochim Biophys Acta* 2015;1848:1041-1052.

Sanchez-San Martin C et al., "Dealing with low pH: entry and exit of alphaviruses and flaviviruses," *Trends Microbiol.* 2009;17:514-521.

Schmid N et al., "Definition and testing of the GROMOS force-field versions 54A7 and 54B7," *Eur Biophys. J.* 2011;40:843-856.

Seligman SJ, "Constancy and diversity in the flavivirus fusion peptide," *Virol J.* 2008;5:27 (10 pp.).

Shannon DA et al., "Investigating the proteome reactivity and selectivity of aryl halides," *J. Am. Chem. Soc.* 2014;136:3330-3333.

Shekhar P et al., "Continuous distribution model for the investigation of complex molecular architectures near interfaces with scattering techniques," *J. Appl. Phys.* 2011;110:102216 (12 pp.).

Stauffer F et al., "Interaction between dengue virus fusion peptide and lipid bilayers depends on peptide clustering," *Mol. Membr. Biol.* 2008;25:128-138.

Stiasny K et al., "Involvement of lipids in different steps of the flavivirus fusion mechanism," *J. Virol* 2003;77:7856-7862.

Takahashi K, "The reaction of phenylglyoxal with arginine residues in proteins." *J. Biol. Chem.* 1968;243:6171-6179.

Tanaka K et al., "Synthesis of a new phospholipase $A_2$ Inhibitor of an aldehyde terpenoid and its possible inhibitory mechanism," *Tetrahedron Lett.* 1998;39:1185-1188.

Tanaka K et al., "The inhibitory mechanism of bovine pancreatic phospholipase $A_2$ by aldehyde terpenoids," *Tetrahedron* 1999;55:1657-1686.

Tian YS et al., "Denaue virus and its inhibltors: a brief review." *Chem Pharm. Bull.* 2018;66:191-206.

Toi K et al., "Studies on the chemical modification of arginine 1. The reaction of 1,2-cyclohexanedione with arginine and arginyl residues of proteins," *J. Biol. Chem.* 1967;242:1036-1043.

Umashankar M et al., "Differential cholesterol binding by class II fusion proteins determines membrane fusion properties," *J. Virol.* 2008,82;9245-9253.

Vanegas JM et al., "Insertion of Dengue E into lipid bilayers studied by neutron reflectivity and molecular dynamics simulations," *BBA Biomembranes* 2018;1860:1216-1230.

Vanegas JM et al., Supporting Information for "Insertion of Dengue E into lipid bilayers studied by neutron reflectivity and molecular dynamics simulations," *BBA Biomembranes* 2018;1860:1216-1230 (14 pp.).

Volz TJ et al., "Covalent and nonovalent chemical modifications of arginine residues decrease dopamine transporter activity," *Synapse* 2004;52:272-282.

Weigel LF et al., "Phenylalanine and phenylgtycine analogues as arginine mimetics in Dengue protease inhibitors," *J. Med. Chem.* 2015;58:7719-7733.

Wu H et al, "Novel Dengue virus NS2B/NS3 protease inhibitors," *Antimicrob Agents Chemother.* 2015;59:1100-1109.

Yalovsky S et al., "Lipid modifications of proteins—slipping in and cut of membranes." *Trends Plant Sci.* 1999;4:439-445.

Yamada M et al., "Discovery of novel and potent small-molecule inhibitors of NO and cytokine production as antisepsis agenis: synthesis and biological activity of alkyl 6-(N-substituted sulfamoyl)cyclohex-1-ene-1-carboxylate," *J. Med. Chem.* 2005;48:7457-7467.

Zaitseva E et al., "Class II fusion protein of alphaviruses drives membrane fusion through the same pathway as class I proteins," *J. Cell. Biol.* 2005;169:167-177.

Zaitseva E et al., "Dengue virus ensures its fusion in late endosomes using compartment-specific lipids," *PLoS Pathogens* 2010;6:e1001131 (14 pp.).

Zhao Q et al., "Broad-spectrum kinase profiling in live cells with lysine-targeted sulfonyl fluoride probes," *J. Am. Chem. Soc.* 2017;139:680-685.

Zheng A et al., "In vitro and in vivo studies identify Important features of dengue virus pr-E protein interactions," *PLoS Pathogens* 2010;6:e1001157 (12 pp).

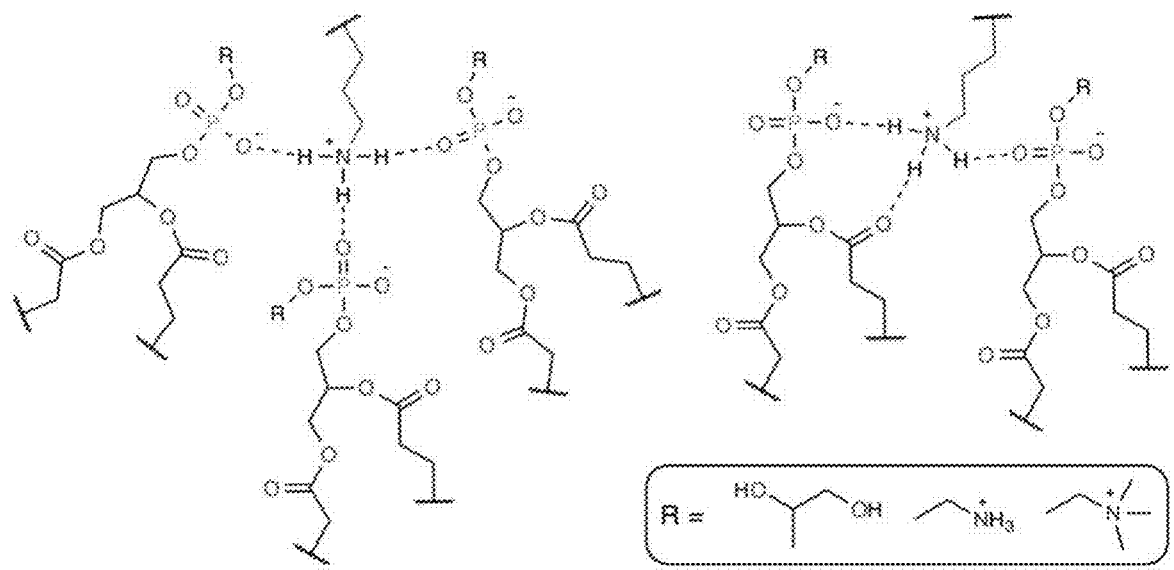
FIG. 3C
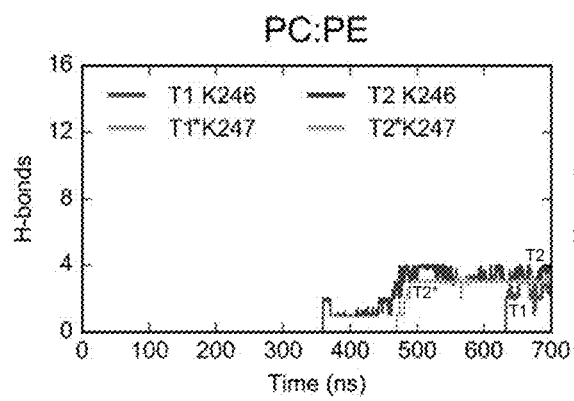
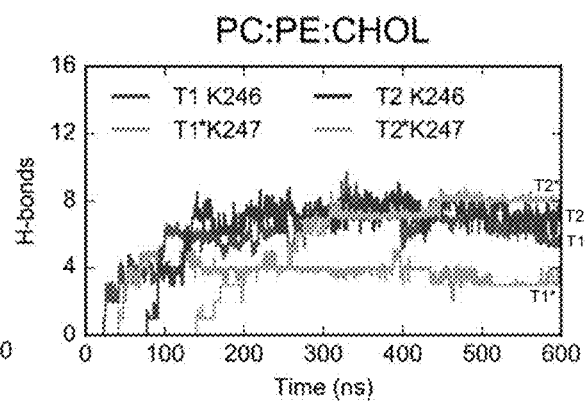
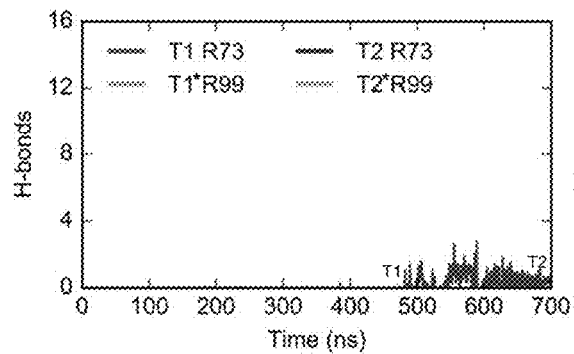
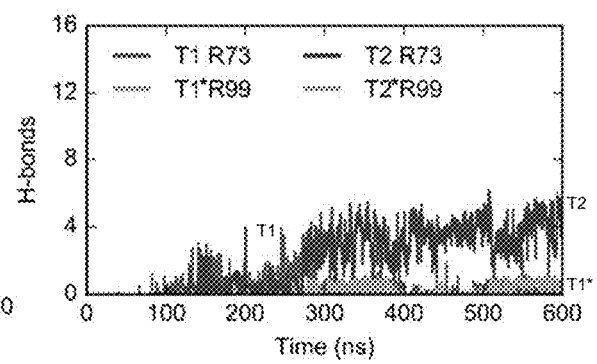
FIG. 3D
FIG. 3E

| | 70　　　　80　　　　90　　　　100<br>｜　　　　｜　　　　｜　　　　｜<br>-a->　　　　　　　　　-----c---> | SEQ ID NO: | 240　　　　250<br>｜　　　　｜<br>-i>　　　　-j> | SEQ ID NO: |
|---|---|---|---|---|
| DENV 1 | TDSRCPTQGEATLVEEQDANFVCRRTFVDRG | 1 | VTFKTAHAKKQEVVVLGSQ | 2 |
| DENV 2 | TDSRCPTQGEPSLNEEQDKRFVCKHSMVDRG | 3 | VTFKNPHAKKQDVVVLGSQ | 4 |
| DENV 3 | TDSRCPTQGEAVLPEEQDQNYVCKHTYVDRG | 5 | VTFKNAHAKKQEVVVLGSQ | 6 |
| DENV 4 | TATRCPTQGEPYLKEEQDQQYICRRDVVDRG | 7 | VTFKVPHAKRQDVTVLGSQ | 8 |
| Powassan | VEARCPTTGPATLPEEHQANMVCKRDQSDRG | 9 | VEFGPPHAVKMDIFNLGDQ | 10 |
| Culex | STDVCPGGSQLNMGEINGKERVCSTQPYNRG | 11 | VVWGDARANEVLVKNILEP | 12 |
| Kyasanur | VVARCPAMGPATLPEEHQASTVCRRDQSDRG | 13 | VEFGEPHAVKMDIYNLGDQ | 14 |
| YFV | INDRCPSTGEAHLVEENEGDNACKRTYSDRG | 15 | VEFPPHAATIRBLALGNQ | 16 |
| TBEV | VAARCPTMGPATLAEEHQSGTVCKRDQSDRG | 17 | VEFGAPHAVKMDVYNLGDQ | 18 |
| SLEV | TVARCPTTGEAHNTKRSDPTFVCKRDVVDRG | 19 | VEFEEPHATKQTVVALGSQ | 20 |
| WNV 2 | TKAACPTMGEAHNEKRADPAFVCKQGVVDRG | 21 | MEFEEPHATKQSVVALGSQ | 22 |
| WNV 1b | TKAACPTMGEAHNDKRADPSFVCKQGVVDRG | 23 | MEFEEPHATKQSIVALGSQ | 24 |
| Chaoyang | VESGCPGTDEIHNTKAKDTSYMCKVSYPDRG | 25 | VEFGVPHATRQSVYSIGDQ | 26 |
| Usutu | TVSNCPTTGEAHNPKRAEDTYVCKSGVTDRG | 27 | LEFEEPHATKQSVVALGSQ | 28 |
| Donggang | SVNGCPSTTEAHNDRKKDSTYLCERSYPDRG | 29 | VEFSTPHATKQSVYTLGDQ | 30 |
| JEV | TVARCPTTGEAHNEKRADSSYVCKQGFTDRG | 31 | MEFEEAHATKQSVVALGSQ | 32 |
| ZIKV | SDSRCPTQGEAYLDKQSDTQYVCKRTLVDRG | 33 | VEFKDAHAKRQTVVVLGSQ | 34 |

DENV: Dengue virus
YFV: yellow fever virus
TBEV: tick-borne encephalitis virus
SLEV: St. Louis encephalitis virus
WNV: West Nile virus
JEV: Japanese encephalitis
ZIKV: Zika virus

FIG. 5

| UniProtKB Acc. No. | Sequence | Position | SEQ ID NO: |
|---|---|---|---|
| P27909\|POLG_DEN1B | TDSRCPTQGEATLVEEQDANFVCRRTFVDRG | 350-380 | 35 |
| P27913\|POLG_DEN1C | TDSRCPTQGEATLVEEQDANFVCRRTFVDRG | 350-380 | 36 |
| P17763\|POLG_DEN1W | TDSRCPTQGEATLVEEQDTNFVCRRTFVDRG | 350-380 | 37 |
| P33478\|POLG_DEN1S | TDSRCPTQGEATLVEEQDANFVCRRTFVDRG | 350-380 | 38 |
| P27912\|POLG_DEN1A | TDSRCPTQGEATLVEEQDTNFVCRRTFVDRG | 350-380 | 39 |
| P14338\|POLG_DEN22 | TESRCPTQGEPSLNEEQDKRFVCKHSMVDRG | 70-100 | 40 |
| P14339\|POLG_DEN23 | TESRCPTLGEPSLNEEQDKRLVCKHSMVDRG | 70-100 | 41 |
| P14337\|POLG_DEN28 | TESRCPTQGEPSLNEEQDKRFVCKHSMVDRG | 350-380 | 42 |
| P29991\|POLG_DEN27 | TESRCPTQGEPSLNEEQDKRFVCKHSMVDRG | 350-380 | 43 |
| P30026\|POLG_DEN2D | TESRCPTQGEPSLNEEQDKRFVCKHSMVDRG | 350-380 | 44 |
| P07564\|POLG_DEN2J | TESRCPTQGEPSLNEEQDKRFLCKHSMVDRG | 350-380 | 45 |
| Q9WDA6\|POLG_DEN2Q | TDSRCPTQGEPTLNEEQDKRFVCKHSMVDRG | 350-380 | 46 |
| P12823\|POLG_DEN2P | TDSRCPTQGEPTLNEEQDKRFVCKHSMVDRG | 350-380 | 47 |
| P29990\|POLG_DEN26 | TESRCPTQGEPSLNEEQDKRFVCKHSMVDRG | 350-380 | 48 |
| P14340\|POLG_DEN2N | TDSRCPTQGEPSLNEEQDKRFVCKHSMVDRG | 350-380 | 49 |
| P18356\|POLG_DEN2U | TESRCPTQGEPSLNEEQDKRFVCKHSMVDRG | 250-280 | 50 |
| P29984\|POLG_DEN2H | TESRCPIQGEPSLNEEQDKRFVCKHSMVDRG | 119-149 | 51 |
| P27914\|POLG_DEN2T | TDSRCPTQGEPTLNEEQDKRFVCKHSMVDRG | 70-100 | 52 |
| Q99D35\|POLG_DEN3C | TDSRCPTQGEAILPEEQDQNYVCKHTYVDRG | 350-380 | 53 |
| Q6YMS3\|POLG_DEN3M | TDSRCPTQGEAVLPEEQDQNYVCKHTYVDRG | 350-380 | 54 |
| P27915\|POLG_DEN3P | TDSRCPTQGEAILPEEQDQNYVCKHTYVDRG | 350-380 | 55 |
| Q5UB51\|POLG_DEN3I | TDSRCPTQGEAILPEEQDQNYVCKHTYVDRG | 350-380 | 56 |
| Q6YMS4\|POLG_DEN3S | TDSRCPTQGEAVLPEEQDQNYVCKHTYVDRG | 350-380 | 57 |
| P09866\|POLG_DEN4D | TATRCPTQGEPYLKEEQDQQYICRRDVVDRG | 349-379 | 58 |
| Q58HT7\|POLG_DEN4P | TATRCPTQGEPYLKEEQDQQYICRRDVVDRG | 349-379 | 59 |
| Q5UCB8\|POLG_DEN4S | TATRCPTQGEPYLKEEQDQQYICRRDVVDRG | 349-379 | 60 |
| Q2YHF0\|POLG_DEN4T | TATRCPTQGEPYLKEEQDQQYICRRDMVDRG | 349-379 | 61 |
| Q2YHF2\|POLG_DEN4H | TATRCPTQGEPYLKEEQDQQYICRRDVVDRG | 349-379 | 62 |
| P06935\|POLG_WNV | TRAACPTMGEAHNEKRADPAFVCKQGVVDRG | 360-390 | 63 |
| Q9Q6P4\|POLG_WNV9 | TKAACPTMGEAHNDKRADPAFVCRQGVVDRG | 360-390 | 64 |
| P14335\|POLG_KUNJM | TKAACPTMGEAHNDKRADPSFVCKQGVVDRG | 360-390 | 65 |
| P32886\|POLG_JAEVJ | TVARCPTTGEAHNEKRADSSYVCKQGFTDRG | 364-394 | 66 |
| P0DOH8\|POLS_JAEVJ | TVARCPTTGEAHNEKRADSSYVCKQGFTDRG | 364-394 | 67 |
| P09732\|POLG_STEVM | TVARCPTTGEAHNTKRSDPTFVCKRDVVDRG | 358-388 | 68 |
| Q9YRV3\|POLG_YEFVT | IDDRCPSTGEAHLAEENEGDNACKRTYSDRG | 355-385 | 69 |
| Q1X881\|POLG_YEFVN | INDRCPSTGEAHLAEENDGDNACKRTYSDRG | 355-385 | 70 |
| Q074N0\|POLG_YEFVE | INDRCPSTGEAHLAEENDGDNACKRTYSDRG | 355-385 | 71 |
| Q6J3P1\|POLG_YEFVC | INDRCPSTGEAHLAEENEGDNACKRTYSDRG | 355-385 | 72 |
| Q98803\|POLG_YEFVI | INDRCPSTGEAHLAEENEGDNACKRTYSDRG | 355-385 | 73 |
| P29165\|POLG_YEFV8 | INDRCPSTGEAHLAEENEGDHACKRTYSDRG | 355-385 | 74 |
| Q1X880\|POLG_YEFVU | INDRCPSTGEAHLAEENDGDNACKRTYSDRG | 355-385 | 75 |
| P03314\|POLG_YEFV1 | INDRCPSTGEAHLAEENEGDNACKRTYSDRG | 355-385 | 76 |
| Q89277\|POLG_YEFVF | INDRCPSTGEAHLAEENEGDNACKRTYSDRG | 355-385 | 77 |
| Q6DV88\|POLG_YEFVA | INDRCPSTGEAHLAEENEGDNACKRTYSDRG | 355-385 | 78 |
| A0A024B7W1\|POLG_ZIKVF | SDSRCPTQGEAYLDKQSDTQYVCKRTLVDRG | 360-390 | 79 |
| Q32ZE1\|POLG_ZIKV | SDSRCPTQGEAYLDKQSDTQYVCKRTLVDRG | 360-390 | 80 |

FIG. 6A

| UniProtKB Acc. No. | Sequence | Position | SEQ ID NO: |
|---|---|---|---|
| Q91B85 | POLG_ALKV | VVARCPAMGPATLPEEHQASTVCRRDQSDRG | 351-381 | 81 |
| C8XPA8 | POLG_BANV | IATACPSNGEAKLDEEHIKEYACKRLYSDRG | 342-372 | 82 |
| Q32ZE0 | POLG_BUSV | ISAACPAVQLTENSKATDSNYLCRRGVTNRG | 362-392 | 83 |
| C8XPB2 | POLG_EHV | VQTACPTNGEAKLEEEASAEYECKKTYSDRG | 351-381 | 84 |
| Q32ZD7 | POLG_ILHV | TEARCPTMGEAHNSKSLDASYVCKSSYVDRG | 355-385 | 85 |
| Q32ZD5 | POLG_KOKV | VETRCPTMGEAHNSKSSDAAYVCKKGFSDRG | 356-386 | 86 |
| D7RF80 | POLG_KFDV | VAARCPAMGPATLPEEHQASTVCRRDQSDRG | 351-381 | 87 |
| P29837 | POLG_LANVT | VAARCPTMGPATLPEEHQSGTVCKRDQSDRG | 350-380 | 88 |
| P29838 | POLG_LANVY | VAARCPTMGPATLPEEHQSGTVCKRDQSDRG | 350-380 | 89 |
| P22338 | POLG_LIV | VAARCPTMGPAVLTEERQIGTVCKRDQSDRG | 350-380 | 90 |
| P35764 | POLG_LIV31 | VAARCPTMGPAALAEERQIGTVCKRDQSDRG | 70-100 | 91 |
| P35765 | POLG_LIVK | VAARCPTMGPAVLTEERQIGTVCKRDQSDRG | 70-100 | 92 |
| Q02478 | POLG_LIVN1 | VAARCPTMGPAVLTEEHQIGTVCKRDQSDRG | 70-100 | 93 |
| P35766 | POLG_LIVNO | VAARCPTMGPAVLTEERQIGTVCKRDQSDRG | 70-100 | 94 |
| Q02012 | POLG_LIVSB | VAARCPTMGPAALAEERQIGTVCKRDQSDRG | 70-100 | 95 |
| P05769 | POLG_MVEV5 | TVSNCPTTGESHNTKRADHNYLCKRGVTDRG | 362-392 | 96 |
| Q7T6D2 | POLG_OHFV | VAARCPAMGPATLDEEHQSGTVCKRDQSDRG | 350-380 | 97 |
| Q32ZD4 | POLG_ROCV | SEARCPTMGEAHNPKALDSNYLCKSTYVDRG | 355-385 | 98 |
| P14336 | POLG_TBEVW | VAARCPTMGPATLAEEHQGGTVCKRDQSDRG | 350-380 | 99 |
| P07720 | POLG_TBEVS | VAARCPTMGPATLAEEHQSGTVCKRDQSDRG | 350-380 | 100 |
| Q01299 | POLG_TBEVH | VAARCPTMGPATLAEEHQGGTVCKRDQSDRG | 350-380 | 101 |
| Q04538 | POLG_POWVL | VEARCPTTGPATLPEEHQANMVCKRDQSDRG | 348-378 | 102 |
| Q5WPU5 | POLG_USUV | TVSNCPTTGEAHNPKRAEDTYVCKSGVTDRG | 363-393 | 103 |
| C5H431 | POLG_WSLV | ATGACPTMGDAHMSEEGNEEWECKRSYSDRG | 350-380 | 104 |
| CONSENSUS 1 | | CXXXXXXRG | | 105 |
| CONSENSUS 2 | | XXXXCP | | 106 |

FIG. 6B

| UniProtKB Acc. No. | Sequence | Position | SEQ ID NO: |
|---|---|---|---|
| P27909\|POLG_DEN1B | VTFKTAHA QEVVVLGSQEGAMHTALT | 518-545 | 107 |
| P27913\|POLG_DEN1C | VTFKTAHA QEVVVLGSQEGAMHTALT | 518-545 | 108 |
| P17763\|POLG_DEN1W | VTFKTAHA QEVVVLGSQEGAMHTALT | 518-545 | 109 |
| P33478\|POLG_DEN1S | VTFKTAHA QEVVVLGSQEGAMHTALT | 518-545 | 110 |
| P27912\|POLG_DEN1A | VTFKTAHA QEVVVLGSQEGAMHTALT | 518-545 | 111 |
| P14338\|POLG_DEN22 | VTFKNPHA QDVVVLGSQEGAMHTALT | 238-265 | 112 |
| P14339\|POLG_DEN23 | VTFKNPHA QDVVVLGSQEGAMQTALT | 238-265 | 113 |
| P14337\|POLG_DEN28 | VTFKNPHA QDVVVLGSQEGAMHTALT | 518-545 | 114 |
| P29991\|POLG_DEN27 | VTFKNPHA QDVVVLGSQEGAMHTALT | 518-545 | 115 |
| P30026\|POLG_DEN2D | VTFKNPHA QDVVVLGSQEGAMHTALT | 518-545 | 116 |
| P07564\|POLG_DEN2J | VTFKNPHA QDVVVLGSQEGAMHTALT | 518-545 | 117 |
| Q9WDA6\|POLG_DEN2Q | VTFKNPHA QDVVVLGSQEGAMHTALT | 518-545 | 118 |
| P12823\|POLG_DEN2P | VTFKNPHA QDVVVLGSQEGAMHTALT | 518-545 | 119 |
| P29990\|POLG_DEN26 | VTFKNPHA QDVVVLGSQEGAMHTALT | 518-545 | 120 |
| P14340\|POLG_DEN2N | VTFKNPHA QDVVVLGSQEGAMHTALT | 518-545 | 121 |
| P18356\|POLG_DEN2U | VTFKNPHA QDVVVLGSQEGAMHTALT | 418-445 | 122 |
| P29984\|POLG_DEN2H | VTFKNPHA QDVVVLGSQEGAMHTALT | 287-314 | 123 |
| P27914\|POLG_DEN2T | VTFKNPHA QDVVVLGSQEGAMHTALT | 238-265 | 124 |
| Q99D35\|POLG_DEN3C | VTFKNAHA QEVVVLGSQEGAMHTALT | 516-543 | 125 |
| Q6YMS3\|POLG_DEN3M | VTFKNAHA QEVVVLGSQEGAMHTALT | 516-543 | 126 |
| P27915\|POLG_DEN3P | VTFKNAHA QEVVVLGSQEGAMHTALT | 516-543 | 127 |
| Q5UB51\|POLG_DEN3I | VTFKNAHA QEVVVLGSQEGAMHTALT | 516-543 | 128 |
| Q6YMS4\|POLG_DEN3S | VTFKNAHA QEVVVLGSQEGAMHTALT | 516-543 | 129 |
| P09866\|POLG_DEN4D | VTFKVPHA RQDVTVLGSQEGAMHSALA | 517-544 | 130 |
| Q58HT7\|POLG_DEN4P | VTFKVPHA RQDVTVLGSQEGAMHSALT | 517-544 | 131 |
| Q5UCB8\|POLG_DEN4S | VTFKVPHA RQDVTVLGSQEGAMHSALA | 517-544 | 132 |
| Q2YHF0\|POLG_DEN4T | VTFKVPHA RQDVTVLGSQEGAMHSALA | 517-544 | 133 |
| Q2YHF2\|POLG_DEN4H | VTFKVPHA RQDVTVLGSQEGAMHSALT | 517-544 | 134 |
| P06935\|POLG_WNV | MEFEEPHAT QSVVALGSQEGALHQALA | 526-553 | 135 |
| Q9Q6P4\|POLG_WNV9 | MEFEEPHAT QSVIALGSQEGALHQALA | 530-557 | 136 |
| P14335\|POLG_KUNJM | MEFEEPHAT QSVIALGSQEGALHQALA | 530-557 | 137 |
| P32886\|POLG_JAEVJ | MEFEEAHAT QSVVALGSQEGGLHQALA | 534-561 | 138 |
| P0DOH8\|POLS_JAEVJ | MEFEEAHAT QSVVALGSQEGGLHQALA | 534-561 | 139 |
| P09732\|POLG_STEVM | VEFEEPHAT QTVVALGSQEGALHTALA | 528-555 | 140 |
| Q9YRV3\|POLG_YEFVT | VEFEPPHAATIRVLALGDQEGSLKTALT | 517-544 | 141 |
| Q1X881\|POLG_YEFVN | VEFEPPHAATIRVLALGNQEGSLKTALT | 517-544 | 142 |
| Q074N0\|POLG_YEFVE | VEFEPPHAATIRVLALGNQEGSLKTALT | 517-544 | 143 |
| Q6J3P1\|POLG_YEFVC | VEFEPPHAATIRVLALGNQEGSLKTALT | 517-544 | 144 |
| Q98803\|POLG_YEFVI | VEFEPPHAATIRVLALGNQEGSLKTALT | 517-544 | 145 |
| P29165\|POLG_YEFV8 | VEFEPPHAATIKVLALGNQEGSLKTALT | 517-544 | 146 |
| Q1X880\|POLG_YEFVU | VEFEPPHAATIRVLALGNQEGSLKTALT | 517-544 | 147 |
| P03314\|POLG_YEFV1 | VEFEPPHAATIRVLALGNQEGSLKTALT | 517-544 | 148 |
| Q89277\|POLG_YEFVF | VEFEPPHAATIRVLALGDQEGSLKTALT | 517-544 | 149 |
| Q6DV88\|POLG_YEFVA | VEFEPPHAATIRVLALGNQEGSLKTALT | 517-544 | 150 |
| A0A024B7W1\|POLG_ZIKVF | VEFKDAHA RQTVVVLGSQEGAVHTALA | 533-560 | 151 |
| Q32ZE1\|POLG_ZIKV | VEFKDAHA RQTVVVLGSQEGAVHTALA | 529-556 | 152 |

FIG. 7A

| UniProtKB Acc. No. | Sequence | Position | SEQ ID NO: |
|---|---|---|---|
| Q91B85\|POLG_ALKV | VEFGEPHAV MDIFNLGDQTGILLKSLA | 523-550 | 153 |
| C8XPA8\|POLG_BANV | VEFGEPHATTVKVLALGPQEGALRNALA | 503-530 | 154 |
| Q32ZE0\|POLG_BUSV | VEFQEPHAT QEVLALGSQEGALHSALA | 531-558 | 155 |
| C8XPB2\|POLG_EHV | VEFTEPHATTMTVMVLGAQEGALRTALA | 512-539 | 156 |
| Q32ZD7\|POLG_ILHV | IEFEEPHATRQTVVALGNQEGALHTALA | 525-552 | 157 |
| Q32ZD5\|POLG_KOKV | VEFGKTHAT REVLALGSQEGTLQVALA | 526-553 | 158 |
| D7RF80\|POLG_KFDV | VEFGEPHAV MDIFNLGDQTGILLKSLA | 523-550 | 159 |
| P29837\|POLG_LANVT | VEFGTPHAV MDVFNLGDQTGVLLKSLA | 522-549 | 160 |
| P29838\|POLG_LANVY | VEFGTPHAV MDVFNLGDQTGVLLKSLA | 522-549 | 161 |
| P22338\|POLG_LIV | VEFGAPHAV MDVYNLGDQTGVLLRALA | 522-549 | 162 |
| P35764\|POLG_LIV31 | VEFGAPHAV MDVYNLGDQTGVLLKALA | 242-269 | 163 |
| P35765\|POLG_LIVK | VEFGAPHAV MDVYNLGDQTGVLLKALA | 242-269 | 164 |
| Q02478\|POLG_LIVN1 | VEFGVPHAV MDVYNLGDQTGVLLKALA | 242-269 | 165 |
| P35766\|POLG_LIVNO | VEFGAPHAV MDVYNLGDQTGVLLKALA | 242-269 | 166 |
| Q02012\|POLG_LIVSB | VEFGAPHAV MDVYNLGDQTGVLLKALA | 242-269 | 167 |
| P05769\|POLG_MVEV5 | VEFEEPHAT QSVVALGSQEGALHQALA | 532-559 | 168 |
| Q7T6D2\|POLG_OHFV | VEFGVPHAV MDVYNLGDQTGVLLKSLA | 522-549 | 169 |
| Q32ZD4\|POLG_ROCV | VEFEEAHVT QTVVALAAQEGELHIVLA | 525-552 | 170 |
| P14336\|POLG_TBEVW | VEFGAPHAV MDVYNLGDQTGVLLKALA | 522-549 | 171 |
| P07720\|POLG_TBEVS | VEFGAPHAV MDVYNLGDQTGVLLKSLA | 522-549 | 172 |
| Q01299\|POLG_TBEVH | VEFGAPHAV MDVYNLGDQTGVLLKALA | 522-549 | 173 |
| Q04538\|POLG_POWVL | VEFGPPHAV MDVFNLGDQTAVLLKSLA | 520-547 | 174 |
| Q5WPU5\|POLG_USUV | LEFEEPHAT QSVVALGSQEGALHQALA | 533-560 | 175 |
| C5H431\|POLG_WSLV | VDFEEPHAVTMKALVLGSQEGALRTALS | 512-539 | 176 |
| CONSENSUS 3 | FXXXHXXXXX | | 177 |
| CONSENSUS 4 | LXXQXX | | 178 |

FIG. 7B

| UniProtKB Acc. No. | Sequence 1 | Sequence 2 | SEQ ID NOs: |
|---|---|---|---|
| P27909\|POLG_DEN1B | TDSRCPTQGEATLVEEQDANFVCRRTFVDRG | VTFKTAHAKQEVVVLGSQEGAMHTALT | 35; 107 |
| P27913\|POLG_DEN1C | TDSRCPTQGEATLVEEQDANFVCRRTFVDRG | VTFKTAHAKQEVVVLGSQEGAMHTALT | 36; 108 |
| P17763\|POLG_DEN1W | TDSRCPTQGEATLVEEQDTNFVCRRTFVDRG | VTFKTAHAKQEVVVLGSQEGAMHTALT | 37; 109 |
| P33478\|POLG_DEN1S | TDSRCPTQGEATLVEEQDANFVCRRTFVDRG | VTFKTAHAKQEVVVLGSQEGAMHTALT | 38; 110 |
| P27912\|POLG_DEN1A | TDSRCPTQGEATLVEEQDTNFVCRRTFVDRG | VTFKTAHAKQEVVVLGSQEGAMHTALT | 39; 111 |
| P14338\|POLG_DEN2Z | TESRCPTQGEPSLNEEQDKRFVCKHSMVDRG | VTFKNPHAKQDVVVLGSQEGAMHTALT | 40; 112 |
| P14339\|POLG_DEN2B | TESRCPTLGEPSLNEEQDKRLVCKHSMVDRG | VTFKNPHAKQDVVVLGSQEGAMQTALT | 41; 113 |
| P14337\|POLG_DEN2S | TESRCPTQGEPSLNEEQDKRFVCKHSMVDRG | VTFKNPHAKQDVVVLGSQEGAMHTALT | 42; 114 |
| P29991\|POLG_DEN2V | TESRCPTQGEPSLNEEQDKRFVCKHSMVDRG | VTFKNPHAKQDVVVLGSQEGAMHTALT | 43; 115 |
| P30026\|POLG_DEN2D | TESRCPTQGEPSLNEEQDKRFVCKHSMVDRG | VTFKNPHAKQDVVVLGSQEGAMHTALT | 44; 116 |
| P07564\|POLG_DEN2J | TESRCPTQGEPSLNEEQDKRFLCKHSMVDRG | VTFKNPHAKQDVVVLGSQEGAMHTALT | 45; 117 |
| Q9WDA6\|POLG_DEN2Q | TDSRCPTQGEPTLNEEQDKRFVCKHSMVDRG | VTFKNPHAKQDVVVLGSQEGAMHTALT | 46; 118 |
| P12823\|POLG_DEN2P | TDSRCPTQGEPTLNEEQDKRFVCKHSMVDRG | VTFKNPHAKQDVVVLGSQEGAMHTALT | 47; 119 |
| P29990\|POLG_DEN2C | TESRCPTQGEPSLNEEQDKRFVCKHSMVDRG | VTFKNPHAKQDVVVLGSQEGAMHTALT | 48; 120 |
| P14340\|POLG_DEN2N | TDSRCPTQGEPSLNEEQDKRFVCKHSMVDRG | VTFKNPHAKQDVVVLGSQEGAMHTALT | 49; 121 |
| P18356\|POLG_DEN2U | TESRCPTQGEPSLNEEQDKRFVCKHSMVDRG | VTFKNPHAKQDVVVLGSQEGAMHTALT | 50; 122 |
| P29984\|POLG_DEN2H | TESRCPIQGEPSLNEEQDKRFVCKHSMVDRG | VTFKNPHAKQDVVVLGSQEGAMHTALT | 51; 123 |
| P27914\|POLG_DEN2T | TDSRCPTQGEPTLNEEQDKRFVCKHSMVDRG | VTFKNPHAKQDVVVLGSQEGAMHTALT | 52; 124 |
| Q99D35\|POLG_DEN3C | TDSRCPTQGEAILPEEQDQNYVCKHTYVDRG | VTFKNAHAKQEVVVLGSQEGAMHTALT | 53; 125 |
| Q6YMS3\|POLG_DEN3M | TDSRCPTQGEAVLPEEQDQNYVCKHTYVDRG | VTFKNAHAKQEVVVLGSQEGAMHTALT | 54; 126 |
| P27915\|POLG_DEN3P | TDSRCPTQGEAILPEEQDQNYVCKHTYVDRG | VTFKNAHAKQEVVVLGSQEGAMHTALT | 55; 127 |
| Q5UB51\|POLG_DEN3I | TDSRCPTQGEAILPEEQDQNYVCKHTYVDRG | VTFKNAHAKQEVVVLGSQEGAMHTALT | 56; 128 |
| Q6YMS4\|POLG_DEN3S | TDSRCPTQGEAVLPEEQDQNYVCKHTYVDRG | VTFKNAHAKQEVVVLGSQEGAMHTALT | 57; 129 |
| P09866\|POLG_DEN4D | TATRCPTQGEPYLKEEQDQQYICRRDVVDRG | VTFKVPHARQDVTVLGSQEGAMHSALA | 58; 130 |
| Q58HT7\|POLG_DEN4P | TATRCPTQGEPYLKEEQDQQYICRRDVVDRG | VTFKVPHARQDVTVLGSQEGAMHSALT | 59; 131 |
| Q5UCB8\|POLG_DEN4S | TATRCPTQGEPYLKEEQDQQYICRRDVVDRG | VTFKVPHARQDVTVLGSQEGAMHSALA | 60; 132 |
| Q2YHF0\|POLG_DEN4T | TATRCPTQGEPYLKEEQDQQYICRRDMVDRG | VTFKVPHARQDVTVLGSQEGAMHSALA | 61; 133 |
| Q2YHF2\|POLG_DEN4H | TATRCPTQGEPYLKEEQDQQYICRRDVVDRG | VTFKVPHARQDVTVLGSQEGAMHSALT | 62; 134 |
| CONSENSUS 5 | TXXRCPXXGEXXLEEQDXXXXCXXXXVDRG | VTFKXXHAKXQXVXVLGSQEGAMXXALX | 179; 180 |
| CONSENSUS 6 | CXXXXVDRG | | 181 |
| CONSENSUS 7 | TXXRCP | | 182 |
| CONSENSUS 8 | | VTFKXXHAKXQX | 183 |
| CONSENSUS 9 | | LGSQEG | 184 |

FIG. 8

| UniProtKB Acc. No. | Sequence 1 | Sequence 2 | SEQ ID NOs: |
|---|---|---|---|
| P27909\|POLG_DEN1B | TDSRCPTQGEATLVEEQDANFVCRRTFVDRG | VTFKTAHA QEVVVLGSQEGAMHTALT | 35; 107 |
| P17763\|POLG_DEN1W | TDSRCPTQGEATLVEEQDTNFVCRRTFVDRG | VTFKTAHA QEVVVLGSQEGAMHTALT | 37; 109 |
| P14338\|POLG_DEN22 | TESRCPTQGEPSLNEEQDKRFVCKHSMVDRG | VTFKNPHA QDVVVLGSQEGAMHTALT | 40; 112 |
| P14339\|POLG_DEN23 | TESRCPTLGEPSLNEEQDKRLVCKHSMVDRG | VTFKNPHA QDVVVLGSQEGAMQTALT | 41; 113 |
| Q9WDA6\|POLG_DEN2Q | TDSRCPTQGEPTLNEEQDKRFVCKHSMVDRG | VTFKNPHA QDVVVLGSQEGAMHTALT | 46; 118 |
| P14340\|POLG_DEN2N | TDSRCPTQGEPSLNEEQDKRFVCKHSMVDRG | VTFKNPHA QDVVVLGSQEGAMHTALT | 49; 121 |
| P29984\|POLG_DEN2H | TESRCPIQGEPSLNEEQDKRFVCKHSMVDRG | VTFKNPHA QDVVVLGSQEGAMHTALT | 51; 123 |
| Q99D35\|POLG_DEN3C | TDSRCPTQGEAILPEEQDQNYVCKHTYVDRG | VTFKNAHA QEVVVLGSQEGAMHTALT | 53; 125 |
| Q6YMS3\|POLG_DEN3M | TDSRCPTQGEAVLPEEQDQNYVCKHTYVDRG | VTFKNAHA QEVVVLGSQEGAMHTALT | 54; 126 |
| P09866\|POLG_DEN4D | TATRCPTQGEPYLKEEQDQQYICRRDVVDRG | VTFKVPHA RQDVTVLGSQEGAMHSALA | 58; 130 |
| P06935\|POLG_WNV | TRAACPTMGEAHNEKRADPAFVCKQGVVDRG | MEFEEPHAT QSVVALGSQEGALHQALA | 63; 135 |
| Q9Q6P4\|POLG_WNV9 | TKAACPTMGEAHNDKRADPAFVCRQGVVDRG | MEFEEPHAT QSVIALGSQEGALHQALA | 64; 136 |
| P14335\|POLG_KUNJM | TKAACPTMGEAHNDKRADPSFVCKQGVVDRG | MEFEEPHAT QSVIALGSQEGALHQALA | 65; 137 |
| P32886\|POLG_JAEVJ | TVARCPTTGEAHNEKRADSSYVCKQGFTDRG | MEFEEAHAT QSVVALGSQEGGLHQALA | 66; 138 |
| P09732\|POLG_STEVM | TVARCPTTGEAHNTKRSDPTFVCKRDVVDRG | VEFEEPHAT QTVVALGSQEGALHTALA | 68; 140 |
| A0A024B7W1\|POLG_ZIKVF | SDSRCPTQGEAYLDKQSDTQYVCKRTLVDRG | VEFKDAHA RQTVVVLGSQEGAVHTALA | 79; 151 |
| Q91B85\|POLG_ALKV | VVARCPAMGPATLPEEHQASTVCRRDQSDRG | VEFGEPHAV MDIFNLGDQTGILLKSLA | 81; 153 |
| Q32ZE0\|POLG_BUSV | ISAACPAVQLTENSKATDSNYLCRRGVTNRG | VEFQEPHAT QEVLALGSQEGALHSALA | 83; 155 |
| Q32ZD7\|POLG_ILHV | TEARCPTMGEAHNSKSLDASYVCKSSYVDRG | IEFEEPHAT RQTVVALGNQEGALHTALA | 85; 157 |
| Q32ZD5\|POLG_KOKV | VETRCPTMGEAHNSKSSDAAYVCKKGFSDRG | VEFGKTHAT REVLALGSQEGTLQVALA | 86; 158 |
| D7RF80\|POLG_KFDV | VAARCPAMGPATLPEEHQASTVCRRDQSDRG | VEFGEPHAV MDIFNLGDQTGILLKSLA | 87; 159 |
| P29837\|POLG_LANVT | VAARCPTMGPATLPEEHQSGTVCKRDQSDRG | VEFGTPHAV MDVFNLGDQTGVLLKSLA | 88; 160 |
| P22338\|POLG_LIV | VAARCPTMGPAVLTEERQIGTVCKRDQSDRG | VEFGAPHAV MDVYNLGDQTGVLLRALA | 90; 162 |
| P35764\|POLG_LIV31 | VAARCPTMGPAALAEEERQIGTVCKRDQSDRG | VEFGAPHAV MDVYNLGDQTGVLLKALA | 91; 163 |
| Q02478\|POLG_LIVN1 | VAARCPTMGPAVLTEEHQIGTVCKRDQSDRG | VEFGVPHAV MDVYNLGDQTGVLLKALA | 93; 165 |
| P05769\|POLG_MVEV5 | TVSNCPTTGESHNTKRADHNYLCKRGVTDRG | VEFEEPHAT QSVVALGSQEGALHQALA | 96; 168 |
| Q7T6D2\|POLG_OHFV | VAARCPAMGPATLDEEHQSGTVCKRDQSDRG | VEFGVPHAV MDVYNLGDQTGVLLKSLA | 97; 169 |
| Q32ZD4\|POLG_ROCV | SEARCPTMGEAHNPKALDSNYLCKSTYVDRG | VEFEEAHVT RQTVVALAAQEGEGLHIVLA | 98; 170 |
| P14336\|POLG_TBEVW | VAARCPTMGPATLAEEHQGGTVCKRDQSDRG | VEFGAPHAV MDVYNLGDQTGVLLKALA | 99; 171 |
| P07720\|POLG_TBEVS | VAARCPTMGPATLAEEHQSGTVCKRDQSDRG | VEFGAPHAV MDVYNLGDQTGVLLKSLA | 100; 172 |
| Q04538\|POLG_POWVL | VEARCPTTGPATLPEEHQANMVCKRDQSDRG | VEFGPPHAV MDVFNLGDQTAVLLKSLA | 102; 174 |
| Q5WPU5\|POLG_USUV | TVSNCPTTGEAHNPKRAEDTYVCKSGVTDRG | LEFEEPHAT QSVVALGSQEGALHQALA | 103; 175 |
| CONSENSUS 10 | XXXXCPXXXXXXXXXXXXXXXCXXXXXXXRG | XXFXXXHXXXXXXXXXLXXQXXXXXXXLX | 185; 186 |
| CONSENSUS 11 | CXXXXXXRG | | 187 |
| CONSENSUS 12 | XXXRCP | | 188 |
| CONSENSUS 13 | | XXFXXXHXXXXX | 189 |
| CONSENSUS 14 | | XHXXX | 190 |
| CONSENSUS 15 | | LXXQXX | 191 |

FIG. 9

Envelope protein E, Dengue virus type 2 (strain Thailand/NGS-C/1944) (DENV-2), UniProtKB Acc. No. P14340, position 281 - 775 (SEQ ID NO:192)

```
MRCIGISNRDFVEGVSGGSWVDIVLEHGSCVTTMAKNKPTLDFELIETEAKQPATLRKYC    60

IEAKLTNTTTDSRCPTQGEPSLNEEQDKRFVCKHSMVDRGWGNGCGLFGKGGIVTCAMFT   120
                                    fusion loop (98-111)

CKKNMKGKVVQPENLEYTIVITPHSGEEHAVGNDTGKHGKEIKITPQSSITEAELTGYGT   180

VTMECSPRTGLDFNEMVLLQMENKAWLVHRQWFLDLPLPWLPGADTQGSNWIQKETLVTF   240

KNPHA QDVVVLGSQEGAMHTALTGATEIQMSSGNLLFTGHLKCRLRMDKLQLKGMSYS    300

MCTGKFKVVKEIAETQHGTIVIRVQYEGDGSPCKIPFEIMDLEKRHVLGRLITVNPIVTE   360

KDSPVNIEAEPPFGDSYIIIGVEPGQLKLNWFKKGSSIGQMIETTMRGAKRMAILGDTAW   420

DFGSLGGVFTSIGKALHQVFGAIYGAAFSGVSWIMKILIGVIITWIGMNSRSTSLSVSLV   480

LVGVVTLYLGVMVQA                                                495
```

INHIBITORS FOR TARGETING FLAVIVIRUSES

CROSS-REFERENCE TO RELATED APPLICATION

This application claims the benefit of U.S. Provisional Application No. 62/767,323, filed Nov. 14, 2018, which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

REFERENCE TO A SEQUENCE LISTING APPENDIX

A sequence listing appendix including an ASCII formatted file accompanies this application. The appendix includes a file named "SD14125.1_ST25.txt," created on Feb. 3, 2020 (size of 444 kilobytes), which is hereby incorporated by reference in its entirety.

FIELD OF THE INVENTION

The present invention relates to methods for identifying candidate therapeutics for a disease caused by a viral envelope protein. In particular, the method can include contacting a test envelope protein with the candidate and determining its activity.

BACKGROUND OF THE INVENTION

Entry of viruses into host cells is critical for infectivity. Although structural studies have identified proteins that facilitate entry, functional mechanisms still remain in question. Accordingly, there is a need to more fully understand what proteins and specific amino acids contribute to viral entry.

SUMMARY OF THE INVENTION

The present invention relates, in part, to methods for identifying a candidate therapeutic for a disease caused by a viral envelope protein and methods of treating a viral infection in a subject. In particular embodiments, the viral protein or viral infection relates to a flavivirus.

As described herein, we have determined that particular residues within a viral envelope (E) protein facilitates interaction between the E protein and a lipid layer of the host. These interactions arise from hydrogen bonding between the amino acid residues and the lipid headgroups and, ultimately, result in deformation of the lipid layer. Such deformation may be important for fusion of the virus to the host's lipid layer within the endosome. In particular, we have identified the contribution of residues R73, R99, K246, and/or K247 (in reference to the sequence of the E protein) to such hydrogen bonding interactions. Accordingly, these residues could serve as viable targets to disrupt viral fusion and, therefore, mitigate viral infection.

Accordingly, in a first aspect, the present invention features a method for identifying a candidate therapeutic for a disease caused by a viral envelope protein, the method including: contacting a test envelope protein with a compound; and determining an activity of the compound with the test protein, where the activity indicates greater inhibition of viral entry, as compared to a control.

In some embodiments, the test protein includes a first sequence having at least 80% sequence identity to any one of SEQ ID NOs:35-104 or having any one of SEQ ID NOs: 105, 106, 179, 181, 182, 185, 187, and 188. In other embodiments, the test protein includes a second sequence having at least 80% sequence identity to any one of SEQ ID NOs: 107-176 or having any one of SEQ ID NOs: 177, 178, 180, 183, 184, 186, and 189-191. In yet other embodiments, the second sequence includes a lysine at position 9 and/or position 10.

In a second aspect, the present invention features a method for identifying a candidate therapeutic for a disease caused by a viral envelope protein, the method including contacting a test envelope protein with a compound; determining an activity of the compound with the test protein; contacting a mutant viral envelope protein with the compound, where the mutant protein includes the sequence of the test protein with a mutation in the second sequence at position 9 and/or position 10; determining an activity of the compound with the mutant protein; and comparing the activity of the compound with the test protein and the mutant protein, where the activity of the test protein indicates greater inhibition, as compared to the mutant protein.

In some embodiments, the test protein includes a first sequence having at least 80% sequence identity to any one of SEQ ID NOs:35-104 and a second sequence having at least 80% sequence identity to any one of SEQ ID NOs: 107-176. In other embodiments, the second sequence includes a lysine at position 9 and/or position 10. In some embodiments, the second sequence of the test protein includes a lysine at positions 9 and 10. In some embodiments, the mutation in the second sequence at position 9 and/or 10 includes a glycine, alanine, valine, leucine, isoleucine, methionine, aspartic acid, glutamic acid, asparagine, or glutamine.

In some embodiments, the first sequence of the test protein includes an arginine at position 30. In other embodiments, the mutation in the first sequence at position 30 includes a glycine, alanine, valine, leucine, isoleucine, methionine, aspartic acid, glutamic acid, asparagine, or glutamine. In yet other embodiments, the test protein includes an arginine at position 30 of the first sequence, a lysine at position 9 of the second sequence, and/or a lysine at position 10 of the second sequence.

In some embodiments, the first sequence of the mutant protein includes a mutation at position 30. In other embodiments, the mutant protein includes a mutation at position 30 of the first sequence, at position 9 of the second sequence, and/or at position 10 of the second sequence.

In a third aspect, the present invention features a method for identifying a candidate therapeutic for a disease caused by a viral envelope protein, the method including: contacting a test envelope protein with a compound, where the test protein includes a first sequence having any one of SEQ ID NOs:105, 106, 179, 181, 182, 185, 187, and 188 and a second sequence having any one of SEQ ID NOs:177, 178, 180, 183, 184, 186, and 189-191, where the second sequence includes a lysine at position 9 and/or position 10; determining an activity of the compound with the test protein; contacting a mutant viral envelope protein with the compound, where the mutant protein includes the sequence of the test protein with a mutation in the second sequence at position 9 and/or position 10; determining an activity of the compound with the mutant protein; and comparing the activity of the compound with the test protein and the mutant protein, where the activity of the test protein indicates greater inhibition, as compared to the mutant protein.

In some embodiments, the first sequence of the test protein includes an arginine at position 30. In other embodiments, the first sequence of the mutant protein includes a mutation at position 30.

In a fourth aspect, the present invention features a method for identifying a candidate therapeutic for a disease caused by a viral envelope protein, the method including: contacting a test envelope protein with a compound, where the test protein includes a sequence having at least 80% sequence identity to SEQ ID NO: 192, where the sequence includes an arginine at position 73, an arginine at position 99, a lysine at position 246, and/or a lysine at position 247; and determining an activity of the compound with the test protein, where the activity indicates greater inhibition of viral entry, as compared to a control.

In a fifth aspect, the present invention features a method for identifying a candidate therapeutic for a disease caused by a viral envelope protein, the method including: contacting a test envelope protein with a compound, where the test protein includes a sequence having at least 80% sequence identity to SEQ ID NO: 192, where the sequence includes an arginine at position 73, an arginine at position 99, a lysine at position 246, and/or a lysine at position 247; determining an activity of the compound with the test protein; contacting a mutant viral envelope protein with the compound, where the mutant protein includes the sequence of the test protein with at position 73, 99, 246, and/or 247; determining an activity of the compound with the mutant protein; and comparing the activity of the compound with the test protein and the mutant protein, where the activity of the test protein indicates greater inhibition, as compared to the mutant protein.

In some embodiments, the mutation at position 73, 99, 246, and/or 247 includes a glycine, alanine, valine, leucine, isoleucine, methionine, aspartic acid, glutamic acid, asparagine, or glutamine.

In some embodiments, the test protein includes a lysine at position 246 and a lysine at position 247. In other embodiments, the test protein includes an arginine at position 99.

In some embodiments, the mutant protein includes a mutation at positions 99, 246, and 247.

In a sixth aspect, the present invention features a method of treating a viral infection in a subject, the method including: administering an effective amount of a lysine inhibitor and/or an arginine inhibitor to the subject, thereby treating the viral infection, where the infection arises from a flavivirus. In particular embodiments, the method include administering an effective amount of a lysine inhibitor and an arginine inhibitor.

In some embodiments, the flavivirus is a mosquito-borne virus. In particular embodiments, the flavivirus is an Alkhumra hemorrhagic fever virus, Bussuquara virus, Chaoyang virus, Dengue virus, Donggang virus, Ilheus virus, Japanese encephalitis virus, Kedougou virus, Kokobera virus, Kunjin virus, Kyasanur Forest disease virus, Langat virus, Layer flavivirus, Louping ill virus, Murray Valley encephalitis virus, Omsk hemorrhagic fever virus, Powassan virus, Rocio virus, St. Louis encephalitis virus, tick-borne encephalitis virus, Usutu virus, West Nile virus, or Zika virus.

In some embodiments, the lysine inhibitor is selected from the group consisting of a compound having structures (I), (II), (III), or (IV) or a salt thereof. In some embodiments, the compound has a structure of formula (I):

(I)

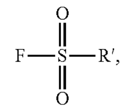

or a salt thereof, wherein:

R' is optionally substituted alkyl, optionally substituted heteroalkyl, optionally substituted aryl, optionally substituted alkaryl, optionally substituted heterocyclyl, optionally substituted alkheterocyclyl, optionally substituted cycloalkyl, optionally substituted alkcycloalkyl, or -Lk-R, in which Lk is a linker (e.g., such as an optionally substituted alkylene, alkyleneoxy, heteroalkylene, heteroalkyleneoxy, arylene, or aryleneoxy) and R is any useful moiety (e.g., an organic moiety), including but not limited to an optionally substituted alkyl, optionally substituted heteroalkyl, optionally substituted aryl, optionally substituted alkaryl, optionally substituted heterocyclyl, optionally substituted alkheterocyclyl, optionally substituted cycloalkyl, or optionally substituted alkcycloalkyl.

In some embodiments, the compound has a structure of formula (II):

(II)

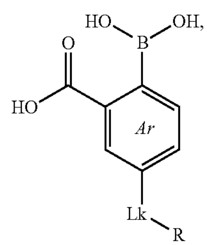

or a salt thereof, wherein:

Ar is optionally substituted aryl, optionally substituted alkaryl, optionally substituted heterocyclyl, optionally substituted alkheterocyclyl, optionally substituted heteroaryl, or optionally substituted alkheteroaryl (e.g., as defined herein);

Lk is a bond or linker (e.g., such as a covalent bond, oxy, optionally substituted alkylene, optionally substituted alkyleneoxy, optionally substituted heteroalkylene, optionally substituted heteroalkyleneoxy, optionally substituted arylene, or optionally substituted aryleneoxy); and R is any useful moiety (e.g., an organic moiety), including but not limited to an optionally substituted aryl, optionally substituted alkaryl, optionally substituted heterocyclyl, optionally substituted alkheterocyclyl, optionally substituted heteroaryl, or optionally substituted alkheteroaryl.

In some embodiments, the compound has a structure of formula (III):

(III)

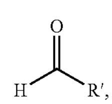

or a salt thereof, wherein:

R' is optionally substituted alkyl, optionally substituted heteroalkyl, optionally substituted aryl, optionally substituted alkaryl, optionally substituted heterocyclyl, optionally substituted alkheterocyclyl, optionally substituted cycloalkyl, optionally substituted alkcycloalkyl, or -Lk-R, in which Lk is a bond or linker (e.g., such as a covalent bond, oxy, optionally substituted alkylene, optionally substituted alkyleneoxy, optionally substituted heteroalkylene, optionally substituted heteroalkyleneoxy, optionally substituted arylene, or optionally substituted aryleneoxy) and R is any useful moiety (e.g., an organic moiety), including but not limited to optionally substituted alkyl, optionally substituted heteroalkyl, optionally substituted aryl, optionally substituted alkaryl, optionally substituted heterocyclyl, optionally substituted alkheterocyclyl, optionally substituted cycloalkyl, or optionally substituted alkcycloalkyl.

In some embodiments, the compound has a structure of formula (IV):

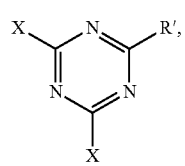

(IV)

or a salt thereof, wherein:

R' is optionally substituted alkyl, optionally substituted heteroalkyl, optionally substituted aryl, optionally substituted alkaryl, optionally substituted heterocyclyl, optionally substituted alkheterocyclyl, optionally substituted cycloalkyl, optionally substituted alkcycloalkyl, or -Lk-R, in which Lk is a bond or a linker (e.g., such as a covalent bond, oxy, optionally substituted alkylene, optionally substituted alkyleneoxy, optionally substituted heteroalkylene, optionally substituted heteroalkyleneoxy, optionally substituted arylene, or optionally substituted aryleneoxy) and R is any useful moiety (e.g., an organic moiety), including but not limited to optionally substituted alkyl, optionally substituted heteroalkyl, optionally substituted aryl, optionally substituted alkaryl, optionally substituted heterocyclyl, optionally substituted alkheterocyclyl, optionally substituted cycloalkyl, or optionally substituted alkcycloalkyl; and each X, independently, is any useful moiety (e.g., a substitution provided for optionally substituted alkyl or aryl, as defined herein), including a leaving group (e.g., halo, alkoxy, haloalkyl, etc.). In some embodiments, X is halo, alkoxy, haloalkoxy, haloalkyl, hydroxy, alkanoyl, aryloyl, heterocyclyloyl, alkylsulfonyl, carboxyaldehyde, or carboxyl.

In some embodiments, the lysine inhibitor is selected from the group consisting of manoalide, seco-manoalide, wortmannin, myriocin, carbaglucose-6-phosphate, an aldehyde terpenoid, a wortmannin analogue, a pyrrole-5-carboxaldehyde inhibitor, an alkyl 6-(N-substituted sulfamoyl) cyclohex-1-ene-1-carboxylate compound, a fluorosulfonyl compound, a sulfonyl fluoride probe, a purine-based cyclin-dependent kinase inhibitor, a stilbene compound, an 8-N-benzyl adenosine reversible inhibitor, an adenosine-derived ATP-competitive inhibitor, an indole-based inhibitor, a peptide inhibitor including an unnatural amino acid with aryl sulfonyl fluoride, an iminoboronate compound, and salts thereof.

In some embodiments, the arginine inhibitor is selected from the group consisting of a compound having structures (V), (VI), or (VII) or a salt thereof. In some embodiments, the compound has a structure of formula (V):

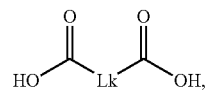

(V)

or a salt thereof, wherein:

Lk is optionally substituted alkylene, optionally substituted alkyleneoxy, optionally substituted heteroalkylene, optionally substituted heteroalkyleneoxy, optionally substituted arylene, or optionally substituted aryleneoxy.

In some embodiments, the compound has a structure of formula (VI):

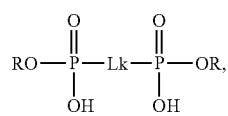

(IV)

or a salt thereof, wherein:

Lk is optionally substituted alkylene, optionally substituted alkyleneoxy, optionally substituted heteroalkylene, optionally substituted heteroalkyleneoxy, optionally substituted arylene, or optionally substituted aryleneoxy; and each R is, independently, H, optionally substituted alkyl, optionally substituted heteroalkyl, optionally substituted aryl, optionally substituted alkaryl, optionally substituted heterocyclyl, optionally substituted alkheterocyclyl, optionally substituted cycloalkyl, optionally substituted alkcycloalkyl, halo, haloalkyl, hydroxy, alkanoyl, aryloyl, heterocyclyloyl, alkylsulfonyl, carboxyaldehyde, or carboxyl.

In some embodiments, the compound has a structure of formula (VII):

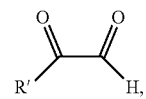

(VII)

or a salt thereof, wherein:

R' is optionally substituted alkyl, optionally substituted heteroalkyl, optionally substituted aryl, optionally substituted alkaryl, optionally substituted heterocyclyl, optionally substituted alkheterocyclyl, optionally substituted cycloalkyl, optionally substituted alkcycloalkyl, or -Lk-R, in which Lk is a bond or a linker (e.g., such as a covalent bond, oxy, optionally substituted alkylene, optionally substituted alkyleneoxy, optionally substituted heteroalkylene, optionally substituted heteroalkyleneoxy, optionally substituted arylene, or optionally substituted aryleneoxy) and R is any useful moiety (e.g., an organic moiety), including but not limited to an optionally substituted alkyl, optionally substituted heteroalkyl, optionally substituted aryl, optionally substituted alkaryl, optionally substituted heterocyclyl, optionally substituted alkheterocyclyl, optionally substituted cycloalkyl, or optionally substituted alkcycloalkyl.

In some embodiments, the arginine inhibitor is selected from the group consisting of phenylglyoxal, p-azidophenylglyoxal, 2,3-butanedione, 1,2-cyclohexanedione, 5,6,9, 10-tetrahydro[1,10]phenanthrolino[2,3-b][1,10]phenanthroline-2,13-dicarboxylic acid, 5,6,9,10-tetrahydrodinaphtho[1, 2-b:2',1'-g][1,8]naphthyridine-2,13-dicarboxylic acid, 5,6,9, 10-tetrahydrobenzo[7,8]quino[2,3-b][1,10]phenanthroline-2,13-dicarboxylic acid, and salts thereof.

In some embodiments, the method further includes administering an additional agent (e.g., together or separately from the inhibitor). In other embodiments, the additional agent can be a NS3/NS2B protease inhibitor, a NS3 helicase inhibitor, a methyltransferase inhibitor, a RNA-dependent RNA polymerase inhibitor, an NS1 inhibitor, an NS2B inhibitor, an NS4B inhibitor, an NS5 polymerase inhibitor, a capsid protein inhibitor, a membrane precursor protein inhibitor, and/or an envelope protein inhibitor.

In any embodiment herein, the test protein includes a first sequence having at least 80% sequence identity to any one of SEQ ID NOs:35-104 or having any one of SEQ ID NOs: 105, 106, 179, 181, 182, 185, 187, and 188. In some embodiments, the first sequence of the test protein includes an arginine at position 30. In other embodiments, the mutation in the first sequence at position 30 includes a glycine, alanine, valine, leucine, isoleucine, methionine, aspartic acid, glutamic acid, asparagine, or glutamine. In yet other embodiments, the test protein includes an arginine at position 30 of the first sequence, a lysine at position 9 of the second sequence, and/or a lysine at position 10 of the second sequence.

In any embodiment herein, the test protein includes a sequence (e.g., a first sequence) having at least 80% sequence identity to SEQ ID NO: 105 and/or SEQ ID NO: 106:

$CX_1X_2X_3X_4X_5X_6RG$ (SEQ ID NO: 105), wherein $X_1$ is R, H, or K (e.g, R or K); $X_2$ is R, H, Q, K, T, N, or S (e.g, R, H, Q, K, or S); $X_3$ is T, S, G, D, E, I, V, or L (e.g, T, S, G, D, or L); $X_4$ is F, M, Y, W, V, A, I, L, N, or Q (e.g., F, M, Y, V, Y, L, or Q); $X_5$ is V, I, L, M, A, T, or S (e.g., V, T, or S); and $X_6$ is D, E, N, or Q (e.g., D or N); or $X_1X_2X_3X_4CP$ (SEQ ID NO: 106), wherein $X_1$ is T, I, S, L, V, or A (e.g., T, I, S, V, or A); $X_2$ is D, E, R, H, K, A, V, I, L, M, N, S, Q, or T (e.g, D, E, R, K, A, V, N, S, Q, or T); $X_3$ is S, T, A, V, I, L, D, E, or G (e.g, S, T, A, D, or G); and $X_4$ is R, A, G, V, I, L, K, H, Q, or N (e.g., R, A, K, or N).

In any embodiment herein, the test protein includes a sequence (e.g., a first sequence) having at least 80% sequence identity to SEQ ID NO: 179 and/or SEQ ID NO: 181 and/or SEQ ID NO:182:

$TX_1X_2RCPX_3X_4GEX_5X_6LX_7EEQDX_8X_9X_{10}X_{11}CX_{12}X_{13}X_{14}X_{15}VDRG$ (SEQ ID NO: 179), wherein $X_1$ is D, E, V, I, L, or A (e.g., D, E, or A); $X_2$ is S or T; $X_3$ is S, T, A, V, I, or L (e.g., T or I); $X_4$ is N, Q, A, V, I, or L (e.g., Q or L); $X_5$ is A, V, I, L, G, or P (e.g., A or P); $X_6$ is T, S, A, L, I, V, F, or Y (e.g., T, S, I, V, or Y); $X_7$ is A, V, I, L, N, Q, G, P, R, or K (e.g, V, N, P, or K); $X_8$ is A, V, I, L, S, T, K, R, N, or Q (e.g. A, T, K, or Q); $X_9$ is N, R, K, H, or Q (e.g, N, R, or Q); $X_{10}$ is F, M, V, I, L, or Y (e.g., F, L, or Y); Xu is A, V, I, or L (e.g., V or L); $X_{12}$ is R, H, or K (e.g, R or K); $X_{13}$ is R, K, or H (e.g, R or H); $X_{14}$ is T, S, E, or D (e.g, T, S, or D); and $X_{15}$ is F, M, I, L, Y, or V (e.g., F, M, Y, or V); or $CX_1X_2X_3X_4VDRG$ (SEQ ID NO: 181), wherein $X_1$ is R, H, or K (e.g, R or K); $X_2$ is R, K, or H (e.g, R or H); $X_3$ is T, S, E, or D (e.g, T, S, or D); and $X_4$ is F, M, I, L, Y, or V (e.g., F, M, Y, or V); or $TX_1X_2RCP$ (SEQ ID NO: 182), wherein $X_1$ is D, E, V, I, L, or A (e.g, D, E, or A); and $X_2$ is S or T.

In any embodiment herein, the test protein includes a sequence (e.g, a first sequence) having at least 80% sequence identity to SEQ ID NO: 185 and/or SEQ ID NO: 187 and/or SEQ ID NO:188:

$X_1X_2X_3X_4CPX_5X_6X_7X_8X_9X_{10}X_{11}X_{12}X_{13}X_{14}X_{15}X_{16}X_{17}X_{18}X_{19}X_{20}CX_{21}X_{22}X_{23}X_{24}X_{25}X_{26}R\ G$ (SEQ ID NO: 185), wherein $X_1$ is T, S, A, V, L, or I (e.g, T, S, V, or I); $X_2$ is D, E, A, I, L, R, H, K, V, T, or S (e.g., D, E, A, R, K, V, or S); $X_3$ is S, T, A, V, I, or L (e.g., S, T, or A); $X_4$ is A, V, I, L, R, K, N, or Q (e.g., R, A, or N); $X_5$ is A, V, I, L, S, or T (e.g., T, I, or A); $X_6$ is N, Q, A, V, I, L, M, S, or T (e.g., Q, V, L, M, or T); $X_7$ is G, N, or Q (e.g., G or Q); $X_8$ is D, E, P, G, A, V, I, or L (e.g., E, P, or L); $X_9$ is A, V, I, L, P, G, T, or S (e.g., A, P, T, or S); $X_{10}$ is T, S, I, V, L, Y, F, H, D, E, or A (e.g, T, S, I, V, Y, H, E, or A); Xu is A, V, I, L, N, or Q (e.g., L or N); $X_{12}$ is V, A, I, L, N, Q, P, R, K, E, D, T, or S (e.g., V, A, N, P, K, E, D, T, or S); $X_{13}$ is D, E, R, or K (e.g., E or K); $X_{14}$ is (e.g., E, R, Q, A, or S); $X_{15}$ is N, Q, A, V, I, L, S, T, H, K, or R (e.g., Q, A, L, S, T, H, or R); $X_{16}$ is D, Q, N, or E (e.g., D, Q, or E); $X_{17}$ is A, V, I, L, S, T, K, R, Q, P, H, G, E, or D (e.g., A, I, S, T, K, Q, P, H, G, or D); $X_{18}$ is N, Q, K, R, A, V, I, L, S, T, or G (e.g., N, Q, R, A, S, T, or G); $X_{19}$ is F, A, V, I, L, Y, S, T, or M (e.g., F, L, Y, T, or M); $X_{20}$ is A, V, I, or L (e.g., V, I, or L); $X_{21}$ is R or K; $X_{22}$ is R, K, S, T, H, N, or Q (e.g., R, K, S, H, or Q); $X_{23}$ is S, T, G, E, or D (e.g, S, T, G, or D); $X_{24}$ is F, A, V, I, L, M, Y, N, or Q (e.g, F, V, L, M, Y, or Q); $X_{25}$ is A, V, I, L, T, or S (e.g., V, T, or S); and $X_{26}$ is E, D, Q, or N (e.g., D or N); or $CX_1X_2X_3X_4X_5X_6RG$ (SEQ ID NO: 187), wherein $X_1$ is R or K; $X_2$ is R, K, S, T, H, N, or Q (e.g, R, K, S, H, or Q); $X_3$ is S, T, G, E, or D (e.g., S, T, G, or D); $X_4$ is F, A, V, I, L, M, Y, N, or Q (e.g., F, V, L, M, Y, or Q); $X_5$ is A, V, I, L, T, or S (e.g., V, T, or S); and $X_6$ is E, D, Q, or N (e.g., D or N); or $X_1X_2X_3RCP$ (SEQ ID NO: 188), wherein $X_1$ is T, S, A, V, L, or I (e.g., T, S, V, or I); $X_2$ is D, E, A, I, L, R, H, K, V, T, or S (e.g, D, E, A, R, K, V, or S); and $X_3$ is S, T, A, V, I, or L (e.g., S, T, or A).

In any embodiment herein, the test protein includes a second sequence having at least 80% sequence identity to any one of SEQ ID NOs: 107-176 or having any one of SEQ ID NOs:177, 178, 180, 183, 184, 186, and 189-191. In yet other embodiments, the second sequence includes a lysine at position 9 and/or position 10. In some embodiments, the mutation in the second sequence at position 9 and/or 10 includes a glycine, alanine, valine, leucine, isoleucine, methionine, aspartic acid, glutamic acid, asparagine, or glutamine.

In any embodiment herein, the test protein includes a sequence (e.g., a second sequence) having at least 80% sequence identity to SEQ ID NO: 177 and/or SEQ ID NO: 178:

$FX_1X_2X_3HX_4X_5X_6X_7X_8$ (SEQ ID NO: 177), wherein $X_1$ is R, K, D, E, G, N, Q, S, or T (e.g., K, E, G, Q, or T); $X_2$ is S, T, N, Q, D, E, G, P, R, H, K, I, L, V, or A (e.g., T, N, D, E, P, K, V, or A); $X_3$ is A, V, I, L, G, S, P, or T (e.g., A, P, or T); $X_4$ is A, V, I, L, or G (e.g, A or V); $X_5$ is R, K, S, T, A, V, I, or L (e.g, K, T, A, or V); $X_6$ is K, R, H, S, or T (e.g., K, R, or T); $X_7$ is N, Q, A, I, L, M, V, K, or R (e.g, Q, I, M, V, or R); and $X_8$ is E, D, S, T, R, H, or K (e.g, E, D, S, T, R, or K); or $LX_1X_2QX_3X_4$ (SEQ ID NO: 178), wherein $X_1$ is G, A, V, I, or L (e.g., G or A); $X_2$ is S, T, D, E, N, Q, P, G, V, I, L, or A (e.g., S, D, N, P, or A); $X_3$ is E, D, S, or T (e.g, E or T); and $X_4$ is G, A, V, I, or L (e.g, G or A).

In any embodiment herein, the test protein includes a sequence (e.g, a second sequence) having at least 80% sequence identity to SEQ ID NO: 180 and/or SEQ ID NO: 183:

$VTFKX_1X_2HAKX_3QX_4VX_5VLGSQEGAMX_6X_7ALX_8$ (SEQ ID NO: 180), wherein $X_1$ is S, T, N, Q, I, L, A, or V (e.g, T, N, or V); $X_2$ is A, V, I, L, G, or P (e.g, A or P); $X_3$ is K, R, or H (e.g, K or R); $X_4$ is E or D; $X_5$ is A, V, I, L, S, or T (e.g, V or T); $X_6$ is R, H, K, N, or Q (e.g, H or Q); $X_7$ is S or T; and $X_8$ is S, T, V, I, L, or A (e.g, T or A); or VTFKX$_1$X$_2$HAKX$_3$QX$_4$ (SEQ ID NO: 183), wherein $X_1$ is S, T, N, Q, I, L, A, or V (e.g, T, N, or V); $X_2$ is A, V, I, L, G or P (e.g, A or P); $X_3$ is K, R, or H (e.g, K or R); and $X_4$ is E or D.

In any embodiment herein, the test protein includes a sequence (e.g, a second sequence) having at least 80% sequence identity to SEQ ID NO: 186 and/or SEQ ID NO: 189 and/or SEQ ID NO: 190 and/or SEQ ID NO: 191:

$X_1X_2FX_3X_4X_5HX_6X_7X_8X_9X_{10}X_{11}X_{12}X_{13}LX_{14}X_{15}$ $QX_{16}X_{17}X_{18}X_{19}X_{20}X_{21}X_{22}LX_{23}$ (SEQ ID NO: 186), wherein $X_1$ is A, V, I, L, N, or Q (e.g, V, I, L, or N); $X_2$ is S, T, D, or E (e.g, T or E); $X_3$ is K, R, E, D, G, N, or Q (e.g, K, E, G, or Q); $X_4$ is S, T, N, Q, D, E, A, V, I, L, K, R, P or G (e.g, T, N, D, E, A, V, K, or P); $X_5$ is A, V, I, L, P, G, S, or T (e.g. A, P, or T); $X_6$ is A, V, I, or L (e.g, A or V); $X_7$ is K, R, S, T, A, V, I, or L (e.g, K, T, or V); $X_8$ is K, R or H; $X_9$ is N, Q, M, S, or T (e.g, Q or M); $X_{10}$ is E, D, S, or T; Xu is A, V, I, or L (e.g, V or I); $X_{12}$ is A, V, I, L, S, T, F, or Y (e.g, V, T, I, or F); $X_{13}$ is A, V, I, L, N or Q (e.g. A, V, or N); $X_{14}$ is A, V, I, L, or G (e.g, G or A); $X_{15}$ is A, V, I, L, S, T, E, D, N, Q, or G (e.g, S, D, N, or A); $X_{16}$ is D, E, S, or T (e.g., E or T); $X_{17}$ is A, V, I, L, or G (e.g., G or A); $X_{18}$ is A, V, I, L, G, E, D, S, or T (e.g., A, I, V, G, T, or E); $X_{19}$ is A, V, I, L, or M (e.g., V, L, or M); $X_{20}$ is A, V, I, L, H, K, R, Q, or N (e.g., H, Q, or L); $X_{21}$ is A, V, I, L, S, T, N, Q, K, or R (e.g., V, I, L, S, T, Q, K, or R); $X_{22}$ is A, V, I, L, S, or T (e.g., A, V, or S); and $X_{23}$ is A, V, I, L, S, or T (e.g., A or T); or $X_1X_2FX_3X_4X_5HX_6X_7X_8X_9X_{10}$ (SEQ ID NO: 189), wherein $X_1$ is A, V, I, L, N, or Q (e.g., V, I, L, or N); $X_2$ is S, T, D, or E (e.g, T or E); $X_3$ is K, R, E, D, G, N, or Q (e.g, K, E, G, or Q); $X_4$ is S, T, N, Q, D, E, A, V, I, L, K, R, P or G (e.g, T, N, D, E, A, V, K, or P); $X_5$ is A, V, I, L, P, G, S, or T (e.g., A, P, or T); $X_6$ is A, V, I, or L (e.g, A or V); $X_7$ is K, R, S, T, A, V, I, or L (e.g., K, T, or V); $X_8$ is K, R or H; $X_9$ is N, Q, M, S, or T (e.g., Q or M); and $X_{10}$ is E, D, S, or T; or $X_1HX_2X_3X_4$ (SEQ ID NO: 190), wherein $X_1$ is A, V, I, L, P, G, S, or T (e.g. A, P, or T); $X_2$ is A, V, I, or L (e.g., A or V); $X_3$ is K, R, S, T, A, V, I, or L (e.g., K, T, or V); and $X_4$ is K, R or H; or $LX_1X_2QX_3X_4$ (SEQ ID NO: 191), wherein $X_1$ is A, V, I, L, or G (e.g., G or A); $X_2$ is A, V, I, L, S, T, E, D, N, Q, or G (e.g., S, D, N, or A); $X_3$ is D, E, S, or T (e.g., E or T); and $X_4$ is A, V, I, L, or G (e.g, G or A).

In any embodiment herein, the test protein includes a sequence having at least 80% sequence identity to SEQ ID NO: 192. In some embodiments, the sequence includes an arginine at position 73, an arginine at position 99, a lysine at position 246, and/or a lysine at position 247. In other embodiments, the sequence includes a lysine at position 246 and a lysine at position 247. In other embodiments, the sequence further includes an arginine at position 99.

In any embodiment herein, the first sequence of the mutant protein includes a mutation at position 30. In other embodiments, the mutant protein includes a mutation at position 30 of the first sequence, at position 9 of the second sequence, and/or at position 10 of the second sequence.

In any embodiment herein, the mutant protein includes the sequence of a test protein (e.g., any described herein) with one or more mutations at position 73, 99, 246, and/or 247. In some embodiments, the mutation includes a glycine, alanine, valine, leucine, isoleucine, methionine, aspartic acid, glutamic acid, asparagine, or glutamine. In any embodiment herein, the mutant protein includes a mutation at positions 99, 246, and 247.

In any embodiment herein, the test protein has a sequence having at least 80% sequence identity (e.g., at least 80%, 85%, 90%, 95%, 96%, 97%, 98%, 99%, or even 100% sequence identity) to any sequence having a SEQ ID NO herein or a fragment thereof (e.g., a fragment having a sequence of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 consecutive or contiguous amino acids within any sequence having a SEQ ID NO herein).

Definitions

As used herein, the term "about" means+/−10% of any recited value. As used herein, this term modifies any recited value, range of values, or endpoints of one or more ranges.

By "alkaryl" is meant an aryl group, as defined herein, attached to the parent molecular group through an alkylene group, as defined herein. Similarly, by the term "alkheteroaryl" is meant a heteroaryl group, as defined herein, attached to the parent molecular group through an alkylene group. Other groups preceded by the prefix "alk-" are defined in the same manner. The alkaryl group can be substituted or unsubstituted. For example, the alkaryl group can be substituted with one or more substitution groups, as described herein for alkyl and/or aryl. Exemplary unsubstituted alkaryl groups are of from 7 to 16 carbons ($C_{7-16}$ alkaryl), as well as those having an alkylene group with 1 to 6 carbons and an aryl group with 4 to 18 carbons (i.e., $C_{1-6}$ alk-$C_{4-18}$ aryl).

By "alkcycloalkyl" is meant a cycloalkyl group, as defined herein, attached to the parent molecular group through an alkylene group, as defined herein. The alkcycloalkyl group can be substituted or unsubstituted. For example, the alkcycloalkyl group can be substituted with one or more substitution groups, as described herein for alkyl.

By "alkheterocyclyl" represents a heterocyclyl group, as defined herein, attached to the parent molecular group through an alkylene group, as defined herein. Exemplary unsubstituted alkheterocyclyl groups are of from 2 to 14 carbons.

By "alkoxy" is meant —OR, where R is an optionally substituted alkyl group, as described herein. Exemplary alkoxy groups include methoxy, ethoxy, butoxy, trihaloalkoxy, such as trifluoromethoxy, etc. The alkoxy group can be substituted or unsubstituted. For example, the alkoxy group can be substituted with one or more substitution groups, as described herein for alkyl. Exemplary unsubstituted alkoxy groups include $C_{1-3}$, $C_{1-6}$, $C_{1-12}$, $C_{1-16}$, $C_{1-18}$, $C_{1-20}$, or $C_{1-24}$ alkoxy groups.

By "alkyl" and the prefix "alk" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{1-6}$ alkoxy (e.g., -OAk, in which Ak is an alkyl group, as defined herein); (2) $C_{1-6}$ alkylsulfinyl (e.g., —S(O)Ak, in which Ak is an alkyl group, as defined herein); (3) $C_{1-6}$ alkylsulfonyl (e.g., —SO$_2$Ak, in which Ak is an alkyl group, as defined herein); (4) amino (e.g., —NR$^{N1}$R$^{N2}$, where each of $R^{N1}$ and $R^{N2}$ is, independently, H or optionally substituted alkyl, or $R^{N1}$ and $R^{N2}$, taken together with the nitrogen atom to which each are attached, form a heterocyclyl group); (5) aryl; (6) arylalkoxy (e.g., -OA$^L$Ar, in which A$^L$ is an alkylene group and Ar is an aryl group, as defined herein); (7) aryloyl (e.g., —C(O)Ar, in which Ar is an aryl group, as defined herein); (8) azido (e.g., an —N$_3$ group); (9) cyano (e.g., a —CN group); (10) carboxyaldehyde (e.g., a —C(O)H group); (11) $C_{3-8}$ cycloalkyl; (12) halo; (13) heterocyclyl (e.g., a 5-, 6- or 7-membered ring, unless otherwise specified, containing one, two, three, or four non-carbon heteroatoms (e.g., independently selected from the group consisting of nitrogen, oxygen, phosphorous, sulfur, or halo)); (14) heterocyclyloxy (e.g., -OHet, in which Het is a heterocyclyl group); (15) heterocyclyloyl (e.g., —C(O) Het, in which Het is a heterocyclyl group); (16) hydroxyl (e.g., a —OH group); (17) N-protected amino; (18) nitro (e.g., an —NO$_2$ group); (19) oxo (e.g., an =O group); (20) $C_{3-8}$ spirocyclyl (e.g., an alkylene diradical, both ends of which are bonded to the same carbon atom of the parent group to form a spirocyclyl group); (21) $C_{1-6}$ thioalkoxy (e.g., -SAk, in which Ak is an alkyl group, as defined herein); (22) thiol (e.g., an —SH group); (23) —CO$_2$R$^A$, where R$^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (24) —C(O)NR$^B$R$^C$, where each of R$^B$ and R$^C$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (25) —SO$_2$R$^D$, where R$^D$ is selected from the group consisting of (a) $C_{1-6}$ alkyl, (b) $C_{4-18}$ aryl, and (c) $C_{1-6}$ alk-$C_{4-18}$ aryl; (26) —SO$_2$NR$^E$R$^F$, where each of R$^E$ and R$^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; and (27) —NR$^G$R$^H$, where each of R$^G$ and R$^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group. The alkyl group can be a primary, secondary, or tertiary alkyl group substituted with one or more substituents (e.g., one or more halo or alkoxy). In some embodiments, the unsubstituted alkyl group is a $C_{1-3}$, $C_{1-6}$, $C_{1-12}$, $C_{1-16}$, $C_{1-18}$, $C_{1-20}$, or $C_{1-24}$ alkyl group.

By "alkylene" is meant a multivalent (e.g., bivalent, trivalent, tetravalent, etc.) form of an alkyl group, as described herein. Exemplary alkylene groups include methylene, ethylene, propylene, butylene, etc. In some embodiments, the alkylene group is a $C_{1-3}$, $C_{1-6}$, $C_{1-12}$, $C_{1-16}$, $C_{1-18}$, $C_{1-20}$, $C_{1-24}$, $C_{2-3}$, $C_{2-6}$, $C_{2-12}$, $C_{2-16}$, $C_{2-18}$, $C_{2-20}$, or $C_{2-24}$ alkylene group. The alkylene group can be branched or unbranched. The alkylene group can also be substituted or unsubstituted. For example, the alkylene group can be substituted with one or more substitution groups, as described herein for alkyl.

By "alkyleneoxy" is meant an alkylene group, as defined herein, attached to the parent molecular group through an oxygen atom.

By "aryl" is meant a group that contains any carbon-based aromatic group including, but not limited to, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one, two, three, four, or five substituents independently selected from the group consisting of: (1) $C_{1-6}$ alkanoyl (e.g., —C(O)Ak, in which Ak is an alkyl group, as defined herein); (2) $C_{1-6}$ alkyl; (3) $C_{1-6}$ alkoxy (e.g., -OAk, in which Ak is an alkyl group, as defined herein); (4) $C_{1-6}$ alkoxy-$C_{1-6}$ alkyl (e.g., an alkyl group, which is substituted with an alkoxy group -OAk, in which Ak is an alkyl group, as defined herein); (5) $C_{1-6}$ alkylsulfinyl (e.g., —S(O)Ak, in which Ak is an alkyl group, as defined herein); (6) $C_{1-6}$ alkylsulfinyl-$C_{1-6}$ alkyl (e.g., an alkyl group, which is substituted by an alkylsulfinyl group —S(O)Ak, in which Ak is an alkyl group, as defined herein); (7) $C_{1-6}$ alkylsulfonyl (e.g., —SO$_2$Ak, in which Ak is an alkyl group, as defined herein); (8) $C_{1-6}$ alkyl sulfonyl-$C_{1-6}$ alkyl (e.g., an alkyl group, which is substituted by an alkylsulfonyl group —SO$_2$Ak, in which Ak is an alkyl group, as defined herein); (9) aryl; (10) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (11) $C_{1-6}$ aminoalkyl (e.g., meant an alkyl group, as defined herein, substituted by an amino group); (12) heteroaryl; (13) $C_{1-6}$ alk-$C_{4-18}$ aryl (e.g., -A$^L$Ar, in which A$^L$ is an alkylene group and Ar is an aryl group, as defined herein); (14) aryloyl (e.g., —C(O)Ar, in which Ar is an aryl group, as defined herein); (15) azido (e.g., an —N$_3$ group); (16) cyano (e.g., a —CN group); (17) $C_{1-6}$ azidoalkyl (e.g., a —N$_3$ azido group attached to the parent molecular group through an alkyl group, as defined herein); (18) carboxyaldehyde (e.g., a —C(O)H group); (19) carboxyaldehyde-$C_{1-6}$ alkyl (e.g., -A$^L$C(O)H, in which A$^L$ is an alkylene group, as defined herein); (20) $C_{3-8}$ cycloalkyl; (21) $C_{1-6}$ alk-$C_{3-8}$ cycloalkyl (e.g., -A$^L$Cy, in which A$^L$ is an alkylene group and Cy is a cycloalkyl group, as defined herein); (22) halo (e.g., F, Cl, Br, or I); (23) $C_{1-6}$ haloalkyl (e.g., an alkyl group, as defined herein, substituted with one or more halo); (24) heterocyclyl; (25) heterocyclyloxy (e.g., -OHet, in which Het is a heterocyclyl group); (26) heterocyclyloyl (e.g., —C(O)Het, in which Het is a heterocyclyl group); (16) hydroxyl (e.g., a —OH group); (27) hydroxyl (e.g., a —OH group); (28) $C_{1-6}$ hydroxyalkyl (e.g., an alkyl group, as defined herein, substituted by one to three hydroxyl groups, with the proviso that no more than one hydroxyl group may be attached to a single carbon atom of the alkyl group); (29) nitro (e.g., an —NO$_2$ group); (30) $C_{1-6}$ nitroalkyl (e.g., an alkyl group, as defined herein, substituted by one to three nitro groups); (31) N-protected amino; (32) N-protected amino-$C_{1-6}$ alkyl; (33) oxo (e.g., an =O group); (34) $C_{1-6}$ thioalkoxy (e.g., -SAk, in which Ak is an alkyl group, as defined herein); (35) thio-$C_{1-6}$ alkoxy-$C_{1-6}$ alkyl (e.g., an alkyl group, which is substituted by an thioalkoxy group -SAk, in which Ak is an alkyl group, as defined herein); (36) —(CH$_2$)$_r$CO$_2$R$^A$, where r is an integer of from zero to four, and R$^A$ is selected from the group consisting of (a) hydrogen, (b) $C_{1-6}$ alkyl, (c) $G_{4-18}$ aryl, and (d) $C_{1-6}$ alk-$C_{4-18}$ aryl; (37) —(CH$_2$)$_r$CONR$^B$R$^C$, where r is an integer of from zero to four and where each R$^B$ and R$^C$ is independently selected from the group consisting of (a) hydrogen, (b) $C_{1-6}$ alkyl, (c) $G_{4-18}$ aryl, and (d) $C_{1-6}$ alk-$G_{4-18}$ aryl; (38) —(CH$_2$)$_r$SO$_2$R$^D$, where r is an integer of from zero to four and where R$^D$ is selected from the group consisting of (a) $C_{1-6}$ alkyl, (b) $G_{4-18}$ aryl, and (c) $C_{1-6}$ alk-$C_{4-18}$ aryl; (39) —(CH$_2$)$_r$SO$_2$NR$^E$R$^F$, where r is an integer of from zero to four and where each of R$^E$ and R$^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (40) —(CH$_2$)$_r$NR$^G$R$^H$, where r is an integer of from zero to four and where each of R$^G$ and R$^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group; (41) thiol; (42) perfluoroalkyl (e.g., an alkyl group, as defined herein, having each hydrogen atom substituted with a fluorine atom); (43) perfluoroalkoxy (e.g., —ORf, in which Rf is an alkyl group, as defined herein, having each hydrogen atom substituted with a fluorine atom); (44) aryloxy (e.g., —OAr, where Ar is an optionally substituted aryl group, as described herein); (45) cycloalkoxy (e.g., -OCy, in which Cy is a cycloalkyl group, as defined herein); (46) cycloalkylalkoxy (e.g., -OA$^L$Cy, in which A$^L$ is an alkylene group and Cy is a cycloalkyl group, as defined herein); and (47) arylalkoxy (e.g., -OA$^L$Ar, in which A$^L$ is an alkylene group and Ar is an aryl group, as defined herein). In particular embodiments, an unsubstituted aryl group is a $C_{4-18}$, $C_{4-14}$, $C_{4-12}$, $C_{4-10}$, $C_{6-18}$, $C_{6-14}$, $C_{6-12}$, or $C_{6-10}$ aryl group.

By "arylene" is meant a multivalent (e.g., bivalent, trivalent, tetravalent, etc.) form of an aryl group, as described herein. Exemplary arylene groups include phenylene, naphthylene, biphenylene, triphenylene, diphenyl ether, diarylene ether (e.g., —Ar—O—Ar—, where Ar is an arylene group, such as phenylene), acenaphthenylene, anthrylene, or phenanthrylene. In some embodiments, the arylene group is a $C_{4-18}$, $C_{4-14}$, $C_{4-12}$, $C_{4-10}$, $C_{6-18}$, $C_{6-14}$, $C_{6-12}$, or $C_{6-10}$ arylene group. The arylene group can be branched or unbranched. The arylene group can also be substituted or unsubstituted. For example, the arylene group can be substituted with one or more substitution groups, as described herein for aryl.

By "aryleneoxy" is meant an arylene group, as defined herein, attached to the parent molecular group through an oxygen atom.

By "carbonyl" is meant a —C(O)— group, which can also be represented as >C=O.

By "carboxyaldehyde" is meant a —C(O)H group.

By "carboxyl" is meant a —CO$_2$H group.

By "carboxylate" is meant a —CO$_2^-$ group.

By "cycloalkyl" is meant a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1.]heptyl and the like. The cycloalkyl group can also be substituted or unsubstituted. For example, the cycloalkyl group can be substituted with one or more groups including those described herein for alkyl.

By "halo" is meant F, Cl, Br, or I.

By "heteroalkyl" is meant an alkyl group, as defined herein, containing one, two, three, or four non-carbon heteroatoms (e.g., independently selected from the group consisting of nitrogen, oxygen, phosphorous, sulfur, or halo).

By "heteroalkylene" is meant a divalent form of an alkylene group, as defined herein, containing one, two, three, or four non-carbon heteroatoms (e.g., independently selected from the group consisting of nitrogen, oxygen, phosphorous, sulfur, or halo).

By "heteroalkyleneoxy" is meant a heteroalkylene group, as defined herein, attached to the parent molecular group through an oxygen atom.

By "heteroaryl" is meant a subset of heterocyclyl groups, as defined herein, which are aromatic, i.e., they contain 4n+2 pi electrons within the mono- or multicyclic ring system.

By "heterocyclyl" is meant a 5-, 6- or 7-membered ring, unless otherwise specified, containing one, two, three, or four non-carbon heteroatoms (e.g., independently selected from the group consisting of nitrogen, oxygen, phosphorous, sulfur, or halo). The 5-membered ring has zero to two double bonds and the 6- and 7-membered rings have zero to three double bonds. The term "heterocyclyl" also includes bicyclic, tricyclic and tetracyclic groups in which any of the above heterocyclic rings is fused to one, two, or three rings independently selected from the group consisting of an aryl ring, a cyclohexane ring, a cyclohexene ring, a cyclopentane ring, a cyclopentene ring, and another monocyclic heterocyclic ring, such as indolyl, quinolyl, isoquinolyl, tetrahydroquinolyl, benzofuryl, benzothienyl and the like. Heterocyclics include thiiranyl, thietanyl, tetrahydrothienyl, thianyl, thiepanyl, aziridinyl, azetidinyl, pyrrolidinyl, piperidinyl, azepanyl, pyrrolyl, pyrrolinyl, pyrazolyl, pyrazolinyl, pyrazolidinyl, imidazolyl, imidazolinyl, imidazolidinyl, pyridyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl, and the like.

By "oxo" is meant an =O group.

By "oxy" is meant an —O— group.

By "phosphonate" is meant a —P(O)(OH)(OR) group, in which R is H, optionally substituted alkyl, optionally substituted alkaryl, or optionally substituted aryl (e.g., as defined herein).

By "phosphono" is meant a —P(O)(OH)$_2$ group.

By "phosphoryl" is meant a —P(O)<group.

By "protecting group" is meant any group intended to protect a reactive group against undesirable synthetic reactions. Commonly used protecting groups are disclosed in "Greene's Protective Groups in Organic Synthesis," John Wiley & Sons, New York, 2007 (4th ed., eds. P. G. M. Wuts and T. W. Greene), which is incorporated herein by reference. O-protecting groups include an optionally substituted alkyl group (e.g., forming an ether with reactive group O), such as methyl, methoxymethyl, methylthiomethyl, benzoyloxymethyl, t-butoxymethyl, etc.; an optionally substituted alkanoyl group (e.g., forming an ester with the reactive group O), such as formyl, acetyl, chloroacetyl, fluoroacetyl (e.g., perfluoroacetyl), methoxyacetyl, pivaloyl, t-butylacetyl, phenoxyacetyl, etc.; an optionally substituted aryloyl group (e.g., forming an ester with the reactive group O), such as —C(O)—Ar, including benzoyl; an optionally substituted alkylsulfonyl group (e.g., forming an alkyl sulfonate with reactive group O), such as —SO$_2$—R$^{S1}$, where R$^{S1}$ is optionally substituted $C_{1-12}$ alkyl, such as mesyl or benzylsulfonyl; an optionally substituted arylsulfonyl group (e.g., forming an arylsulfonate with reactive group O), such as —SO$_2$—R$^{S4}$, where R$^{S4}$ is optionally substituted $C_{4-18}$ aryl, such as tosyl or phenylsulfonyl; an optionally substituted alkoxycarbonyl or aryloxycarbonyl group (e.g., forming a carbonate with reactive group O), such as —C(O)—OR$^{T1}$, where R$^{T1}$ is optionally substituted $C_{1-12}$ alkyl or optionally substituted $C_{4-18}$ aryl, such as methoxycarbonyl, methoxymethylcarbonyl, t-butyloxycarbonyl (Boc), or benzyloxycarbonyl (Cbz); or an optionally substituted silyl group (e.g., forming a silyl ether with reactive group O), such as —Si—$(R^{72})_3$, where each $R^{72}$ is, independently, optionally substituted $C_{1-12}$ alkyl or optionally substituted $C_{4-18}$ aryl, such as trimethylsilyl, t-butyldimethylsilyl, or t-butyldiphenylsilyl. N-protecting groups include, e.g., formyl, acetyl, benzoyl, pivaloyl, t-butylacetyl, alanyl, phenyl sulfonyl, benzyl, Boc, and Cbz. Such protecting groups can employ any useful agent to cleave the protecting group, thereby restoring the reactivity of the unprotected reactive group.

By "salt" is meant an ionic form of a compound or structure (e.g., any formulas, compounds, or compositions described herein), which includes a cation or anion compound to form an electrically neutral compound or structure. Salts (e.g., simple salts having binary compounds, double salts, triple salts, etc.) are well known in the art. For example, salts are described in Berge S M et al., "Pharmaceutical salts," *J. Pharm. Sci.* 1977 January; 66(1):1-19; International Union of Pure and Applied Chemistry, "Nomenclature of Inorganic Chemistry," Butterworth & Co. (Publishers) Ltd., London, England, 1971 (2nd ed.); and in "Handbook of Pharmaceutical Salts: Properties, Selection, and Use," Wiley-VCH, April 2011 (2nd rev. ed., eds. P. H. Stahl and C. G. Wermuth). The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methyl sulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine.

By "micro" is meant having at least one dimension that is less than 1 mm and, optionally, equal to or larger than about 1 μm. For instance, a microstructure (e.g., any structure described herein) can have a length, width, height, cross-sectional dimension, circumference, radius (e.g., external or internal radius), or diameter that is less than 1 mm.

By "nano" is meant having at least one dimension that is less than 1 μm but equal to or larger than about 1 nm. For instance, a nanostructure (e.g., any structure described herein, such as a nanoparticle) can have a length, width, height, cross-sectional dimension, circumference, radius (e.g., external or internal radius), or diameter that is less than 1 μm but equal to or larger than 1 nm. In other instances, the nanostructure has a dimension that is of from about 1 nm to about 1 μm.

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof.

As used herein, the terms "top," "bottom," "upper," "lower," "above," and "below" are used to provide a relative relationship between structures. The use of these terms does not indicate or require that a particular structure must be located at a particular location in the apparatus.

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones.

The term "fragment" is meant a portion of a polypeptide that is at least one amino acid shorter than the reference sequence. This portion contains, preferably, at least about 10%, 20%, 30%, 40%, 50%, 60%, 70%, 80%, or 90% of the entire length of the reference polypeptide. A fragment may contain 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein).

The term "conservative amino acid substitution" refers to the interchangeability in proteins of amino acid residues having similar side chains (e.g., of similar size, charge, and/or polarity). For example, a group of amino acids having aliphatic side chains consists of glycine (Gly or G), alanine (Ala or A), valine (Val or V), leucine (Leu or L), and isoleucine (Ile or I); a group of amino acids having aliphatic-hydroxyl side chains consists of serine (Ser or S) and threonine (Thr or T); a group of amino acids having amide containing side chains consisting of asparagine (Asn or N) and glutamine (Gin or Q); a group of amino acids having aromatic side chains consists of phenylalanine (Phe or F), tyrosine (Tyr or Y), and tryptophan (Trp or W); a group of amino acids having cyclic side chains consists of proline (Pro or P), phenylalanine, tyrosine, and tryptophan; a group of amino acids having basic side chains consists of lysine (Lys or K), arginine (Arg or R), and histidine (His or H); a group of amino acids having acidic side chains consists of glutamic acid (Glu or E) and aspartic acid (Asp or D); and a group of amino acids having sulfur containing side chains consists of cysteine (Cys or C) and methionine (Met or M). Exemplary conservative amino acid substitution groups are valine-leucine-isoleucine, phenylalanine-tyrosine, lysine-arginine, alanine-valine, glycine-serine, glutamate-aspartate, and asparagine-glutamine.

As used herein, when a polypeptide sequence is referred to as having "at least X % sequence identity" to a reference sequence, it is meant that at least X percent of the amino acids in the polypeptide are identical to those of the reference sequence when the sequences are optimally aligned. An optimal alignment of sequences can be determined in various ways that are within the skill in the art, for instance, the Smith Waterman alignment algorithm (Smith T F et al., *J. Mol. Biol.* 1981; 147:195-7) and BLAST (Basic Local Alignment Search Tool; Altschul S F et al., *J. Mol. Biol.* 1990; 215:403-10). These and other alignment algorithms are accessible using publicly available computer software such as "Best Fit" (Smith T F et al., *Adv. Appl. Math.* 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide.

By "substantial identity" or "substantially identical" is meant a polypeptide sequence that has the same polypeptide sequence, respectively, as a reference sequence, or has a specified percentage of amino acid residues that are the same at the corresponding location within a reference sequence when the two sequences are optimally aligned. For example, an amino acid sequence that is "substantially identical" to a reference sequence has at least about 50%, 60%, 70%, 75%, 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

The present invention can relate to a chimeric sequence of any polypeptide(s) described herein. The term "chimeric" as used herein as applied to a polypeptide refers to two components that are defined by structures derived from different sources. For example, where "chimeric" is used in the context of a chimeric polypeptide (e.g., a chimeric protein), the chimeric polypeptide includes amino acid sequences that are derived from different polypeptides. A chimeric polypeptide may comprise either modified or naturally-occurring polypeptide sequences.

The term "chimeric polypeptide" refers to a polypeptide which is made by the combination (i.e., "fusion") of two otherwise separated segments of amino sequence, usually through human intervention. A polypeptide that comprises a chimeric amino acid sequence is a chimeric polypeptide. Some chimeric polypeptides can be referred to as "fusion variants."

A "host cell," as used herein, denotes an in vivo or in vitro eukaryotic cell (e.g., a mammalian cell), a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject eukaryotic host cell is a genetically modified eukaryotic host cell (e.g., a mammalian germ cell), by virtue of introduction into a suitable eukaryotic host cell of an exogenous nucleic acid.

By "linker" is meant any useful multivalent (e.g., bivalent) component useful for joining to different portions or segments. Exemplary linkers include a nucleic acid sequence, a chemical linker, etc. Further exemplary linkers are described herein.

By "pharmaceutically acceptable salt" is meant a salt that is, within the scope of sound medical judgment, suitable for use in contact with the tissues of humans and animals without undue toxicity, irritation, allergic response and the like and are commensurate with a reasonable benefit/risk ratio.

By "pharmaceutically acceptable excipient" is meant any ingredient other than a compound or structure (e.g., any formulas, compounds, or compositions described herein) and having the properties of being nontoxic and non-inflammatory in a subject. Exemplary, non-limiting excipients include adjuvants, antiadherents, antioxidants, binders, carriers, coatings, compression aids, diluents, disintegrants, dispersing agents, dyes (colors), emollients, emulsifiers, fillers (diluents), film formers or coatings, flavors, fragrances, glidants (flow enhancers), isotonic carriers, lubricants, preservatives, printing inks, solvents, sorbents, stabilizers, suspending or dispersing agents, surfactants, sweeteners, waters of hydration, or wetting agents. Any of the excipients can be selected from those approved, for example, by the United States Food and Drug Administration or other governmental agency as being acceptable for use in humans or domestic animals. Exemplary excipients include, but are not limited to alcohol, butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, glycerol, hydroxypropyl cellulose, hydroxypropyl methylcellulose, lactated Ringer's solution, lactose, magnesium stearate, maltitol, maltose, mannitol, methionine, methylcellulose, methyl paraben, microcrystalline cellulose, polyethylene glycol, polyol, polyvinyl pyrrolidone, povidone, pregelatinized starch, propyl paraben, retinyl palmitate, Ringer's solution, shellac, silicon dioxide, sodium carboxymethyl cellulose, sodium chloride injection, sodium citrate, sodium starch glycolate, sorbitol, starch (corn), stearic acid, stearic acid, sucrose, talc, titanium dioxide, vegetable oil, vitamin A, vitamin E, vitamin C, water, and xylitol.

By "isomer" is meant a molecule having the same molecular formula as the reference molecule. Exemplary isomers include stereoisomers, diastereomers, enantiomers, geometric isomers, tautomers, as well as mixtures thereof.

By an "effective amount" or a "sufficient amount" of an agent, as used herein, is that amount sufficient to effect beneficial or desired results, such as clinical results, and, as such, an "effective amount" depends upon the context in which it is being applied. For example, in the context of administering an agent that is an inhibitor (e.g., any described herein), an effective amount of an agent is, for example, an amount sufficient to achieve a reduction in viral activity, as compared to the response obtained without administration of the agent.

By "subject" is meant a human or non-human animal (e.g., a mammal).

By "treating" a disease, disorder, or condition in a subject is meant reducing at least one symptom of the disease, disorder, or condition by administrating a therapeutic agent to the subject. By "treating prophylactically" a disease, disorder, or condition in a subject is meant reducing the frequency of occurrence of or reducing the severity of a disease, disorder or condition by administering a therapeutic agent to the subject prior to the onset of disease symptoms. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable.

Other features and advantages of the invention will be apparent from the following description and the claims.

BRIEF DESCRIPTION OF THE DRAWINGS

FIG. 3A-3F shows molecular dynamics simulation data of the TT. Provided are (A) an image of the structure of the tip of the TT showing the location of all lysine (Lys) and arginine (Arg) residues; (B) characterization of hydrogen bonding between Lys residues near the fusion loop (FL) of truncated E trimers and neighboring lipids for the 1-palmitoyl-2-oleoyl-sn-glycero-3-phosphocholine:1-palmitoyl-2-oleoyl-sn-glycero-3-phosphoethanolamine:cholesterol (PC:PE:CHOL) and 1-palmitoyl-2-oleoyl-sn-glycero-3-phosphocholine:1-palmitoyl-2-oleoyl-sn-glycero-3-phospho-rac-glycerol (PC:PG) systems, in which characterization is provided for two different truncated E trimer structures: a first TT (T1) and a second TT (T2) placed on one side of a lipid membrane; and (C) common hydrogen-bonding configurations of Lys to the phosphate and ester oxygens in the lipid headgroups. Also provided are characterization of hydrogen bonding between positively-charged residues (K246, K247, R73, R99) near the FL of truncated E trimers (T1 and T2) and neighboring lipids for the (D) 1-palmitoyl-2-oleoyl-sn-glycero-3-phosphocholine:1-palmitoyl-2-oleoyl-sn-glycero-3-phosphoethanolamine (PC:PE) system, (E) PC:PE:CHOL system, and (F) PC:PG system.

FIG. 5 shows alignment of exemplary flavivirus sequences (SEQ ID NOs:1-34) showing the conservation of positively-charged residues R73, R99, K246, and K247, which can form hydrogen bonds with phosphate oxygens of the lipid headgroups.

FIG. 6A-6B shows alignment of exemplary flavivirus sequences in a domain II region of the envelope (E) protein (SEQ ID NOs:35-104) and exemplary consensus sequences (SEQ ID NOs:105-106).

FIG. 7A-7B shows alignment of exemplary flavivirus sequences in another domain II region of the E protein (SEQ ID NOs: 107-176) and exemplary consensus sequences (SEQ ID NOs: 177-178).

FIG. 8 shows alignment of exemplary Dengue virus strain sequences in a domain II region of the E protein and exemplary consensus sequences (SEQ ID NOs: 179-184).

FIG. 9 shows alignment of exemplary flavivirus sequences in two different portions of the domain II regions of the E protein and exemplary consensus sequences (SEQ ID NOs: 185-191).

FIG. 10 shows the amino acid sequence for the E protein of Dengue virus type 2 (strain Thailand/NGS-C/1944) (UniprotKB Acc. No. P14340, position 281-775) (SEQ ID NO: 192) and various domains of the protein, including domain I (red), domain II (yellow), domain III (dark blue), stem region (light blue), and transmembrane region (gray) (SEQ ID NO: 192). Provided are positions of R73, R99, K246, K247, and the fusion loop (position 98-111).

FIG. 11A-11B shows structures of exemplary inhibitors, including (A) exemplary lysine inhibitors and (B) exemplary arginine inhibitors.

DETAILED DESCRIPTION OF THE INVENTION

Figure 1:
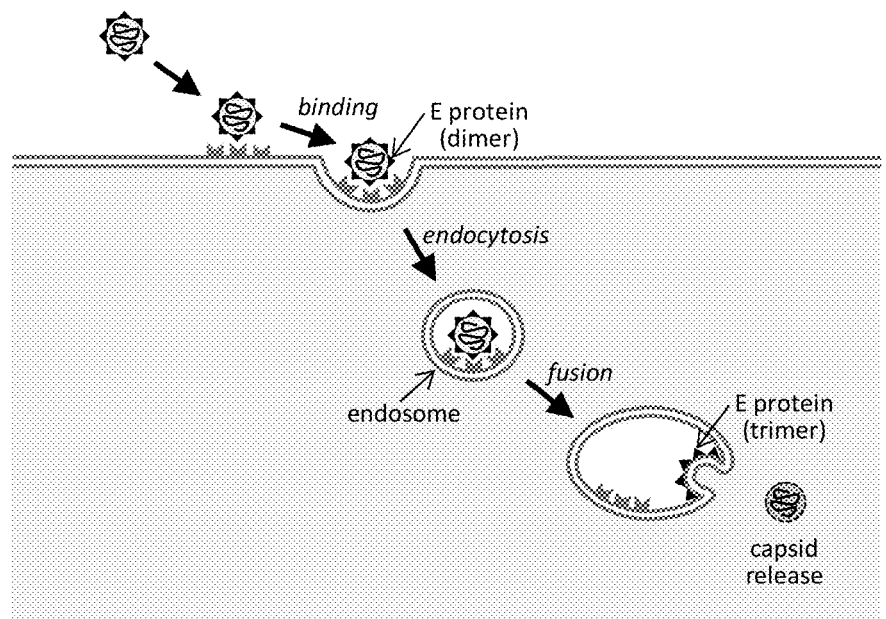
FIG. 1 shows an exemplary schematic of viral entry by a Dengue virus. Provided are the steps of viral entry, including approach of the Dengue virus to a host cell, binding of the virus (e.g., by way of the E protein dimer) to one or more cellular receptors, endocytosis of the virus into an endosome, fusion of the viral cell wall to the endosome (e.g., triggered by low pH, in which fusion occurs by way of the E protein trimer), and release of the capsid including the viral nucleic acid into the cytoplasm of the host cell.

We have identified several amino acids within a viral envelope protein that contribute to disruption of a lipid layer. In part, one or more of the amino acids (e.g., R73, R99, K246, and/or K247, in reference to the sequence of the E protein, such as SEQ ID NO: 192 or in reference to a polypeptide sequence that is optimally aligned to SEQ ID NO: 192 as the reference sequence) participate in hydrogen bonding to a lipid headgroup, which in turn results in deformation of a lipid layer. This interaction between the E protein and the lipid layer may contribute to fusion of the viral membrane to a host's endosome, in which fusion is a typically required prior to release of the viral capsid into the host's cytoplasm. Thus, these amino acid(s) could be useful targets for developing therapeutic agents that can inhibit viral fusion. Accordingly, the present invention relates, in part, to a method for identifying a candidate therapeutic for a disease caused by a viral envelope protein. In another aspect, the present invention relates, in part, to a method of treating a viral infection in a subject. Additional details follow.

Methods of Identifying a Candidate Therapeutic

The present invention relates to methods for identifying a candidate therapeutic for a disease caused by a viral envelope protein. In particular embodiments, the viral envelope protein includes one or more protein sequences or polypeptide sequences described herein (e.g., one or more of SEQ ID NOs:35-192). In another embodiment, the viral envelope protein includes one or more of R73, R99, K246, and/or K247, in reference to the sequence of the E protein, such as SEQ ID NO: 192 or in reference to a polypeptide sequence that is optimally aligned to SEQ ID NO: 192 as the reference sequence.

In some embodiments, the method includes contacting a viral envelope protein (e.g., any described herein) with the compound (e.g., a candidate therapeutic or any described herein) and determining an activity of the compound with the protein. Activity can include any useful biochemical, chemical, biological, pharmacodynamic, and/or pharmacokinetic assay to determine whether or not the compound provides a decrease or increase in biological effect of the viral protein. In particular embodiment, the biological effect means inhibiting the viral protein from fusion with a lipid layer, as compared to a control. In another embodiment, the biological effect means reducing the efficacy of the viral protein from fusion with a lipid layer, as compared to a control. In yet another embodiment, the biological effect means reduced hydrogen bonding between the viral protein and a lipid layer, as compared to a control. Exemplary activity can include determining binding (e.g., between the compound and a lipid layer, including competitive assays, binding assays, etc.), inhibition (e.g., inhibitory activity, such as determined by $IC_{50}$ values, as well as other methods of determining an activity of inhibitors, as described herein), and/or infection (e.g., infection and/or replication activity, as determined by cellular assays to measure cellular infection or replication, including a cytopathic viral assay, a viral replicon assay, a phenotypic assay, or a gene-targeted viral assay).

Additional activity parameters, as well as assays to measure such activity, as described in Green N et al., "Cell-based assays to identify inhibitors of viral disease," *Expert Opin Drug Discov.* 2008; 3:671-676; Everts M et al., "Accelerating drug development: antiviral therapies for emerging viruses as a model," *Annu. Rev. Pharmacol. Toxicol.* 2017; 57:155-169; Zaitseva E et al., "Dengue virus ensures its fusion in late endosomes using compartment-specific lipids," *PLoS Pathogens* 2010; 6:e1001131 (14 pp.); and Leyssen P et al., "Perspectives for the treatment of infections with Flaviviridae," *Clin. Microbiol. Rev.* 2000; 13:67-82, each of which is incorporated herein by reference in its entirety.

In some embodiments, the method can further include comparing the activity of the compound with the test protein to a control. In other embodiments, the control includes determining an activity with a mutant protein, and the activity of the test protein indicates greater inhibition, as compared to the mutant protein. In yet other embodiments, the activity of the test protein indicates greater inhibition of viral entry, as compared to the control.

Any useful control can be employed in determining an activity. An exemplary, non-limiting control includes activity of a protein without exposure to the compound. In this mode, activity of the test protein in the presence of the compound can be compared to activity of the test protein in the absence of the compound. Activity parameters can include determining viral infection and/or replication activity in the presence and absence of the compound. Another activity parameters can include determining binding of the protein to a lipid layer (e.g., in a planar lipid layer or in a liposome) in the presence and absence of the compound. Yet other activity parameters can include determining fusogenic activity of the protein, which can be tested by the extent of liposome fusion with the protein and in the presence and absence of the compound.

Another exemplary, non-limiting control includes activity of mutant protein in the presence of the compound. In this mode, the mutant protein can include one or more modifications that would diminish hydrogen bonding between the protein and the lipid layer (e.g., a modification to one or more of R73, R99, K246, and/or K247, in reference to the sequence of the E protein, such as SEQ ID NO: 192 or in reference to a polypeptide sequence that is optimally aligned to SEQ ID NO: 192 as the reference sequence; or a modification to K9 and/or K10, in reference to a second sequence, as described herein, or in reference to a polypeptide sequence that is optimally aligned to one or SEQ ID NOs: 107-176; or a modification to R30, in reference to a first sequence, as described herein, or in reference to a polypeptide sequence that is optimally aligned to one or SEQ ID NOs:35-104). Such modifications can include replacing the arginine (Arg or R) or lysine (Lys K) residue with an amino acid having reduced hydrogen bonding capability, such as a hydrophobic residue, a nucleophilic residue, a small residue, an aromatic residue, an acidic residue, or an amide residue (e.g., glycine (Gly or G), alanine (Ala or A), serine (Ser or S), threonine (Thr or T), cysteine (Cys or C), valine (Val or V), leucine (Leu or L), isoleucine (Ile or I), methionine (Met or M), aspartic acid (Asp or D), glutamic acid (Glu or E), asparagine (Asn or N), or glutamine (Gin or Q)). In some embodiments, the modification includes replacing R or K with G, A, D, or E. Activity parameters can include determining binding in the presence of the protein or in the presence of the mutant protein.

A lipid layer can include any useful composition include one or more lipid compounds and/or components (e.g., sterols) that emulate one or more physical or chemical characteristics (e.g., lipid composition, fluidity, curvature, charge, etc.) of a host lipid layer (e.g., a lipid layer of the host's endosome or host's cell membrane).

Exemplary combinations of lipids include one or more PE (e.g., any described herein) with one or more PS (e.g., any described herein); one or more SM (e.g., any described herein) with cholesterol; one or more PC (e.g., any described herein) with one or more PE (e.g., any described herein) and optionally including one or more sterols; one or more PC (e.g., any described herein) with one or more PG (e.g., any described herein); PC, PE, PI, and BMP (e.g., any of these described herein); one or more PC (e.g., any described herein) with one or more PG (e.g., any described herein); and combinations thereof.

The lipid layer can include any useful lipids and/or lipid-related components, including a phosphocholine (PC), such as 1-palmitoyl-2-oleoyl-sn-glycero-3-phosphocholine (POPC), 1,2-dioleoyl-sn-gly cero-3-phosphocholine (DOPC), 1,2-dipalmitoyl-sn-glycero-3-phosphocholine (DPPC), 1,2-distearoyl-sn-glycero-3-phosphocholine (DSPC), 1,2-dilauroyl-sn-glycero-3-phosphocholine (DLPC), 1,2-dimyristoyl-sn-glycero-3-phosphocholine (DMPC), 1-stearoyl-2-oleoyl-sn-glycero-3-phosphocholine (SOPC), 1-oleoyl-2-[12-[(7-nitro-2-1,3-benzoxadiazol-4-yl)amino]lauroyl]-sn-glycero-3-phosphocholine (18:1-12:0

NBD PC), and 1-palmitoyl-2-{12-[(7-nitro-2-1,3-benzoxadiazol-4-yl)amino]lauroyl}-sn-glycero-3-phosphocholine (16:0-12:0 NBD PC); a phosphatidylethanolamine (PE), such as 1-palmitoyl-2-oleoyl-sn-gly cero-3-phosphoethanolamine (POPE), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), and 1,2-dipalmitoyl-sn-glycero-3-phosphoethanolamine-N-[methoxy(polyethylene glycol)-2000] (16:0 PEG-2000 PE); a phosphatidylserine (PS), such as 1,2-dipalmitoyl-sn-glycero-3-[phosphor-L-serine] (POPS) and 1,2-dioleoyl-sn-glycero-3-[phosphor-L-serine] (DOPS); a phosphoglycerol (PG), such as 1-palmitoyl-2-oleoyl-sn-glycero-3-phospho-rac-glycerol (POPG), and 1,2-dioleoyl-sn-glycero-3-phospho-(1'-rac-glycerol) (DOPG); an ammonium lipid, such as 1,2-dioleoyl-3-trimethylammonium-propane (18:1 DOTAP); a sterol, such as cholesterol, desmosterol, stigmasterol, sitosterol, a cholesteryl ester, glucosyl stigmasterol, and glucosyl sitosterol; a sphingomyelin (SM), such as N-acyl-sphing-4-enine-1-phosphocholine, N-oleoyl-D-erythro-sphingosylphosphorylcholine (18:1 SM), N-stearoyl-D-erythro-sphingosyl phosphorylcholine (18:0 SM), N-lauroyl-D-erythro-sphingosylphosphorylcholine (12:0 SM), N-myristoyl-D-erythro-sphingosylphosphorylcholine (14:0 SM), N-palmitoyl-D-erythro-sphingosylphosphorylcholine (16:0 SM), N-palmitoleoyl-D-erythro-sphingosyl phosphorylcholine (16:1 SM), and N-heptadecanoyl-D-erythro-sphingosylphosphorylcholine (17:0 SM); a bis(monoacylglycero) phosphate (BMP), such as bis(monooleoylglycero) phosphate, bis(monomyristoylglycero)phosphate, sn-(3-myristoyl-2-hydroxy)-glycerol-1-phospho-sn-3'-(1',2'-dimyristoyl)-glycerol, sn-[2,3-dioleoyl]-glycerol-1-phospho-sn-1'-[2,3-dioleoyl]-glycerol, sn-(1-oleoyl-2-hydroxy)-glycerol-3-phospho-sn-3'-(1'-oleoyl-2'-hydroxy)-glycerol, sn-(3-oleoyl-2-hydroxy)-glycerol-1-phospho-sn-3'-(1',2'-dioleoyl)-glycerol, sn-(3-oleoyl-2-hydroxy)-glycerol-1-phospho-sn-1'-(3-oleoyl-2-hydroxy)-glycerol, as well as isomers thereof (e.g., S and/or R isomers) and/or salts thereof; and a phosphatidylinositol (PI), including 1,2-diacyl-sn-glycero-3-phospho-(1-D-myo-inositol), L-α-phosphatidylinositol (from soy), 1,2-dipalmitoyl-sn-glycero-3-phospho-(1'-myo-inositol) (16:0 PI), 1-palmitoyl-2-oleoyl-sn-glycero-3-phosphoinositol (16:0-18:1 PI), 1,2-distearoyl-sn-glycero-3-phosphoinositol (18:0 PI), 1,2-dioleoyl-sn-glycero-3-phospho-(1'-myo-inositol) (18:1 PI), 1,2-dioleoyl-ST7-glycero-3-phospho-(1'-myo-inositol-3'-phosphate) (18:1 PI(3)P), and 1-palmitoyl-2-oleoyl-sn-glycero-3-phospho-(1'-myo-inositol-4'-phosphate) (16:0-18:1 PI(4)P), including salts thereof, as well as combinations thereof. Additional lipids and lipid components are readily available commercially from Avanti Polar Lipids, Inc. (Alabaster, Ala., USA).

Any useful compound or candidate therapeutic can be tested. Exemplary, non-limiting candidate therapeutics include any described (e.g., a lysine inhibitor and/or arginine inhibitor, as well as combinations thereof).

Methods of Treating an Infection

The present invention also relates to methods of treating a viral infection in a subject. In some embodiment, the viral infection is caused, at least in part, by a viral envelope protein. In another embodiment, the viral infection is exacerbated, at least in part, by entry of the viral envelope protein into a host cell. In yet another embodiment, the viral infection is exacerbated, at least in part, by fusion of the viral envelope protein to a lipid membrane of a host cell (e.g., a cellular membrane or an endosomal membrane). In particular embodiments, the viral envelope protein includes one or more protein sequences or polypeptide sequences described herein (e.g., one or more of SEQ ID NOs:35-192). In another embodiment, the viral envelope protein includes one or more of R73, R99, K246, and/or K247, in reference to the sequence of the E protein, such as SEQ ID NO: 192 or in reference to a polypeptide sequence that is optimally aligned to SEQ ID NO: 192 as the reference sequence.

The viral infection can be caused by a virus characterized by a viral envelope protein (e.g., including one or more protein sequences or polypeptide sequence described herein). In particular embodiments, the viral infection is caused by a flavivirus (e.g., a mosquito-borne flavivirus). Additional flaviviruses are described herein.

Proteins and Polypeptide Sequences

The methods herein employ an envelope protein, as described herein, which can be employed as a target protein for identifying a candidate therapeutic or can be the protein intended to be targeted for a method of treatment. The envelope protein can be characterized in any useful manner. In one non-limiting instance, the envelope protein includes a sequence having at least 80% sequence identity (e.g., at least about 85%, 90%, 95%, 96%, 97%, 98%, or 99% sequence identity) to SEQ ID NO: 192 (see, e.g., FIG. 10), where the sequence includes an arginine at position 73, an arginine at position 99, a lysine at position 246, and/or a lysine at position 247, e.g., in reference to a polypeptide sequence that is optimally aligned to SEQ ID NO: 192 as the reference sequence.

In another non-limiting instance, the envelope protein includes a first sequence, as described herein (see, e.g., FIG. 6A-6B, 8, or 9). In some embodiments, the first sequence has at least 80% sequence identity (e.g., at least about 85%, 90%, 95%, 96%, 97%, 98%, or 99% sequence identity) to any one of SEQ ID NOs:35-104 (e.g., having one or more conservative amino acid substitutions for one or more amino acids in any of positions 1 to 31). In yet other embodiments, the first sequence includes or is any one of SEQ ID NOs:105, 106, 179, 181, 182, 185, 187, and 188.

FIG. 6A-6B provides exemplary regions of a viral envelope protein (e.g., a first sequence of a viral envelope protein) for various flaviviruses (see, e.g., SEQ ID NOs:35-104, including any of these having one or more conservative amino acid substitutions for one or more amino acids in any of positions 1 to 31). These regions can include an arginine at position 30 and an optional arginine at position 4, in which the position is determined in reference to a polypeptide sequence that is optimally aligned to one or more of SEQ ID NOs:35-104 as the reference sequence. A skilled artisan would understand how to determine such an optimal alignment.

In some embodiments, the first sequence includes a consensus sequence, such as the following:

(SEQ ID NO: 105)

$CX_2X_3X_4X_5X_6X_7RG$, in which $X_2$ can be K or R; $X_3$ can be H, K, Q, R, or S; $X_4$ can be D, G, L, S, or T; $X_5$ can be F, L, M, Q, V, or Y; $X_6$ can be S, T, or V; and $X_7$ can be D or N.

In other embodiments, the first sequence includes a consensus sequence, such as the following:

(SEQ ID NO: 106)

$X_1X_2X_3X_4CP$, in which $X_1$ can be A, I, S, T, or V; $X_2$ can be A, D, E, K, N, Q, R, S, T, or V; $X_3$ can be A, D, G, S, or T; and $X_4$ can be A, K, N, or R.

In yet other embodiments, the first sequence includes a consensus sequence, such as the following:

$$TX_2X_3RCPX_7X_8GEX_{11}X_{12}LX_{14}EEQDX_{19}X_{20}X_{21}X_{22}CX_{24}X_{25}X_{26}X_{27}VDRG, \quad \text{(SEQ ID NO: 179)}$$

in which $X_2$ can be A, D, or E; $X_3$ can be S or T; $X_7$ can be I or T; $X_8$ can be L or Q; $X_{11}$ can be A or P; $X_{12}$ can be I, S, T, V, or Y; $X_{14}$ can be K, N, P, or V; $X_{19}$ can be A, K, Q, or T; $X_{20}$ can be N, Q, or R; $X_{21}$ can be F, L or Y; $X_{22}$ can be L, I, or V; $X_{24}$ can be K or R; $X_{25}$ can be H or R; $X_{26}$ can be D, S, or T; and $X_{27}$ can be F, M, V, or Y.

In some embodiments, the first sequence includes a consensus sequence, such as the following:

$$CX_2X_3X_4X_5VDRG, \quad \text{(SEQ ID NO: 181)}$$

in which $X_2$ can be K or R; $X_3$ can be H or R; $X_4$ can be D, S, or T; and $X_5$ can be F, M, V, or Y.

In other embodiments, the first sequence includes a consensus sequence, such as the following:

$$TX_2X_3RCP, \quad \text{(SEQ ID NO: 182)}$$

in which $X_2$ can be A, D, or E; and $X_3$ can be S or T.

In some embodiments, the first sequence includes a consensus sequence, such as the following:
$X_1X_2X_3X_4CPX_7X_8X_9X_{10}X_{11}X_{12}X_{13}X_{14}X_{15}X_{16}X_{17}X_{18}X_{19}X_{20}X_{21}X_{22}CX_{24}X_{25}X_{26}X_{27}X_{28}X_{29}RG$ (SEQ ID NO: 185), in which $X_1$ can be I, S, T, or V; $X_2$ can be A, D, E, K, R, S, or V; $X_3$ can be A, S, or T; $X_4$ can be A, N, or R; $X_7$ can be A, I, or T; $X_8$ can be L, M, Q, T, or V; $X_9$ can be G or Q; $X_{10}$ can be E, L, or P; $X_{11}$ can be A, P, S, or T; $X_{12}$ can be A, E, H, I, S, T, V, or Y; $X_{13}$ can be L or N; $X_{14}$ can be A, D, E, K, N, P, S, T, or V; $X_{15}$ can be E or K; $X_{16}$ can be A, E, Q, R, or S; $X_{17}$ can be A, H, Q, L, R, S, or T; $X_{18}$ can be D, E, or Q; $X_{19}$ can be A, D, G, H, I, K, P, Q, S, or T; $X_{20}$ can be A, G, N, Q, R, S, or T; $X_{21}$ can be F, L, M, T, or Y; $X_{22}$ can be I, L, or V; $X_{24}$ can be K or R; $X_{25}$ can be H, K, Q, R, or S; $X_{26}$ can be D, G, S, or T; $X_{27}$ can be F, L, M, Q, V, or Y; $X_{28}$ can be S, T, or V; and $X_{29}$ can be D or N.

In other embodiments, the first sequence includes a consensus sequence, such as the following:

$$CX_2X_3X_4X_5X_6X_7RG, \quad \text{(SEQ ID NO: 187)}$$

in which $X_2$ can be K or R; $X_3$ can be H, K, Q, R, or S; $X_4$ can be D, G, S, or T; $X_5$ can be F, L, M, Q, V, or Y; $X_6$ can be S, T, or V; and $X_7$ can be D or N.

In yet other embodiments, the first sequence includes a consensus sequence, such as the following:

$$X_1X_2X_3RCP, \quad \text{(SEQ ID NO: 188)}$$

in which $X_1$ can be I, S, T, or V; $X_2$ can be A, D, E, K, R, S, or V; and $X_3$ can be A, S, or T.

In another non-limiting instance, the envelope protein includes a second sequence, as described herein (see, e.g., FIG. 7A-7B, 8, or 9). In some embodiments, the second sequence has at least 80% sequence identity (e.g., at least about 85%, 90%, 95%, 96%, 97%, 98%, or 99% sequence identity) to any one of SEQ ID NOs: 107-176 (e.g., having one or more conservative amino acid substitutions for one or more amino acids in any of positions 1 to 28). In other embodiments, the second sequence includes or is any one of SEQ ID NOs: 177, 178, 180, 183, 184, 186, and 189-191.

FIG. 7A-7B provides exemplary regions of a viral envelope protein (e.g., a first sequence of a viral envelope protein) for various flaviviruses (see, e.g., SEQ ID NOs: 107-176, including any of these having one or more conservative amino acid substitutions for one or more amino acids in any of positions 1 to 28). In some embodiments, these regions can include a lysine at position 9 and/or a lysine or an arginine at position 10, in which the position is determined in reference to a polypeptide sequence that is optimally aligned to one or more of SEQ ID NOs: 107-176 as the reference sequence. A skilled artisan would understand how to determine such an optimal alignment.

In some embodiments, the second sequence includes a consensus sequence, such as the following:

$$FX_2X_3X_4HX_6X_7X_8X_9X_{10}, \quad \text{(SEQ ID NO: 177)}$$

in which $X_2$ can be E, G, K, Q, or T; $X_3$ can be A, D, E, K, N, P, T, or V; $X_4$ can be A, P, or T; $X_6$ can be A or V; $X_7$ can be A, K, T, or V; $X^8$ can be K, R, or T; $X_9$ can be I, M, Q, R, or V; and $X_{10}$ can be D, E, K, R, S, or T.

In other embodiments, the second sequence includes a consensus sequence, such as the following:

$$LX_2X_3QX_5X_6, \quad \text{(SEQ ID NO: 178)}$$

in which $X_2$ can be A or G; $X_3$ can be A, D, N, P, or S; $X_5$ can be E or T; and $X_6$ can be A or G.

In yet other embodiments, the second sequence includes a consensus sequence, such as the following:

$$VTFKX_5X_6HAKX_{10}QX_{12}VX_{14}VLGSQEGAMX_{24}X_{25}ALX_{28}, \quad \text{(SEQ ID NO: 180)}$$

in which $X_5$ can be N, T, or V; $X_6$ can be A or P; $X_{10}$ can be K or R; $X_{12}$ can be D or E; $X_{14}$ can be T or V; $X_{24}$ can be H or Q; $X_{25}$ can be S or T; and $X_{28}$ can be A or T.

In some embodiments, the first sequence includes a consensus sequence, such as the following:

$$VTFKX_5X_6HAKX_{10}QX_{12}, \quad \text{(SEQ ID NO: 183)}$$

in which $X_5$ can be N, T, or V; $X_6$ can be A or P; $X_{10}$ can be K or R; and $X_{12}$ can be D or E.

In other embodiments, the first sequence includes a consensus sequence, such as the following:

$$LGSQEG. \quad \text{(SEQ ID NO: 184)}$$

In some embodiments, the second sequence includes a consensus sequence, such as the following:
$X_1X_2FX_4X_5X_6HX_8X_9X_{10}X_{11}X_{12}X_{13}X_{14}X_{15}LX_{17}X_{18}QX_{20}X_{21}X_{22}X_{23}X_{24}X_{25}X_{26}LX_{28}$ (SEQ ID NO: 186), in which $X_1$ can be I, L, M, or V; $X_2$ can be E or T; $X_4$ can be E, G, K, or Q; $X_5$ can be A, D, E, K, N, P, T, or V; $X_6$ can be A, P, or T; $X_8$ can be A or V; $X_9$ can be K, T, or V; $X_{10}$ can be K or R; $X_{11}$ can be M, Q, or R; $X_{12}$ can be D, E, S, or T; $X_{13}$ can be I or V; $X_{14}$ can be F, I, L, T, V, or Y; $X_{15}$ can be A, N, or V; $X_{17}$ can be A or G; $X_{18}$ can be A, D, N, or S; $X_{20}$ can be E or T; $X_{21}$ can be A or G; $X_{22}$ can be A, E, G, I, T, or V; $X_{23}$ can be L, M, or V; $X_{24}$ can be H, L, or Q; $X_{25}$ can be I, K, Q, R, S, T, or V; $X_{26}$ can be A, S, or V; and $X_{28}$ can be A or T.

In other embodiments, the second sequence includes a consensus sequence, such as the following:

$X_1X_2FX_4X_5X_6HX_8X_9X_{10}X_{11}X_{12}$, (SEQ ID NO: 189)

in which $X_1$ can be I, L, M, or V; $X_2$ can be E or T; $X_4$ can be E, G, K, or Q; $X_5$ can be A, D, E, K, N, P, T, or V; $X_6$ can be A, P, or T; $X_8$ can be A or V; $X_9$ can be K, T, or V; $X_{10}$ can be K or R; $X_{11}$ can be M, Q, or R; and $X_{12}$ can be D, E, S, or T.

In yet other embodiments, the second sequence includes a consensus sequence, such as the following:

$X_1HX_3X_4X_5$, (SEQ ID NO: 190)

in which $X_1$ can be A, P, or T; $X_3$ can be A or V; $X_4$ can be K, T, or V; and $X_5$ can be K or R.

In other embodiments, the second sequence includes a consensus sequence, such as the following:

$LX_2X_3QX_5X_6$, (SEQ ID NO: 191)

in which $X_2$ can be A or G; $X_3$ can be A, D, N, or S; $X_5$ can be E or T; and $X_6$ can be A or G.

Any envelope protein can include a first sequence (e.g., any described herein), a second sequence (e.g., any described herein), or a combination of a first sequence and a second sequence (e.g., any first and second sequences described herein). FIG. 8 provides exemplary combinations of first and second sequences that may be present in a viral envelope protein (e.g., a combination of SEQ ID NOs: 179 and 180; or a combination of SEQ ID NOs: 181 or 182 with one of SEQ ID NOs: 183 or 184). FIG. 9 provides further exemplary combinations of first and second sequences that may be present in a viral envelope protein (e.g., a combination of SEQ ID NOs: 185 and 186; or a combination of SEQ ID NOs: 187 or 188 with one of SEQ ID NOs: 189-191).

Lysine and Arginine Inhibitors

The present invention relates, in part, to use of one or more inhibitors (e.g., any described herein). Such inhibitors can bind (e.g., through one or more covalent or non-covalent bonds) to any useful portion (e.g., one or more amino acid residues, such as arginine or lysine) of a virus (e.g., any virus herein). In particular embodiments, the portion is in proximity to tip region of a viral envelope protein, in which the tip region interfaces with a potential host cell.

Exemplary, non-limiting inhibitors (e.g., lysine inhibitors) include manoalide; seco-manoalide; wortmannin; an aldehyde terpenoid (see, e.g., 3-(E)-methoxycarbonyl-2,4,6-trienal; methyl (E,E)-4-oxo-2-[(2,6,6-trimethylcyclohex-1-enyl)vinyl]but-2-enoate; methyl (E,E)-4-oxo-2-[(2-methyl-1-propenyl)vinyl]but-2-enoate; methyl (E,E,E)-4-oxo-2-[(2,6-dimethyl-1,5-heptadienyl)vinyl]but-2-enoate; methyl (E,E)-4-oxo-2-[(2,5,5,8a-tetramethyl-trans-3,4,4a,5,6,7,8,8a-octahydronaphthyl)vinyl]but-2-enoate; or salts thereof); a wortmannin analogue (see, e.g., sonolisib (PX-866, [(3aR,6E,9S,9aR,10R,11aS)-6-[[bis(prop-2-enyl)amino]methylidene]-5-hydroxy-9-(methoxymethyl)-9a,11a-dimethyl-1,4,7-tri oxo-2,3,3a,9,10,11-hexahydroindeno[4,5-h]isochromen-10-yl] acetate) or salts thereof); carbaglucose-6-phosphate; myriocin; 4-[(1,1-dioxo-1,2-benzothiazol-3-yl)sulfanyl]benzoic acid; a pyrrole-5-carboxaldehyde inhibitor (e.g., 2,4-ethyl-3-methyl-5-formyl-1H-pyrrole-2,4-dicarboxylate; 2,4-ethyl-3-ethyl-5-formyl-1H-pyrrole-2,4-dicarboxylate; 2,4-ethyl-3-methyl-5-hydroxymethyl-1H-pyrrole-2,4-dicarboxylate; 2-tert-butyl-4-ethyl-3-ethyl-5-formyl-1H-pyrrole-2,4-dicarboxylate; ethyl 5-[(tert-butylamino)carbonyl]-4-ethyl-2-formyl-1H-pyrrole-3-carboxylate; 2-tert-butyl-4-ethyl-3-ethyl-5-formyl-1-methyl-1H-pyrrole-2,4-dicarboxylate; or salts thereof); a fungal alkaloid (e.g., K-252a ((9S-(9α, 10β, 12α))-2,3,9,10,11,12-hexahydro-10-hydroxy-10-(m ethoxy carbonyl)-9-methyl-9,12-epoxy-1H-diindolo[1,2,3-fg:3',2',1'-kl]pyrrolo[3,4-i][1,6]benzodiazocin-1-one)); an alkyl 6-(N-substituted sulfamoyl)cyclohex-1-ene-1-carboxylate compound (e.g., ethyl 6-[N-(2-chlorophenyl)sulfamoyl]yclohex-1-ene-1-carboxylate; ethyl 6-[N-(2,4-difluorophenyl) sulfamoyl]cyclohex-1-ene-1-carboxylate; ethyl 6-[N-(2,4,5-trifluorophenyl) sulfamoyl]cyclohex-1-ene-1-carboxylate; ethyl 6-[N-(2-chloro-4-fluorophenyl)sulfamoyl]cyclohex-1-ene-1-carboxylate; TAK-242 (ethyl (6R)-6-[N-(2-chloro-4-fluorophenyl)sulfamoyl]cyclohex-1-ene-1-carboxylate); and salts thereof); a fluorosulfonyl compound (e.g., such as fluorosulfonylbenzoate compounds, (2-aminoethyl)benzenesulfonyl fluoride (AEBSF), 5'-p-fluorosulfonylbenzoyl adenosine (FSBA), and compound 1 ([(2R,3R,4R,5R)-5-[4-amino-5-(4-methylphenyl) pyrrolo[2,3-d]pyrimidin-7-yl]-3-hydroxy-4-prop-2-ynoxyoxolan-2-yl]methyl 4-fluorosulfonylbenzoate) from Gushwa N N et al., "Selective targeting of distinct active site nucleophiles by irreversible Src-family kinase inhibitors," J. Am. Chem. Soc. 2012; 134:20214-20217; or salts thereof); a sulfonyl fluoride probe (e.g., compounds 1-4 from Zhao Q et al., "Broad-spectrum kinase profiling in live cells with lysine-targeted sulfonyl fluoride probes," J. Am. Chem. Soc. 2017; 139:680-685; or salts thereof); a purine-based cyclin-dependent kinase inhibitor (see, e.g., NU6102 (4-[[6-(cyclohexylmethoxy)-9H-purin-2-yl]amino]-benzene sulfonamide), NU2058 (6-(cyclohexyl-methoxy)-9H-purin-2-amine), NU6094 (6-(cyclohexyl methoxy)-N-[4-phenyl]-9H-purin-2-amine), NU6086 (4-[[6-(cyclohexylmethoxy)-7H-purin-2-yl]amino]phenol), NU6300 (6-(cyclohexylmethoxy)-N-[4-(vinylsulfonyl)phenyl]-9H-purin-2-amine), NU6310 (6-(cyclohexylmethoxy)-N-[4-(ethylsulfonyl)phenyl]-9H-purin-2-amine), NU6155 (6-(cyclohexylmethoxy)-N-[4-(methylsulfonyl)phenyl]-9H-purin-2-amine), NU6483 (6-(cyclohexylmethoxy)-N-[4-(2-hydroxyethylsulfonyl)phenyl]-9H-purin-2-amine), or salts thereof); a stilbene compound (see, e.g., compounds 1-4 (S-phenyl 3-[2-(3,5-dibromo-4-hydroxyphenyl)ethenyl]benzenecarbothioate; S-phenyl 3-[2-(3,5-dimethyl-4-hydroxyphenyl) ethenyl]benzenecarbothioate; (2-nitrophenyl) 3-[(E)-2-(4-hydroxy-3,5-dimethylphenyl)ethenyl]benzoate; and (4-fluorophenyl) 3-[(E)-2-(4-hydroxy-3,5-dimethylphenyl)ethenyl]benzoate from Choi S et al., "Chemoselective Small molecules that covalently modify one Lys in a non-enzyme protein in plasma," Nat. Chem. Biol. 2010; 6:133-139; and compounds 1a-1d (2-(3,5-dimethylphenyl)-2,3-dihydro-1,3-benzoxazole; 2-(3,5-dibromophenyl)-2,3-dihydro-1,3-benzoxazole; 2-(4-hydroxyl-3,5-dimethylphenyl)-2,3-dihydro-1,3-benzoxazole; and 2-(4- hydroxyl-3,5-dibromophenyl)-2,3-dihydro-1,3-benzoxazole), 3d (3,5-dibromobiphenyl-4-ol), 4d (2,6-dibromo-4-(2-phenylethyl)phenol), 5d (4-anilino-2,6-dibromophenol), 3c (3,5-dimethyl biphenyl-4-ol), 4c (2,6-dimethyl-4-(2-phenylethyl)phenol), 7d (1-(3,5-dibromo-4-methylphenyl)-3-phenyl-urea), and 9d (N-(3,5-dibromo-4-hydroxyl-phenyl) benzamide) from Johnson S M et al., "Toward optimization of the linker substructure common to transthyretin amyloidogenesis inhibitors using biochemical and structural studies," J. Med Chem. 2008; 51:6348-6358; and salts thereof); an 8-N-benzyl adenosine reversible inhibitor (e.g., ((2R,3R,4S,5R)-2-(6-amino-8-((4-chlorobenzyl)amino)-9H-purin-9-yl)-5-(hydroxymethyl)tetrahydrofuran-3,4-diol)); an 8-N-benzyl adenosine covalent inhibitor (e.g., 3-((2R,3S,4R,5R)-5-(6-amino-8-((4-chlorobenzyl) amino)-9H-purin-9-yl)-3,4-dihydroxytetrahydrofuran-2-yl)propyl acrylate); an adenosine-derived ATP-competitive inhibitor (e.g., tubercidin, sangivamycin, 8-aminosangivamycin, 8-aminotoyocamycin, benzyltoyocamycin, 8-N-benzyladenosine, compounds 3 (8-amino adenosine), 4 (2-[6-amino-8-(methylamino)purin-9-yl]-5-(hydroxymethyl)oxolane-3,4-diol), 7 (2-[6-amino-8-(methylamino)purin-9-yl]-5-(methyl)oxolane-3,4-diol), 10 (sangivamycin), 12-15 (4-amino-6-(methylamino)-7-[(2R,3R,4S,5R)-3,4-dihydroxy-5-(hydroxymethyl)oxolan-2-yl]pyrrolo[2,3-d]pyrimidine-5-carbonitrile; 4-amino-7-[(2R,3R,4S,5R)-3,4-dihydroxy-5-(hydroxymethyl)oxolan-2-yl]-6-(methylamino) pyrrolo[2,3-d]pyrimidine-5-carboxamide; 4-amino-6-(benzylamino)-7-[(2R,3R,4S,5R)-3,4-dihydroxy-5-(hydroxymethyl)oxolan-2-yl]pyrrolo[2,3-d]pyrimidine-5-carbonitrile; and 2-[6-amino-8-(benzylamino)purin-9-yl]-5-(hydroxymethyl)oxolane-3,4-diol), and 17-21 (2-[6-amino-8-(quinoline-4-ylamino)purin-9-yl]-5-(hydroxymethyl) oxolane-3,4-diol; 2-[6-amino-8-(4-chlorobenzylamino) purin-9-yl]-5-(hydroxymethyl)oxolane-3,4-diol; 2-[6-amino-8-(4-fluorobenzylamino)purin-9-yl]-5-(hydroxymethyl)oxolane-3,4-diol; 2-[6-amino-8-(4-methylbenzylamino)purin-9-yl]-5-(hydroxymethyl)oxolane-3,4-diol; and 2-[6-amino-8-(3,4-dichlorobenzylamino)purin-9-yl]-5-(hydroxymethyl)oxolane-3,4-diol) from Cheeseman M D et al., "Exploiting protein conformational change to optimize adenosine-derived inhibitors of HSP70," J. Med. Chem. 2016; 59:4625-4636; a peptide inhibitor including an unnatural amino acid with aryl sulfonyl fluoride (e.g, peptides 2-5 (Ac-QSQQTF*NLWRLL #QN-NH$_2$, Ac-QSQQTF*NX$^1$WRLL #QN-NH$_2$, AC-QSQQTF*NX$^2$ WRLL #QN-NH2, and Ac-QSQQTA*NX$^2$WRLL #QN-NH$_2$, where a bridge —(CH$_2$)$_6$(CH=CH)(CH$_2$)$_3$— extends from * to #, X$^1$ is an unnatural amino acid of 2-amino-3-[(4-fluorosulfonylbenzoyl)amino]propanoic acid, and X$^2$ is an unnatural amino acid of 2-amino-3-[(3-fluorosulfonylbenzoyl)amino]propanoic acid) from Hoppmann C et al., "Proximity-enabled bioreactivity to generate covalent peptide inhibitors of p53-Mdm4," Chem. Commun. 2016; 52:5140-5143; or salts thereof); an indole-based inhibitor (e.g., 3-(3-(naphthalen-1-yloxy)propyl)-1H-indole-2-carboxylic acid; 7-(3-((4-borono-3-formylphenoxy)methyl)-1,5-dimethyl-1H-pyrazol-4-yl)-3-(3-(naphthalen-1-yloxy) propyl)-1H-indole-2-carboxylic acid; 7-(3-((4-borono-3-formylphenoxy)methyl)-1,5-dimethyl-1H-pyrazol-4-yl)-1-methyl-3-(3-(naphthalen-1-yloxy)propyl)-1H-indole-2-carboxylic acid; 7-(3-((3-acetyl-4-boronophenoxy) methyl)-1,5-dimethyl-1H-pyrazol-4-yl)-3-(3-(naphthalen-1-yloxy) propyl)-1H-indole-2-carboxylic acid; 7-(3-((3-acetylphenoxy)methyl)-1,5-dimethyl-1H-pyrazol-4-yl)-3-(3-(naphthalen-1-yloxy)propyl)-1H-indole-2-carboxylic acid; or salts thereof); or an iminoboronate compound (e.g., 1-butylamine and 2-formylbenzeneboronic acid; compounds 4-9 from Cal PMSD et al., "Iminoboronates: a new strategy for reversible protein modification," J. Am. Chem. Soc. 2012; 134:10299-10305; or salts thereof).

Further exemplary inhibitors (e.g., lysine inhibitors) include an organic moiety including one or more aryl sulfonyl fluoride groups (e.g., —Ar—SO$_2$F, where Ar is an optionally substituted aryl group, as defined herein, in which the —SO$_2$F group is in the para, meta, or ortho position); an organic moiety including one or more aryl boronic acid groups (e.g., —Ar—B(OH)$_2$, where Ar is an optionally substituted aryl group, as defined herein, in which the —B(OH)$_2$ group is in the para, meta, or ortho position) or aryl boronic acid carbonyl groups (e.g., —Ar*—B(OH)$_2$, where Ar* is an optionally substituted aryl group, as defined herein, having a carbonyl substitution, in which the —B(OH)$_2$ group is in the para, meta, or ortho position); an organic moiety include one or more ester groups (e.g., —C(O)—OAr, where Ar is an optionally substituted aryl group, as defined herein, such as, e.g., an Ar including one or more halo, carbonyl, carboxyaldehyde, carboxyl, and alkoxy (e.g., as defined herein); an organic moiety including one or more aldehyde groups (e.g., one or more carboxyaldehyde groups, such as an optionally substituted alkyl, heteroalkyl, aryl, alkaryl, or heterocyclyl group having one or more carboxyaldehyde groups (—C(O)H); or R'-Lk-R', where Lk is a linker, such as an optionally substituted alkylene, alkyleneoxy, heteroalkylene, heteroalkyleneoxy, arylene, or aryleneoxy having one or more carboxyaldehyde groups, and where each of R' is an optionally substituted alkyl, heteroalkyl, aryl, alkaryl, or heterocyclyl); or an organic moiety include one or more optionally substituted triazine groups (e.g., -Het, where Het is an optionally substituted 1,3,5-triazine, 1,2,3-triazine, or 1,2,4-triazine group having one or more optional substitutions described herein for aryl, such as, e.g., halo, alkyl, alkoxy, etc.), as well as salts thereof.

Exemplary, non-limiting inhibitors (e.g., arginine inhibitors) include phenylglyoxal, p-azidophenylglyoxal, 2,3-butanedione, 1,2-cyclohexanedione, 5,6,9,10-tetrahydro[1,10] phenanthrolino[2,3-b][1,10]phenanthroline-2,13-dicarboxylic acid (e.g., including salts thereof, such as a potassium salt), 5,6,9,10-tetrahydrodinaphtho[1,2-b:2',1'-g] [1,8]naphthyridine-2,13-dicarboxylic acid (e.g., including salts thereof, such as a potassium salt), 5,6,9,10-tetrahydro benzo[7,8]quino[2,3-b][1,10]phenanthroline-2,13-dicarboxylic acid (e.g., including salts thereof, such as a potassium salt), as well as salts thereof.

Further exemplary inhibitors (e.g., arginine inhibitors) include an organic moiety including two or more carbonyl groups (e.g., two or more —C(O)— groups, such as a dione group (or —C(O)—C(O)—), including a cyclodione group in which a cycloalkyl group includes two or more carbon atoms within the ring substituted with an oxo group to form two or more —C(O)— groups, such as 1,2-cyclopentanedione, 1,2-cyclohexanedione, 1,2-cycloheptanedione, or 1,2-cyclooctanedione; or an alkanedione group in which an alkyl group includes two or more carbon atoms within the group substituted with an oxo group to form two or more —C(O)— groups, such as 2,3-butanedione, 2,3-pentanedione, or 2,3-hexanedione); an organic moiety including two or more phosphonate groups (e.g., such as X$^1$-Lk-X$^2$, wherein each of X$^1$ and X$^2$ is a phosphonate group (e.g., as defined herein) and Lk is a linker, such as an optionally substituted alkylene, alkyleneoxy, heteroalkylene, heteroalkyleneoxy, arylene, or aryleneoxy); an organic moiety including two or more carboxyl or carboxylate groups (e.g., such as $X^1$-Lk-$X^2$, wherein each of $X^1$ and $X^2$ is a carboxyl or carboxylate group (e.g., as defined herein) and Lk is a linker, such as an optionally substituted alkylene, alkyleneoxy, heteroalkylene, heteroalkyleneoxy, arylene, or aryleneoxy), as well as salts thereof.

Other exemplary inhibitors include, e.g., Ar—C(O)—C(O)H; Ak-C(O)—C(O)H; Ak-C(O)—C(O)-Ak; and $A^1$-C(O)—C(O)-$A^2$, and salts thereof, where Ar is an optionally substituted aryl (e.g., as defined herein), where Ak is an optionally substituted alkyl (e.g., as defined herein), and where $A^1$ and $A^2$, taken together, is an optionally substituted alkylene, alkyleneoxy, heteroalkylene, or heteroalkyeneoxy group (e.g., as defined herein) and $A^1$ and $A^2$, taken together, form an optionally substituted cycloalkyl or heterocyclyl group (e.g., as defined herein); $HO_2C$-Lk-$CO_2H$ or $^-O_2C$-Lk-$CO_2^-$, where Lk is a linker, such as an optionally substituted alkylene, alkyleneoxy, heteroalkylene, heteroalkyleneoxy, arylene, or aryleneoxy), and salts thereof; (R'O)(HO)P(O)-Lk-P(O)(OH)(OR') or (R'O)(O)P(O)-Lk-P(O)($O^-$)(OR'), where Lk is a linker, such as an optionally substituted alkylene, alkyleneoxy, heteroalkylene, heteroalkyleneoxy, arylene, or aryleneoxy, as well as salts thereof, and where R' is optionally substituted alkyl, aryl, alkaryl, or heterocyclyl; or salts of any of these.

Figure 11B:
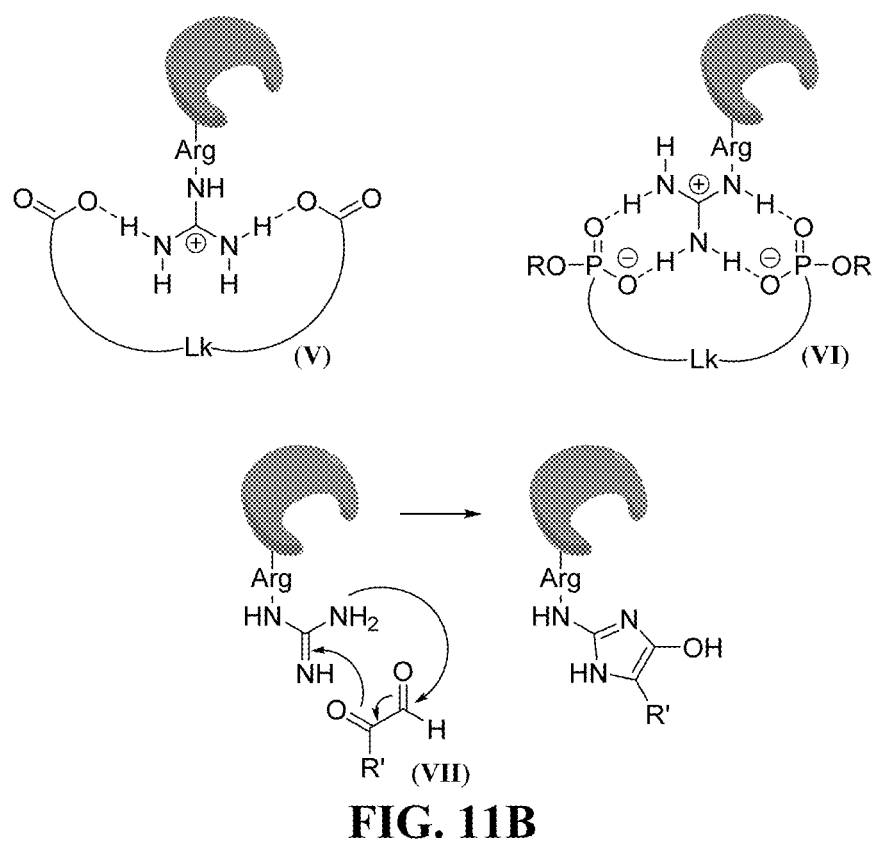

FIG. 11A-11B provides schematics of exemplary inhibitors (e.g., lysine inhibitors and/or arginine inhibitors), including compounds having structures (I), (II), (III), (IV), (V), (VI), or (VII) or a salt thereof. Also provided in FIG. 11A-11B are exemplary schematics of a reaction between an amino acid residue (e.g., lysine or arginine) with a compound.

In the compound of structure (I), R' can be any useful moiety (e.g., an organic moiety), including but not limited to an optionally substituted alkyl, heteroalkyl, aryl, alkaryl, heterocyclyl, alkheterocyclyl, cycloalkyl, and alkcycloalkyl (e.g., as defined herein); as well as -Lk-R, in which Lk is a linker (e.g., such as an optionally substituted alkylene, alkyleneoxy, heteroalkylene, heteroalkyleneoxy, arylene, or aryleneoxy) and R is any useful moiety (e.g., an organic moiety), including but not limited to an optionally substituted alkyl, heteroalkyl, aryl, alkaryl, heterocyclyl, alkheterocyclyl, cycloalkyl, and alkcycloalkyl (e.g., as defined herein).

In the compound of structure (II), Ar can be any useful moiety (e.g., an organic moiety), including but not limited to an optionally substituted aryl, alkaryl, heterocyclyl, alkheterocyclyl, heteroaryl, or alkheteroaryl (e.g., as defined herein); as well as -Lk-R, in which Lk is a bond or linker (e.g., such as a covalent bond or an optionally substituted alkylene, alkyleneoxy, heteroalkylene, heteroalkyleneoxy, arylene, or aryleneoxy) and R is any useful moiety (e.g., an organic moiety), including but not limited to an optionally substituted aryl, alkaryl, heterocyclyl, alkheterocyclyl, heteroaryl, or alkheteroaryl (e.g., as defined herein).

In the compound of structure (III), R' can be any useful moiety (e.g., an organic moiety), including but not limited to an optionally substituted alkyl, heteroalkyl, aryl, alkaryl, heterocyclyl, alkheterocyclyl, cycloalkyl, and alkcycloalkyl (e.g., as defined herein); as well as -Lk-R, in which Lk is a linker (e.g., such as an optionally substituted alkylene, alkyleneoxy, heteroalkylene, heteroalkyleneoxy, arylene, or aryleneoxy) and R is any useful moiety (e.g., an organic moiety), including but not limited to an optionally substituted alkyl, heteroalkyl, aryl, alkaryl, heterocyclyl, alkheterocyclyl, cycloalkyl, and alkcycloalkyl (e.g., as defined herein).

In the compound of structure (IV), R' can be any useful moiety (e.g., an organic moiety), including but not limited to an optionally substituted alkyl, heteroalkyl, aryl, alkaryl, heterocyclyl, alkheterocyclyl, cycloalkyl, and alkcycloalkyl (e.g., as defined herein); as well as -Lk-R, in which Lk is a linker (e.g., such as an optionally substituted alkylene, alkyleneoxy, heteroalkylene, heteroalkyleneoxy, arylene, or aryleneoxy) and R is any useful moiety (e.g., an organic moiety), including but not limited to an optionally substituted alkyl, heteroalkyl, aryl, alkaryl, heterocyclyl, alkheterocyclyl, cycloalkyl, and alkcycloalkyl (e.g., as defined herein); and X can be any useful moiety (e.g., a substitution provided for optionally substituted alkyl or aryl, as defined herein), including a leaving group (e.g., halo, alkoxy, haloalkyl, etc.)

In the compound of structure (V) or (VI), Lk can be any useful moiety (e.g., a linker), such as an optionally substituted alkylene, alkyleneoxy, heteroalkylene, heteroalkyleneoxy, arylene, or aryleneoxy. In the compound of structure (VI), R is any useful moiety (e.g., an organic moiety), including but not limited to an optionally substituted alkyl, heteroalkyl, aryl, alkaryl, heterocyclyl, alkheterocyclyl, cycloalkyl, alkcycloalkyl, or a leaving group (e.g., halo, alkoxy, haloalkyl, etc.). In other embodiments, R can be -Lk-R', in which Lk is a linker (e.g., such as an optionally substituted alkylene, alkyleneoxy, heteroalkylene, heteroalkyleneoxy, arylene, or aryleneoxy) and R' is any useful moiety (e.g., an organic moiety), including but not limited to an optionally substituted alkyl, heteroalkyl, aryl, alkaryl, heterocyclyl, alkheterocyclyl, cycloalkyl, and alkcycloalkyl (e.g., as defined herein).

In the compound of structure (VII), R' can be any useful moiety (e.g., an organic moiety), including but not limited to an optionally substituted alkyl, heteroalkyl, aryl, alkaryl, heterocyclyl, alkheterocyclyl, cycloalkyl, and alkcycloalkyl (e.g., as defined herein); as well as -Lk-R, in which Lk is a linker (e.g., such as an optionally substituted alkylene, alkyleneoxy, heteroalkylene, heteroalkyleneoxy, arylene, or aryleneoxy) and R is any useful moiety (e.g., an organic moiety), including but not limited to an optionally substituted alkyl, heteroalkyl, aryl, alkaryl, heterocyclyl, alkheterocyclyl, cycloalkyl, and alkcycloalkyl (e.g., as defined herein).

Further compounds (e.g., arginine and/or lysine inhibitors) include those disclosed in in Akçay G et al., "Inhibition of Mcl-1 through covalent modification of a noncatalytic lysine side chain," *Nat. Chem. Biol.* 2016; 12:931-936; Anderson K E et al., "Chemoproteomics-enabled covalent ligand screening reveals a thioredoxin-caspase 3 interaction disruptor that impairs breast cancer pathogenicity," *ACS Chem. Biol.* 2017; 12:2522-2528; Bell I M et al., "Biochemical and structural characterization of a novel class of inhibitors of the type 1 insulin-like growth factor and insulin receptor kinases," *Biochemistry* 2005; 44:9430-9440; Bell T W et al., "Role of pyridine hydrogen-bonding sites in recognition of basic amino acid side chains," *J. Am. Chem. Soc.* 2002; 124:14092-14103; Bell T W et al., "A small-molecule guanidinium receptor: the arginine cork," *Angew. Chem. Int. Ed.* 1999; 38:2543-2547; Cal PMSD et al., "Iminoboronates: a new strategy for reversible protein modification," *J. Am. Chem. Soc.* 2012; 134:10299-10305; Cheeseman M D et al., "Exploiting protein conformational change to optimize adenosine-derived inhibitors of HSP70," *J. Med. Chem.* 2016; 59:4625-4636; Choi S et al., "Chemoselective small molecules that covalently modify one Lys in a non-enzyme protein in plasma," *Nat. Chem. Biol.* 2010; 6:133-139; Davies T G et al., "Structure-based design of a potent purine-based cyclin-dependent kinase inhibitor," *Nature Struct. Biol.* 2002; 9:745-749; Gushwa N N et al., "Selective targeting of distinct active site nucleophiles by irreversible Src-family kinase inhibitors," *J. Am. Chem. Soc.* 2012; 134:20214-20217; Hacker S M et al., "Global profiling of lysine reactivity and ligandability in the human proteome," *Nat. Chem.* 2017; 9:1181-1190; Hoppmann C et al., "Proximity-enabled bioreactivity to generate covalent peptide inhibitors of p53-Mdm4," *Chem. Commun.* 2016; 52:5140-5143; Johnson S M et al., "Toward optimization of the linker substructure common to transthyretin amyloidogenesis inhibitors using biochemical and structural studies," *J. Med. Chem.* 2008; 51:6348-6358; Lonsdale R et al., "Structure-based design of targeted covalent inhibitors," *Chem. Soc. Rev.* 2018; 47:3816-3830; Morgan H P et al., "A new family of covalent inhibitors block nucleotide binding to the active site of pyruvate kinase," *Biochem. J.* 2012; 448:67-72; Narayanan A et al., "Sulfonyl fluorides as privileged warheads in chemical biology," *Chem. Sci.* 2015; 6:2650-2659; Pal P K et al., "Affinity labeling of the inhibitory DPNH site of bovine liver glutamate dehydrogenase by 5'-fluorosulfonyl benzoyl adenosine," *J. Biol. Chem.* 1975; 250:8140-8147; Pettinger J et al., "Lysine-targeting covalent inhibitors," *Angew. Chem. Int. Ed.* 2017; 26:15200-15209; Pettinger J et al., "An irreversible inhibitor of HSP72 that unexpectedly targets lysine-56," *Angew. Chem. Int. Ed.* 2017; 56(13):3536-3540; Shannon D A et al., "Investigating the proteome reactivity and selectivity of aryl halides," *J. Am. Chem. Soc.* 2014; 136:3330-3333; Takahashi K, "The reaction of phenylglyoxal with arginine residues in proteins," *J. Biol. Chem.* 1968; 243:6171-6179; Tanaka K et al., "The inhibitory mechanism of bovine pancreatic phospholipase $A_2$ by aldehyde terpenoids," *Tetrahedron* 1999; 55:1657-1686; Tanaka K et al., "Synthesis of anew phospholipase $A_2$ inhibitor of an aldehyde terpenoid and its possible inhibitory mechanism," *Tetrahedron Lett.* 1998; 39:1185-1188; Toi K et al., "Studies on the chemical modification of arginine: 1. The reaction of 1,2-cyclohexanedione with arginine and arginyl residues of proteins," *J. Biol. Chem.* 1967; 242:1036-1043; Volz T J et al., "Covalent and noncovalent chemical modifications of arginine residues decrease dopamine transporter activity," Synapse 2004; 52:272-282; Yamada M et al., "Discovery of novel and potent small-molecule inhibitors of NO and cytokine production as antisepsis agents: synthesis and biological activity of alkyl 6-(N-substituted sulfamoyl)cyclohex-1-ene-1-carboxylate," *J. Med. Chem.* 2005; 48:7457-7467; Zhao Q et al., "Broad-spectrum kinase profiling in live cells with lysine-targeted sulfonyl fluoride probes," *J. Am. Chem. Soc.* 2017; 139:680-685; Int. Pub. No. WO 2003/024183; U.S. Pat. Pub. No. US 2014/275234; U.S. Pat. No. 8,586,626, each of which is incorporated herein by reference in its entirety.

Activity of Inhibitors

The present invention relates, in part, to determining an activity of a candidate compound with a protein (e.g., a viral envelope E protein, such as any described herein; a protein including a sequence having at least 80% sequence identity to any one of SEQ ID NOs:35-104 or 192; a protein including a sequence having at least 80% sequence identity to any one of SEQ ID NOs: 107-176; a protein having any one of SEQ ID NOs: 105, 106, 179, 181, 182, 185, 187, and 188; and/or a protein having any one of SEQ ID NOs: 177, 178, 180, 183, 184, 186, and 189-191, including any polypeptide sequence described herein). Activity of the candidate compound can be determined by measuring whether or not the compound binds (e.g., reversibly binds or irreversibly binds) to the protein or polypeptide, such as by way of mass spectrometry, electrospray ionization mass spectrometry, radioligand binding assay, fluorescence polarization, fluorescence binding assay (e.g., by use of fluorescence resonance energy transfer), and/or surface plasmon spectroscopy or by determining the binding association constant $K_a$, a binding dissociation constant $K_d$, or the inhibitor constant $K_i$; by determining the structure of a complex including the compound bound to the protein or polypeptide, such as by way of x-ray crystallography, electron spectroscopy, and/or nuclear magnetic resonance (NMR) spectroscopy; by determining the pharmacodynamic or pharmacokinetic effects of the compound with the protein or polypeptide, such as by determining the half maximal inhibitory concentration ($IC_{50}$) and/or half maximal effective concentration ($EC_{50}$).

The activity of the test protein can be compared to activity of a mutant protein having one or more mutations identified in the present application to be relevant to lipid binding (e.g., R73, R99, K246, and/or K247 of SEQ ID NO: 192). If these relevant sites are important to viral fusion, then mutation at one or more of those sites should provide a mutant with reduced viral fusion and, ultimately, reduced viral infection. Thus, efficacy of a candidate therapeutic compound can be determined by comparing the activity of the compound with the test protein and the mutant protein, in which an efficacious candidate compound will provide indicate greater inhibition with the test protein, as compared to the mutant protein. Greater inhibition can be characterized by, e.g., an $IC_{50}$ value with the test protein that is lower than an $IC_{50}$ value for the mutant protein; an inhibitor constant $K_i$ value with the test protein that is lower than a $K_i$ value for the mutant protein; and/or an equilibrium dissociation constant $K_d$ value with the test protein that is lower than a $K_d$ value with the mutant protein.

Combination Therapy

The inhibitors herein (e.g., lysine and/or arginine inhibitors) can be combined with one or more other agents for combination therapy. Exemplary other agents include, e.g., chloroquine; geneticin; amodiaquine; hydroxychloroquine; celgosivir; castanospermine; N-nonyl-deoxynojirimycin; sodium oxamate; 2-deoxy-D-glucose; D-like isoneplanocin; balapiravir; sofosbuvir; UV-4B (2-(hydroxymethyl)-1-(9-methoxynonyl)piperidine-3,4,5-triol, HCl salt); anthraquinone; BP13944 (N-ethyl-N,N-bis(hydroxymethyl)hexadecan-1-aminium bromide); ZINC04321905 (2-[3-(7-fluoro-1,2-dihydronaphthalene)]-6-fluoro-3,4-dihydro-1H-naphthalen-2-one); biliverdin; ARDP0006 (1,8-dihydroxy-4,5-dinitroanthracene-9,10-dione); policresulen; SK-12 (2-{[1-hydroxy-4-(4-methyl-3-nitro-benzenesulfonamido) naphthalen-2-yl]sulfanyl}acetic acid); NSC135618 ((3E)-3-[(2-chloro-4-nitrophenyl)hydrazinylidene]-N-(3-chlorophenyl)-6-oxocyclohexa-1,4-diene-1-carboxamide); 4-(1,3-dioxoisoindolin-2-yl)-N-(4-ethylphenyl) benzenesulphonamide; 4-(1,3-dioxoisoindolin-2-yl)-N-(naphthalen-1-yl) benzenesulphonamide; 1-(2-(4-fluorophenyl)-2-oxoethyl)-3,5-bis(4-nitrobenzylidene)piperidin-4-one; 1-(2-(4-methoxyphenyl)-2-oxoethyl)-3,5-bis(4-nitrobenzylidene) piperidin-4-one; ST-610 (1-[2-(1,3-benzoxazol-2-ylsulfanyl)acetyl]-4-piperidin-1-ylpiperidine-4-carboxamide); suramin; ivermectin; 4-[5-(4-chlorophenyl)thiophen-2-yl]-N-(pyridin-3-ylmethyl)quinazolin-2-amine; 1662G07 (N-(3-chloroanilino)-2-(furan-2-yl)-2-oxoethanimidoyl cyanide); 3-110-22 (N-(3-trifluoromethylanilino)-2-(2,3-dihydrobenzofuran-2-yl)-2-oxoethanimidoyl cyanide); ST-148 (3-amino-N-(5-phenyl-1,3,4-thiadiazol-2-yl)-6,7,8,9-tetrahydro-5H-cyclohepta[b]thieno[3,2-e]pyridine-2-carboxamide); NITD-1 (N-(2-carboxyphenyl)-4-(3-methyl-5-oxo-4H-pyrazol-1-yl)benzenesulfonamide); NITD-2 (N-(2-carboxyphenyl)-4-(1-[(2-methylphenyl)methyl]pyrazol-4-yl)benzenesulfonamide); HeE1-2Tyr (-{[8-(cyclohexyloxy)-1-oxo-2-phenyl-1H-pyrido[2,1-b][1,3]benzothiazol-4-yl]carbonyl}-L-tyrosinate); DMB220 (5-(benzenesulfonylmethyl)-N,3-dihydroxy-4-(hydroxymethyl)pyridine-2-carboxamide); 66E2 (1-(5-ethyl-1H-pyrido[4,3-b]indol-8-yl)-3-(2-methyl-4-nitro-phenyl)urea); (3R)-5-chloro-1'-[(4-chlorophenyl)methyl]spiro[1H-indole-3,4'-5H-pyrazolo[3,4-b]pyridine]-2,6'-dione; (3R)-5-chloro-1'-[(4-chloropyridinyl)methyl]spiro[1H-indole-3,4'-5H-pyrazolo[3,4-b]pyridine]-2,6'-dione; 10-allyl-7-chloro-9(10H)-acridone; celastrol; 4-HPR (N-(4-hydroxyphenyl) retinamide); lactimidomycin (LTM); PF-429242 (4-[(diethylamino)methyl]-N-[2-(2-methoxyphenyl)ethyl]-N-(3R)-3-pyrrolidinylbenzamide); QL47 (1-(1-acryloylin-6-yl)-9-(1-methyl-1H-pyrazol-4-yl)benzo[h][1,6]) naphthyridin-2(1H)-one); YKL-04-085 ((E)-4-(dimethylamino)-N-(2-methyl-5-(9-(1-methyl-1H-pyrazol-4-yl)-2-oxobenzo[h] quinolin1(2H)-yl)phenyl)but-2-enamide); 5-(3,4-dichlorophenyl)-N-[2-(p-tolyl)benzotriazol-5-yl]furan-2-carboxamide (26124033); saracatinib (AZD0530); dasatanib; sinefungin; S-adenosyl-L-homocysteine; ribavirin; brequinar; mycophenolic acid; EICAR (5-ethynyl-1-ribofuranosylimidazole-4-carboxamide or 1-[(2R,3R,4S,5R)-3,4-dihydroxy-5-(hydroxymethyl)oxolan-2-yl]-5-ethynylimidazole-4-carboxamide); hymeglusin; lovastatin; zaragozic acid; cerulenin; lanatoside C; andrographolide; cobalt protoporphyrin (CoPP); bromocriptine (BRC); eriodictyol 7-O-glucuronide; luteolin 8-C-beta-glucopyranoside; [−]-epicatechin-3-O-gallate; 6-O-trans-p-coumaroylgeniposide; luteolin-7-O-glucoside; octyl-2-O-sulfo-β-D-glucose; 1-acetyllycorine; lycorine; N-desmethylclozanine; fluoxetine; salmeterol; 2-N-methyl-6-N-(3-hydroxylphenyl)-7H-purine-2,6-diamine; 4-guanidinomethylphenylacteyl-Arg-Ala-Arg-4-amidinobenzylamide; 4-guanidinomethyl-phenylacteyl-Arg-Tle-Arg-4-amidinobenzyl amide, where Tle is t-butylglycine; 4-guanidinomethyl-phenylacteyl-Arg-Tle-Arg-4-amidino benzyl amide (MI-1148); FWFT-LIKTQAKQPARYRRFC (SEQ ID NO: 193); MAILGD-TAWDFGSLGGVFTSIGKALHQVFGAIY (DN59, SEQ ID NO: 194); Ac-FAAGRR-αketo-SL-CONH$_2$ (SEQ ID NO: 195); Ac-FAAGRR-CHO (SEQ ID NO: 196); cyclic peptide GKRKSGCA (SEQ ID NO: 197); cyclic peptide CGKRKSC (SEQ ID NO: 198); cyclic peptide $^D$RRRKA-homoF-1Nal-$^D$F (SEQ ID NO: 199); Bz-Nle-Lys-Arg-B(OH)$_2$ (SEQ ID NO:200); AWDFGSLGGVFTSIGKA-LHQVFGAIYGAA (DV2$^{419\text{-}447}$, SEQ ID NO: 201); AWDFGSLGGVFTSIGKALHQVFGWWWGAA (DV2$^{419\text{-}447(www\ 442\text{-}444)}$, SEQ ID NO:202); Glu-Phe (EF); SVALVPHVGMGLETRTETWMSSEGAWKHVQRI-ETWILRHPG (MLH40, SEQ ID NO:203); Ac-RTSKKR-NH2 (SEQ ID NO:204); WYCW-NH$_2$ (SEQ ID NO:205); Bz-AKRR-H (SEQ ID NO:206); Bz-nKRR-B(OH)$_2$ (SEQ ID NO:207); 7-deaza-2'-C-methyl-adenosine; 2D22 antibody (DENV-2 specific human monoclonal antibody); Ab513 antibody (an-serotype MAb that neutralizes all four serotypes of DENV); compound 35 from Behnam MAM et al., "C-terminal residue optimization and fragment merging: discovery of a potent peptide-hybrid inhibitor of Dengue protease," ACS Med Chem. Lett. 2014; 5:1037-1042; compounds 42a and 45a from Weigel L F et al., "Phenylalanine and phenylglycine analogues as arginine mimetics in Dengue protease inhibitors," J. Med Chem. 2015; 58:7719-7733; compound 104 from Behnam M A M et al., "Discovery of nanomolar Dengue and West Nile virus protease inhibitors containing a 4-benzyloxyphenylglycine residue," J. Med. Chem. 2015; 58:9354-9370; compound 23i (2-((2-(3-bromophenyl)hydrazinylidene)methyl)-N'-(2-phenylethylidene) quinoline-4-carbohydrazide) from Deng J et al., "Discovery of novel small molecule inhibitors of Dengue viral NS2B-NS3 protease using virtual screening and scaffold hopping," J. Med. Chem. 2012; 55:6278-6293; compound MB21 ((E)-4-(5-(2-(5-chloro-1H-benzo[d]imidazol-2-yl)-2-cyanovinyl) thiophen-2-yl) benzoic acid) from Raut R et al., "A small molecule inhibitor of dengue virus type 2 protease inhibits the replication of all four dengue virus serotypes in cell culture," Virol. J. 2015; 12:16 (7 pp.); compound 14 from Li L et al., "Structure-guided discovery of a novel non-peptide inhibitor of Dengue virus NS2B-NS3 protease," Chem. Biol. Drug Des. 2015; 86:255-264; compounds 7 and 8 from Wu H et al, "Novel Dengue virus NS2B/NS3 protease inhibitors," Antimicrob. Agents Chemother. 2015; 59:1100-1109; as well as salts thereof.

Further exemplary other agents include a non-structural (NS) protein inhibitor, such as a NS3/NS2B protease inhibitor, a NS3 helicase inhibitor, a methyltransferase (MTase) inhibitor, a RNA-dependent RNA polymerase (RdRp) inhibitor, an NS1 inhibitor, an NS2B inhibitor, or an NS4B inhibitor; an NS5 polymerase inhibitor; as well as a structural protein inhibitor, such as a capsid protein inhibitor, a membrane precursor protein inhibitor, or an envelope protein inhibitor.

Other non-limiting agents include any described in Behnam M A M et al., "The medicinal chemistry of Dengue virus," J. Med. Chem. 2016; 59:5622-5649; Behnam M A M et al., "Discovery of nanomolar Dengue and West Nile virus protease inhibitors containing a 4-benzyloxyphenylglycine residue," J. Med Chem. 2015; 58:9354-9370; Behnam M A M et al., "C-terminal residue optimization and fragment merging: discovery of a potent peptide-hybrid inhibitor of Dengue protease," ACS Med Chem. Lett. 2014; 5:1037-1042; Deng J et al., "Discovery of novel small molecule inhibitors of Dengue viral NS2B-NS3 protease using virtual screening and scaffold hopping," J. Med. Chem. 2012; 55:6278-6293; Li L et al., "Structure-guided discovery of a novel non-peptide inhibitor of Dengue virus NS2B-NS3 protease," Chem. Biol. Drug Des. 2015; 86:255-264; Raut R et al., "A small molecule inhibitor of dengue virus type 2 protease inhibits the replication of all four dengue virus serotypes in cell culture," Virol. J. 2015; 12:16 (7 pp.); Weigel L F et al., "Phenylalanine and phenylglycine analogues as arginine mimetics in Dengue protease inhibitors," J. Med. Chem. 2015; 58:7719-7733; Tian Y S et al., "Dengue virus and its inhibitors: a brief review," Chem. Pharm. Bull. 2018; 66:191-206; and Wu H et al, "Novel Dengue virus NS2B/NS3 protease inhibitors," Antimicrob. Agents Chemother. 2015; 59:1100-1109, each of which is incorporated herein by reference in its entirety.

Flaviviruses

Exemplary flaviviruses include tick-borne viruses, mosquito-borne viruses, non-vertebrate viruses, and other flaviviruses. Further examples of flaviviruses include any in the genus Flavivirus, including, e.g., Alfuy virus, Alkhumra hemorrhagic fever virus (ALKV), Bagaza virus (BAGV), Baiyangdian virus (BYDV), Bamaga virus (BGV), Banzi virus (BANV), Bouboui virus (BOUV), Bussuquara virus (BUSV), Cacipacore virus (CPCV), Chaoyang virus, Culex flavivirus, Culex theileri flavivirus, Dengue virus (DENV), Donggang virus, Duck egg drop syndrome virus (DEDSV), Edge Hill virus (EHV), Fitzroy river virus, Hanko virus, Ilheus virus (ILHV), Israel turkey meningoencephalomyelitis virus (ITV), Japanese encephalitis virus (JEV), Jiangsu virus (JSV), Jugra virus (JUGV), Kedougou virus (KEDV), Kokobera virus (KOKV), Koutango virus (KOUV), Kunjin virus (KUNJ), Kyasanur Forest disease virus (KFDV), Langat virus (LANV), Layer flavivirus, Louping ill virus (LIV), New Mapoon virus (NMV), Murray Valley encephalitis virus (MVEV), Ntaya virus (NTAV), Omsk hemorrhagic fever virus (OHFV), Powassan virus (POWV), Rocio virus (ROCV), Saboya virus (SABV), St. Louis encephalitis virus (SLEV), Sepik virus (SEPV), Sitiawan virus (STWV), Spondweni virus (SPOV), Stratford virus (STRV), Tembusu virus (TMUV), T'Ho virus, tick-borne encephalitis virus (TBEV), Uganda S virus (UGSV), Usutu virus (USUV), Wesselsbron virus (WSLV), West Nile virus (WNV), Yaounde virus (YAOV), Yellow fever virus (YFV), and Zika virus (ZIKV), as well as strains or isolates of any of these.

EXAMPLES

Example 1; New Target for Inhibitors of Dengue Virus and Other Flaviviruses

We have discovered that lysine 246 and lysine 247 of the envelope protein of Dengue virus are critical for binding and anchoring of the virus to host cell endosomal membranes. This is an essential step in the membrane fusion process. Fusion of viral and host endosomal membranes is required for infectivity as it enables the nucleic acid of the virus to enter the cytosol of host cells. The two amino acids listed above are exposed on the surface of the mature virus and therefore are targets for inhibitors of Dengue virus infection.

Figure 2:
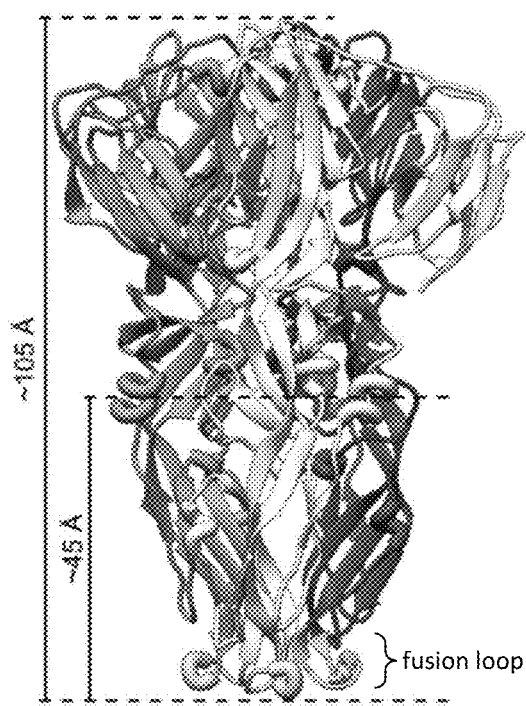
FIG. 2 shows schematics of an exemplary envelope (E) protein for a Dengue virus. Provided is the crystal structure of an E trimer showing the truncated trimer (TT, bottom, ~45 Å), including the fusion loop (FL).
Figure 3A:
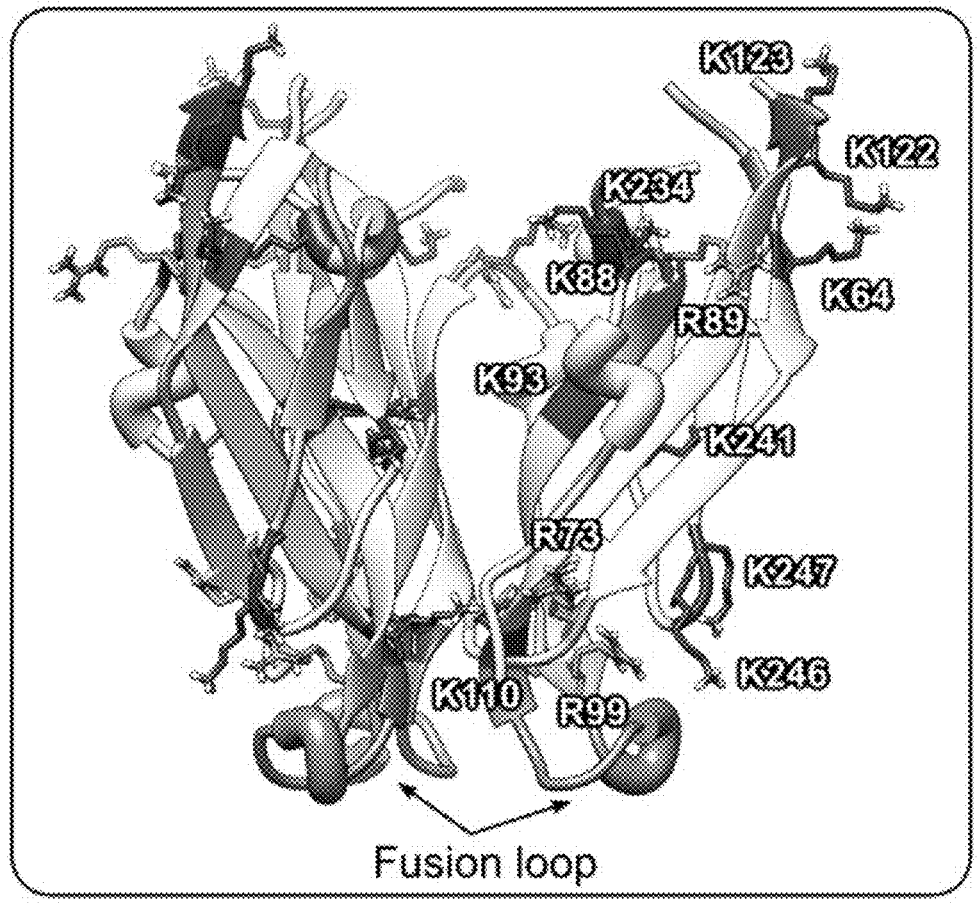
Figure 3B:
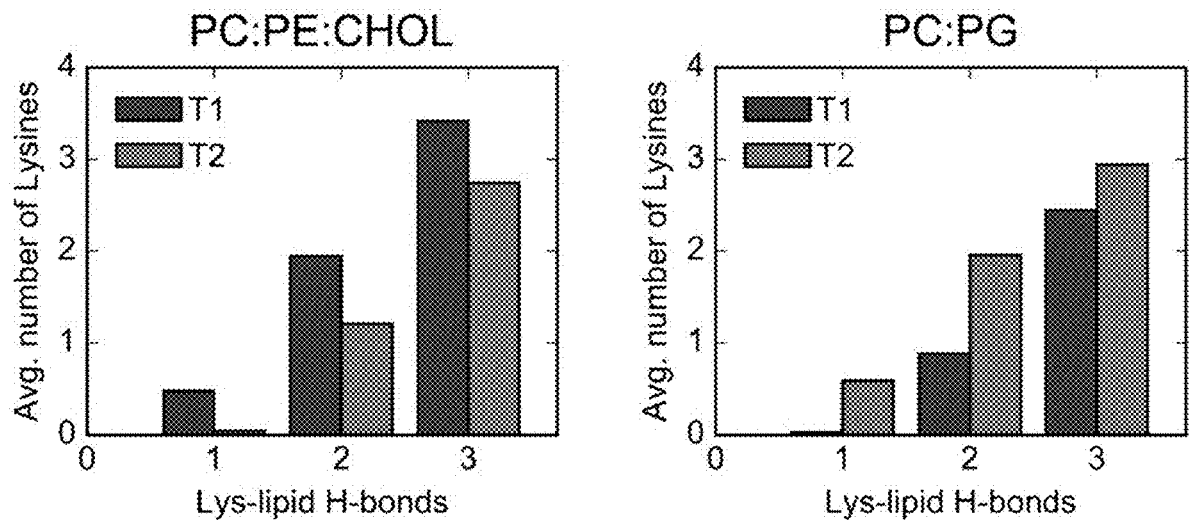
Figure 3F:
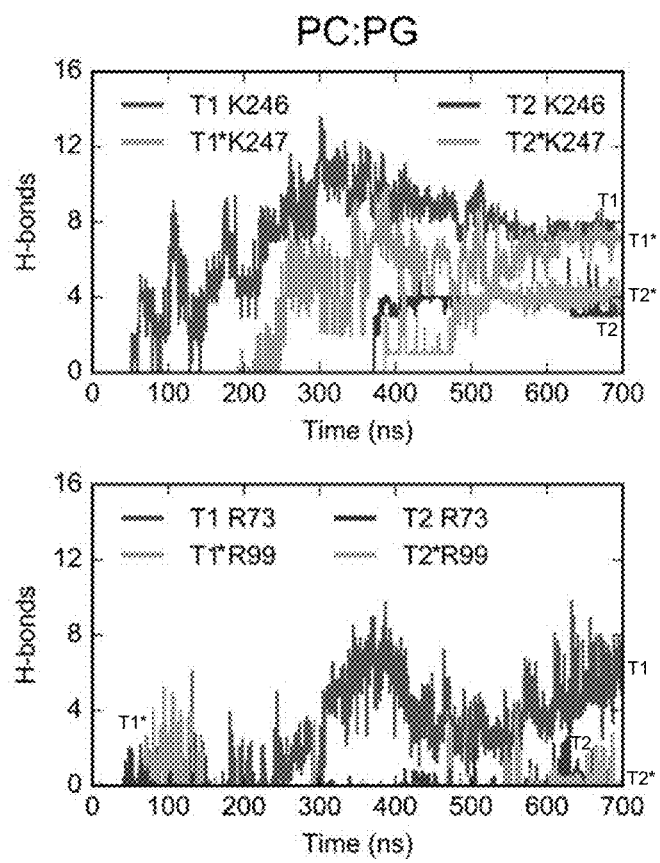

The envelope (E) protein of Dengue virus forms a dimer on the surface of the mature Dengue virus (FIG. 1). Upon binding to membranes of the host cell, the virus is taken up into endosomes. Acidification within the endosome results in dissociation of the dimer; and the protein rearranges to form a trimer that mediates fusion of viral and host membranes (FIGS. 1-2). Insertion of the tip of E into host membranes is essential to the process, serving to anchor E into the membrane. We examined the interactions between E and lipid membranes by experiments and simulations. Our results show that two important interactions are hydrogen bonds formed between lysines located on the sides of the trimer close to the tip (K246 and K247) and nearby lipid headgroups (FIG. 3A-3F). An arginine (R73 near the fusion loop) also contributes significant hydrogen bonding. Taken together, K246, K247, and R73 establish about 25% of all hydrogen bonds with the lipids. Such strong hydrogen bonding interactions (between lysine or arginine and lipid headgroups) can be more influential and stronger than hydrophobic interactions between the fusion loop and the lipid headgroups.

Figure 4:
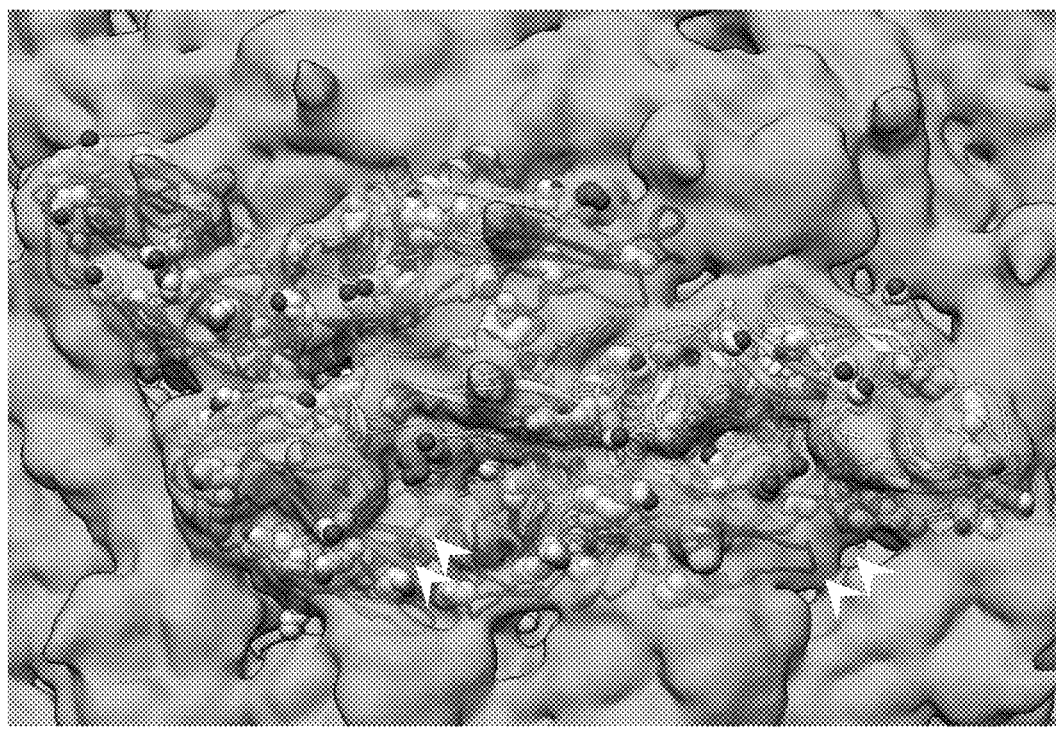
FIG. 4 shows a molecular dynamics simulation image of a E protein (in dimer form) on a virus surface, in which K246 and K247 (arrowheads) are shown to interact most strongly with lipids.

Prior to our work, other researchers had focused on the fusion loop, a hydrophobic region at the tip of the protein and located as position 98-111 of the Dengue virus E protein (see, e.g., position 98-111 of SEQ ID NO: 192 in FIG. 10). Early researchers had postulated that insertion of the fusion loop into the lipid tails anchors the protein into the membrane. In contrast, our work establishes that K246 and K247 are exposed at the surface of the E dimer in the mature virus (FIG. 4) and, therefore, that these amino acids could be a viable drug target to inhibit fusion and, consequently infection, of the virus. Exemplary drugs to inhibit the target can include, e.g., any inhibitors described herein. Either or both lysine at position 246 (K246) and lysine at position 247 (K247) are conserved among other flaviviruses (see, e.g., FIGS. 5-9). Thus, without wishing to be limited by mechanism, such a target could be applicable to a broad range of viruses expected to these conserved residues (e.g., as in flaviviruses, such as any described herein, and including West Nile, Zika, tick-borne encephalitis virus, yellow fever, etc.).

Further methods and data are described in Vanegas J M et al., "Insertion of Dengue E into lipid bilayers studied by neutron reflectivity and molecular dynamics simulations," *BBA Biomembranes* 2018; 1860:1216-1230, which is incorporated herein by reference in its entirety.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method for identifying a candidate therapeutic for a disease caused by a viral envelope protein, the method comprising:

contacting a test envelope protein with a compound, wherein the test protein comprises a first sequence having at least 80% sequence identity to any one of SEQ ID NOs:35-104 or having any one of SEQ ID NOs:105, 106, 179, 181, 182, 185, 187, and 188; wherein the test protein comprises a second sequence having at least 80% sequence identity to any one of SEQ ID NOs: 107-176 or having any one of SEQ ID NOs: 177, 178, 180, 183, 184, 186, and 189-191; and wherein the second sequence comprises a lysine at position 9 and/or position 10; and determining an activity of the compound with the test protein, wherein the activity indicates greater inhibition of viral entry, as compared to a control.

2. The method of claim 1, further comprising, after the determining step:

contacting a mutant viral envelope protein with the compound, wherein the mutant protein comprises the sequence of the test protein with a mutation in the second sequence at position 9 and/or position 10;

determining an activity of the compound with the mutant protein; and comparing the activity of the compound with the test protein and the mutant protein, wherein the activity of the test protein indicates greater inhibition, as compared to the mutant protein.

3. The method of claim 1, wherein the second sequence of the test protein comprises a lysine at positions 9 and 10.

4. The method of claim 1, wherein the mutation in the second sequence at position 9 and/or 10 comprises a glycine, alanine, valine, leucine, isoleucine, methionine, aspartic acid, glutamic acid, asparagine, or glutamine.

5. The method of claim 2, wherein the first sequence of the test protein comprises an arginine at position 30, and wherein the first sequence of the mutant protein comprises a mutation at position 30.

6. The method of claim 5, wherein the mutation in the first sequence at position 30 comprises a glycine, alanine, valine, leucine, isoleucine, methionine, aspartic acid, glutamic acid, asparagine, or glutamine.

7. The method of claim 1, wherein the test protein comprises an arginine at position 30 of the first sequence, a lysine at position 9 of the second sequence, and a lysine at position 10 of the second sequence.

8. The method of claim 2, wherein the mutant protein comprises a mutation at position 30 of the first sequence, at position 9 of the second sequence, and at position 10 of the second sequence.

9. A method for identifying a candidate therapeutic for a disease caused by a viral envelope protein, the method comprising:

contacting a test envelope protein with a compound, wherein the test protein comprises a sequence having at least 80% sequence identity to SEQ ID NO: 192, wherein the sequence comprises an arginine at position 73, an arginine at position 99, a lysine at position 246, and/or a lysine at position 247; and determining an activity of the compound with the test protein, wherein the activity indicates greater inhibition of viral entry, as compared to a control.

10. The method of claim 9, further comprising, after the determining step: determining an activity of the compound with the test protein;

contacting a mutant viral envelope protein with the compound, wherein the mutant protein comprises the sequence of the test protein with at position 73, 99, 246, and/or 247;

determining an activity of the compound with the mutant protein; and comparing the activity of the compound with the test protein and the mutant protein, wherein the activity of the test protein indicates greater inhibition, as compared to the mutant protein.

11. The method of claim 9, wherein the mutation at position 73, 99, 246, and/or 247 comprises a glycine, alanine, valine, leucine, isoleucine, methionine, aspartic acid, glutamic acid, asparagine, or glutamine.

12. The method of claim 9, wherein the test protein comprises a lysine at position 246 and a lysine at position 247.

13. The method of claim 9, wherein the test protein comprises an arginine at position 99.

14. The method of claim 10, wherein the mutant protein comprises a mutation at positions 99, 246, and 247.

15. A method of treating a viral infection in a subject, the method comprising:

administering an effective amount of a lysine inhibitor and/or an arginine inhibitor to the subject, thereby treating the viral infection, wherein the infection arises from a flavivirus.

16. The method of claim 15, wherein the flavivirus is a mosquito-borne virus.

17. The method of claim 15, wherein the flavivirus is an Alkhumra hemorrhagic fever virus, Bussuquara virus, Chaoyang virus, Dengue virus, Donggang virus, Ilheus virus, Japanese encephalitis virus, Kedougou virus, Kokobera virus, Kunjin virus, Kyasanur Forest disease virus, Langat virus, Layer flavivirus, Louping ill virus, Murray Valley encephalitis virus, Omsk hemorrhagic fever virus, Powassan virus, Rocio virus, St. Louis encephalitis virus, tick-borne encephalitis virus, Usutu virus, West Nile virus, and Zika virus.

18. The method of claim 15, wherein the lysine inhibitor is selected from the group consisting of manoalide, secomanoalide, wortmannin, myriocin, carbaglucose-6-phosphate, an aldehyde terpenoid, a wortmannin analogue, a pyrrole-5-carboxaldehyde inhibitor, an alkyl 6-(N-substituted sulfamoyl)cyclohex-1-ene-1-carboxylate compound, a fluorosulfonyl compound, a sulfonyl fluoride probe, a purine-based cyclin-dependent kinase inhibitor, a stilbene compound, an 8-N-benzyl adenosine reversible inhibitor, an adenosine-derived ATP-competitive inhibitor, an indolebased inhibitor, a peptide inhibitor including an unnatural amino acid with aryl sulfonyl fluoride, an iminoboronate compound, and salts thereof.

19. The method of claim 15, wherein the arginine inhibitor is selected from the group consisting of phenylglyoxal, p-azidophenylglyoxal, 2,3-butanedione, 1,2-cyclohexanedione, 5,6,9,10-tetrahydro[1,10]phenanthrolino[2,3-b][1,10]phenanthroline-2,13-dicarboxylic acid, 5,6,9,10-tetrahydrodinaphtho[1,2-b2',1'-g][1,8]-naphthyridine-2,13-dicarboxylic acid, 5,6,9,10-tetrahydrobenzo[7,8]quino[2,3-b][1,10]phenanthroline-2,13-dicarboxylic acid, and salts thereof.

* * * * *

SEQUENCE LISTING

```
<160> NUMBER OF SEQ ID NOS: 207

<210> SEQ ID NO 1
<211> LENGTH: 31
<212> TYPE: PRT
<213> ORGANISM: Artificial Sequence
<220> FEATURE:
<223> OTHER INFORMATION: Synthetic construct

<400> SEQUENCE: 1

Thr Asp Ser Arg Cys Pro Thr Gln Gly Glu Ala Thr Leu Val Glu Glu
1               5                   10                  15

Gln Asp Ala Asn Phe Val Cys Arg Arg Thr Phe Val Asp Arg Gly
            20                  25                  30
```

<210> SEQ ID NO 2
<211> LENGTH: 19
<212> TYPE: PRT
<213> ORGANISM: Artificial Sequence
<220> FEATURE:
<223> OTHER INFORMATION: Synthetic construct

<400> SEQUENCE: 2

Val Thr Phe Lys Thr Ala His Ala Lys Lys Gln Glu Val Val Val Leu
 1               5                  10                  15

Gly Ser Gln

<210> SEQ ID NO 3
<211> LENGTH: 31
<212> TYPE: PRT
<213> ORGANISM: Artificial Sequence
<220> FEATURE:
<223> OTHER INFORMATION: Synthetic construct

<400> SEQUENCE: 3

Thr Asp Ser Arg Cys Pro Thr Gln Gly Glu Pro Ser Leu Asn Glu Glu
 1               5                  10                  15

Gln Asp Lys Arg Phe Val Cys Lys His Ser Met Val Asp Arg Gly
             20                  25                  30

<210> SEQ ID NO 4
<211> LENGTH: 19
<212> TYPE: PRT
<213> ORGANISM: Artificial Sequence
<220> FEATURE:
<223> OTHER INFORMATION: Synthetic construct

<400> SEQUENCE: 4

Val Thr Phe Lys Asn Pro His Ala Lys Lys Gln Asp Val Val Val Leu
 1               5                  10                  15

Gly Ser Gln

<210> SEQ ID NO 5
<211> LENGTH: 31
<212> TYPE: PRT
<213> ORGANISM: Artificial Sequence
<220> FEATURE:
<223> OTHER INFORMATION: Synthetic construct

<400> SEQUENCE: 5

Thr Asp Ser Arg Cys Pro Thr Gln Gly Glu Ala Val Leu Pro Glu Glu
 1               5                  10                  15

Gln Asp Gln Asn Tyr Val Cys Lys His Thr Tyr Val Asp Arg Gly
             20                  25                  30

<210> SEQ ID NO 6
<211> LENGTH: 19
<212> TYPE: PRT
<213> ORGANISM: Artificial Sequence
<220> FEATURE:
<223> OTHER INFORMATION: Synthetic construct

<400> SEQUENCE: 6

Val Thr Phe Lys Asn Ala His Ala Lys Lys Gln Glu Val Val Val Leu
 1               5                  10                  15

Gly Ser Gln

<210> SEQ ID NO 7

```
<211> LENGTH: 31
<212> TYPE: PRT
<213> ORGANISM: Artificial Sequence
<220> FEATURE:
<223> OTHER INFORMATION: Synthetic construct

<400> SEQUENCE: 7

Thr Ala Thr Arg Cys Pro Thr Gln Gly Glu Pro Tyr Leu Lys Glu Glu
1               5                   10                  15

Gln Asp Gln Gln Tyr Ile Cys Arg Arg Asp Val Val Asp Arg Gly
            20                  25                  30

<210> SEQ ID NO 8
<211> LENGTH: 19
<212> TYPE: PRT
<213> ORGANISM: Artificial Sequence
<220> FEATURE:
<223> OTHER INFORMATION: Synthetic construct

<400> SEQUENCE: 8

Val Thr Phe Lys Val Pro His Ala Lys Arg Gln Asp Val Thr Val Leu
1               5                   10                  15

Gly Ser Gln

<210> SEQ ID NO 9
<211> LENGTH: 31
<212> TYPE: PRT
<213> ORGANISM: Artificial Sequence
<220> FEATURE:
<223> OTHER INFORMATION: Synthetic construct

<400> SEQUENCE: 9

Val Glu Ala Arg Cys Pro Thr Thr Gly Pro Ala Thr Leu Pro Glu Glu
1               5                   10                  15

His Gln Ala Asn Met Val Cys Lys Arg Asp Gln Ser Asp Arg Gly
            20                  25                  30

<210> SEQ ID NO 10
<211> LENGTH: 19
<212> TYPE: PRT
<213> ORGANISM: Artificial Sequence
<220> FEATURE:
<223> OTHER INFORMATION: Synthetic construct

<400> SEQUENCE: 10

Val Glu Phe Gly Pro Pro His Ala Val Lys Met Asp Ile Phe Asn Leu
1               5                   10                  15

Gly Asp Gln

<210> SEQ ID NO 11
<211> LENGTH: 31
<212> TYPE: PRT
<213> ORGANISM: Artificial Sequence
<220> FEATURE:
<223> OTHER INFORMATION: Synthetic construct

<400> SEQUENCE: 11

Ser Thr Asp Val Cys Pro Gly Gly Ser Gln Leu Asn Met Gly Glu Ile
1               5                   10                  15

Asn Gly Lys Glu Arg Val Cys Ser Thr Gln Pro Tyr Asn Arg Gly
            20                  25                  30

<210> SEQ ID NO 12
<211> LENGTH: 19
```

<212> TYPE: PRT
<213> ORGANISM: Artificial Sequence
<220> FEATURE:
<223> OTHER INFORMATION: Synthetic construct

<400> SEQUENCE: 12

```
Val Val Trp Gly Asp Ala Arg Ala Asn Glu Val Leu Val Lys Asn Ile
1               5                   10                  15

Leu Glu Pro
```

<210> SEQ ID NO 13
<211> LENGTH: 31
<212> TYPE: PRT
<213> ORGANISM: Artificial Sequence
<220> FEATURE:
<223> OTHER INFORMATION: Synthetic construct

<400> SEQUENCE: 13

```
Val Val Ala Arg Cys Pro Ala Met Gly Pro Ala Thr Leu Pro Glu Glu
1               5                   10                  15

His Gln Ala Ser Thr Val Cys Arg Arg Asp Gln Ser Asp Arg Gly
            20                  25                  30
```

<210> SEQ ID NO 14
<211> LENGTH: 19
<212> TYPE: PRT
<213> ORGANISM: Artificial Sequence
<220> FEATURE:
<223> OTHER INFORMATION: Synthetic construct

<400> SEQUENCE: 14

```
Val Glu Phe Gly Glu Pro His Ala Val Lys Met Asp Ile Tyr Asn Leu
1               5                   10                  15

Gly Asp Gln
```

<210> SEQ ID NO 15
<211> LENGTH: 31
<212> TYPE: PRT
<213> ORGANISM: Artificial Sequence
<220> FEATURE:
<223> OTHER INFORMATION: Synthetic construct

<400> SEQUENCE: 15

```
Ile Asn Asp Arg Cys Pro Ser Thr Gly Glu Ala His Leu Val Glu Glu
1               5                   10                  15

Asn Glu Gly Asp Asn Ala Cys Lys Arg Thr Tyr Ser Asp Arg Gly
            20                  25                  30
```

<210> SEQ ID NO 16
<211> LENGTH: 19
<212> TYPE: PRT
<213> ORGANISM: Artificial Sequence
<220> FEATURE:
<223> OTHER INFORMATION: Synthetic construct

<400> SEQUENCE: 16

```
Val Glu Phe Glu Pro Pro His Ala Ala Thr Ile Arg Asx Leu Ala Leu
1               5                   10                  15

Gly Asn Gln
```

<210> SEQ ID NO 17
<211> LENGTH: 31
<212> TYPE: PRT
<213> ORGANISM: Artificial Sequence

```
<220> FEATURE:
<223> OTHER INFORMATION: Synthetic construct

<400> SEQUENCE: 17

Val Ala Ala Arg Cys Pro Thr Met Gly Pro Ala Thr Leu Ala Glu Glu
1               5                   10                  15

His Gln Ser Gly Thr Val Cys Lys Arg Asp Gln Ser Asp Arg Gly
            20                  25                  30

<210> SEQ ID NO 18
<211> LENGTH: 19
<212> TYPE: PRT
<213> ORGANISM: Artificial Sequence
<220> FEATURE:
<223> OTHER INFORMATION: Synthetic construct

<400> SEQUENCE: 18

Val Glu Phe Gly Ala Pro His Ala Val Lys Met Asp Val Tyr Asn Leu
1               5                   10                  15

Gly Asp Gln

<210> SEQ ID NO 19
<211> LENGTH: 31
<212> TYPE: PRT
<213> ORGANISM: Artificial Sequence
<220> FEATURE:
<223> OTHER INFORMATION: Synthetic construct

<400> SEQUENCE: 19

Thr Val Ala Arg Cys Pro Thr Thr Gly Glu Ala His Asn Thr Lys Arg
1               5                   10                  15

Ser Asp Pro Thr Phe Val Cys Lys Arg Asp Val Val Asp Arg Gly
            20                  25                  30

<210> SEQ ID NO 20
<211> LENGTH: 19
<212> TYPE: PRT
<213> ORGANISM: Artificial Sequence
<220> FEATURE:
<223> OTHER INFORMATION: Synthetic construct

<400> SEQUENCE: 20

Val Glu Phe Glu Glu Pro His Ala Thr Lys Gln Thr Val Val Ala Leu
1               5                   10                  15

Gly Ser Gln

<210> SEQ ID NO 21
<211> LENGTH: 31
<212> TYPE: PRT
<213> ORGANISM: Artificial Sequence
<220> FEATURE:
<223> OTHER INFORMATION: Synthetic construct

<400> SEQUENCE: 21

Thr Lys Ala Ala Cys Pro Thr Met Gly Glu Ala His Asn Glu Lys Arg
1               5                   10                  15

Ala Asp Pro Ala Phe Val Cys Lys Gln Gly Val Val Asp Arg Gly
            20                  25                  30

<210> SEQ ID NO 22
<211> LENGTH: 19
<212> TYPE: PRT
<213> ORGANISM: Artificial Sequence
<220> FEATURE:
```

```
<223> OTHER INFORMATION: Synthetic construct

<400> SEQUENCE: 22

Met Glu Phe Glu Glu Pro His Ala Thr Lys Gln Ser Val Val Ala Leu
1               5                   10                  15

Gly Ser Gln

<210> SEQ ID NO 23
<211> LENGTH: 31
<212> TYPE: PRT
<213> ORGANISM: Artificial Sequence
<220> FEATURE:
<223> OTHER INFORMATION: Synthetic construct

<400> SEQUENCE: 23

Thr Lys Ala Ala Cys Pro Thr Met Gly Glu Ala His Asn Asp Lys Arg
1               5                   10                  15

Ala Asp Pro Ser Phe Val Cys Lys Gln Gly Val Val Asp Arg Gly
            20                  25                  30

<210> SEQ ID NO 24
<211> LENGTH: 19
<212> TYPE: PRT
<213> ORGANISM: Artificial Sequence
<220> FEATURE:
<223> OTHER INFORMATION: Synthetic construct

<400> SEQUENCE: 24

Met Glu Phe Glu Glu Pro His Ala Thr Lys Gln Ser Ile Val Ala Leu
1               5                   10                  15

Gly Ser Gln

<210> SEQ ID NO 25
<211> LENGTH: 31
<212> TYPE: PRT
<213> ORGANISM: Artificial Sequence
<220> FEATURE:
<223> OTHER INFORMATION: Synthetic construct

<400> SEQUENCE: 25

Val Glu Ser Gly Cys Pro Gly Thr Asp Glu Ile His Asn Thr Lys Ala
1               5                   10                  15

Lys Asp Thr Ser Tyr Met Cys Lys Val Ser Tyr Pro Arg Gly
            20                  25                  30

<210> SEQ ID NO 26
<211> LENGTH: 19
<212> TYPE: PRT
<213> ORGANISM: Artificial Sequence
<220> FEATURE:
<223> OTHER INFORMATION: Synthetic construct

<400> SEQUENCE: 26

Val Glu Phe Gly Val Pro His Ala Thr Arg Gln Ser Val Tyr Ser Ile
1               5                   10                  15

Gly Asp Gln

<210> SEQ ID NO 27
<211> LENGTH: 31
<212> TYPE: PRT
<213> ORGANISM: Artificial Sequence
<220> FEATURE:
<223> OTHER INFORMATION: Synthetic construct
```

<400> SEQUENCE: 27

Thr Val Ser Asn Cys Pro Thr Thr Gly Glu Ala His Asn Pro Lys Arg
1               5                   10                  15

Ala Glu Asp Thr Tyr Val Cys Lys Ser Gly Val Thr Asp Arg Gly
                20                  25                  30

<210> SEQ ID NO 28
<211> LENGTH: 19
<212> TYPE: PRT
<213> ORGANISM: Artificial Sequence
<220> FEATURE:
<223> OTHER INFORMATION: Synthetic construct

<400> SEQUENCE: 28

Leu Glu Phe Glu Glu Pro His Ala Thr Lys Gln Ser Val Val Ala Leu
1               5                   10                  15

Gly Ser Gln

<210> SEQ ID NO 29
<211> LENGTH: 31
<212> TYPE: PRT
<213> ORGANISM: Artificial Sequence
<220> FEATURE:
<223> OTHER INFORMATION: Synthetic construct

<400> SEQUENCE: 29

Ser Val Asn Gly Cys Pro Ser Thr Glu Ala His Asn Asp Lys Arg
1               5                   10                  15

Lys Asp Ser Thr Tyr Leu Cys Glu Arg Ser Tyr Pro Ala Arg Gly
                20                  25                  30

<210> SEQ ID NO 30
<211> LENGTH: 19
<212> TYPE: PRT
<213> ORGANISM: Artificial Sequence
<220> FEATURE:
<223> OTHER INFORMATION: Synthetic construct

<400> SEQUENCE: 30

Val Glu Phe Ser Thr Pro His Ala Thr Lys Gln Ser Val Tyr Thr Leu
1               5                   10                  15

Gly Asp Gln

<210> SEQ ID NO 31
<211> LENGTH: 31
<212> TYPE: PRT
<213> ORGANISM: Artificial Sequence
<220> FEATURE:
<223> OTHER INFORMATION: Synthetic construct

<400> SEQUENCE: 31

Thr Val Ala Arg Cys Pro Thr Thr Gly Glu Ala His Asn Glu Lys Arg
1               5                   10                  15

Ala Asp Ser Ser Tyr Val Cys Lys Gln Gly Phe Thr Asp Arg Gly
                20                  25                  30

<210> SEQ ID NO 32
<211> LENGTH: 19
<212> TYPE: PRT
<213> ORGANISM: Artificial Sequence
<220> FEATURE:
<223> OTHER INFORMATION: Synthetic construct

<400> SEQUENCE: 32

```
Met Glu Phe Glu Glu Ala His Ala Thr Lys Gln Ser Val Val Ala Leu
1               5                   10                  15

Gly Ser Gln
```

<210> SEQ ID NO 33
<211> LENGTH: 31
<212> TYPE: PRT
<213> ORGANISM: Artificial Sequence
<220> FEATURE:
<223> OTHER INFORMATION: Synthetic construct

<400> SEQUENCE: 33

```
Ser Asp Ser Arg Cys Pro Thr Gln Gly Glu Ala Tyr Leu Asp Lys Gln
1               5                   10                  15

Ser Asp Thr Gln Tyr Val Cys Lys Arg Thr Leu Val Asp Arg Gly
            20                  25                  30
```

<210> SEQ ID NO 34
<211> LENGTH: 19
<212> TYPE: PRT
<213> ORGANISM: Artificial Sequence
<220> FEATURE:
<223> OTHER INFORMATION: Synthetic construct

<400> SEQUENCE: 34

```
Val Glu Phe Lys Asp Ala His Ala Lys Arg Gln Thr Val Val Leu
1               5                   10                  15

Gly Ser Gln
```

<210> SEQ ID NO 35
<211> LENGTH: 31
<212> TYPE: PRT
<213> ORGANISM: Artificial Sequence
<220> FEATURE:
<223> OTHER INFORMATION: Synthetic construct

<400> SEQUENCE: 35

```
Thr Asp Ser Arg Cys Pro Thr Gln Gly Glu Ala Thr Leu Val Glu Glu
1               5                   10                  15

Gln Asp Ala Asn Phe Val Cys Arg Arg Thr Phe Val Asp Arg Gly
            20                  25                  30
```

<210> SEQ ID NO 36
<211> LENGTH: 31
<212> TYPE: PRT
<213> ORGANISM: Artificial Sequence
<220> FEATURE:
<223> OTHER INFORMATION: Synthetic construct

<400> SEQUENCE: 36

```
Thr Asp Ser Arg Cys Pro Thr Gln Gly Glu Ala Thr Leu Val Glu Glu
1               5                   10                  15

Gln Asp Ala Asn Phe Val Cys Arg Arg Thr Phe Val Asp Arg Gly
            20                  25                  30
```

<210> SEQ ID NO 37
<211> LENGTH: 31
<212> TYPE: PRT
<213> ORGANISM: Artificial Sequence
<220> FEATURE:
<223> OTHER INFORMATION: Synthetic construct

<400> SEQUENCE: 37

```
Thr Asp Ser Arg Cys Pro Thr Gln Gly Glu Ala Thr Leu Val Glu Glu
1               5                   10                  15

Gln Asp Thr Asn Phe Val Cys Arg Arg Thr Phe Val Asp Arg Gly
            20                  25                  30

<210> SEQ ID NO 38
<211> LENGTH: 31
<212> TYPE: PRT
<213> ORGANISM: Artificial Sequence
<220> FEATURE:
<223> OTHER INFORMATION: Synthetic construct

<400> SEQUENCE: 38

Thr Asp Ser Arg Cys Pro Thr Gln Gly Glu Ala Thr Leu Val Glu Glu
1               5                   10                  15

Gln Asp Ala Asn Phe Val Cys Arg Arg Thr Phe Val Asp Arg Gly
            20                  25                  30

<210> SEQ ID NO 39
<211> LENGTH: 31
<212> TYPE: PRT
<213> ORGANISM: Artificial Sequence
<220> FEATURE:
<223> OTHER INFORMATION: Synthetic construct

<400> SEQUENCE: 39

Thr Asp Ser Arg Cys Pro Thr Gln Gly Glu Ala Thr Leu Val Glu Glu
1               5                   10                  15

Gln Asp Thr Asn Phe Val Cys Arg Arg Thr Phe Val Asp Arg Gly
            20                  25                  30

<210> SEQ ID NO 40
<211> LENGTH: 31
<212> TYPE: PRT
<213> ORGANISM: Artificial Sequence
<220> FEATURE:
<223> OTHER INFORMATION: Synthetic construct

<400> SEQUENCE: 40

Thr Glu Ser Arg Cys Pro Thr Gln Gly Glu Pro Ser Leu Asn Glu Glu
1               5                   10                  15

Gln Asp Lys Arg Phe Val Cys Lys His Ser Met Val Asp Arg Gly
            20                  25                  30

<210> SEQ ID NO 41
<211> LENGTH: 31
<212> TYPE: PRT
<213> ORGANISM: Artificial Sequence
<220> FEATURE:
<223> OTHER INFORMATION: Synthetic construct

<400> SEQUENCE: 41

Thr Glu Ser Arg Cys Pro Thr Leu Gly Glu Pro Ser Leu Asn Glu Glu
1               5                   10                  15

Gln Asp Lys Arg Leu Val Cys Lys His Ser Met Val Asp Arg Gly
            20                  25                  30

<210> SEQ ID NO 42
<211> LENGTH: 31
<212> TYPE: PRT
<213> ORGANISM: Artificial Sequence
<220> FEATURE:
<223> OTHER INFORMATION: Synthetic construct

<400> SEQUENCE: 42
```

```
Thr Glu Ser Arg Cys Pro Thr Gln Gly Glu Pro Ser Leu Asn Glu Glu
1               5                   10                  15

Gln Asp Lys Arg Phe Val Cys Lys His Ser Met Val Asp Arg Gly
            20                  25                  30
```

<210> SEQ ID NO 43
<211> LENGTH: 31
<212> TYPE: PRT
<213> ORGANISM: Artificial Sequence
<220> FEATURE:
<223> OTHER INFORMATION: Synthetic construct

<400> SEQUENCE: 43

```
Thr Glu Ser Arg Cys Pro Thr Gln Gly Glu Pro Ser Leu Asn Glu Glu
1               5                   10                  15

Gln Asp Lys Arg Phe Val Cys Lys His Ser Met Val Asp Arg Gly
            20                  25                  30
```

<210> SEQ ID NO 44
<211> LENGTH: 31
<212> TYPE: PRT
<213> ORGANISM: Artificial Sequence
<220> FEATURE:
<223> OTHER INFORMATION: Synthetic construct

<400> SEQUENCE: 44

```
Thr Glu Ser Arg Cys Pro Thr Gln Gly Glu Pro Ser Leu Asn Glu Glu
1               5                   10                  15

Gln Asp Lys Arg Phe Val Cys Lys His Ser Met Val Asp Arg Gly
            20                  25                  30
```

<210> SEQ ID NO 45
<211> LENGTH: 31
<212> TYPE: PRT
<213> ORGANISM: Artificial Sequence
<220> FEATURE:
<223> OTHER INFORMATION: Synthetic construct

<400> SEQUENCE: 45

```
Thr Glu Ser Arg Cys Pro Thr Gln Gly Glu Pro Ser Leu Asn Glu Glu
1               5                   10                  15

Gln Asp Lys Arg Phe Leu Cys Lys His Ser Met Val Asp Arg Gly
            20                  25                  30
```

<210> SEQ ID NO 46
<211> LENGTH: 31
<212> TYPE: PRT
<213> ORGANISM: Artificial Sequence
<220> FEATURE:
<223> OTHER INFORMATION: Synthetic construct

<400> SEQUENCE: 46

```
Thr Asp Ser Arg Cys Pro Thr Gln Gly Glu Pro Thr Leu Asn Glu Glu
1               5                   10                  15

Gln Asp Lys Arg Phe Val Cys Lys His Ser Met Val Asp Arg Gly
            20                  25                  30
```

<210> SEQ ID NO 47
<211> LENGTH: 31
<212> TYPE: PRT
<213> ORGANISM: Artificial Sequence
<220> FEATURE:
<223> OTHER INFORMATION: Synthetic construct

```
<400> SEQUENCE: 47

Thr Asp Ser Arg Cys Pro Thr Gln Gly Glu Pro Thr Leu Asn Glu Glu
1               5                   10                  15

Gln Asp Lys Arg Phe Val Cys Lys His Ser Met Val Asp Arg Gly
            20                  25                  30

<210> SEQ ID NO 48
<211> LENGTH: 31
<212> TYPE: PRT
<213> ORGANISM: Artificial Sequence
<220> FEATURE:
<223> OTHER INFORMATION: Synthetic construct

<400> SEQUENCE: 48

Thr Glu Ser Arg Cys Pro Thr Gln Gly Glu Pro Ser Leu Asn Glu Glu
1               5                   10                  15

Gln Asp Lys Arg Phe Val Cys Lys His Ser Met Val Asp Arg Gly
            20                  25                  30

<210> SEQ ID NO 49
<211> LENGTH: 31
<212> TYPE: PRT
<213> ORGANISM: Artificial Sequence
<220> FEATURE:
<223> OTHER INFORMATION: Synthetic construct

<400> SEQUENCE: 49

Thr Asp Ser Arg Cys Pro Thr Gln Gly Glu Pro Ser Leu Asn Glu Glu
1               5                   10                  15

Gln Asp Lys Arg Phe Val Cys Lys His Ser Met Val Asp Arg Gly
            20                  25                  30

<210> SEQ ID NO 50
<211> LENGTH: 31
<212> TYPE: PRT
<213> ORGANISM: Artificial Sequence
<220> FEATURE:
<223> OTHER INFORMATION: Synthetic construct

<400> SEQUENCE: 50

Thr Glu Ser Arg Cys Pro Thr Gln Gly Glu Pro Ser Leu Asn Glu Glu
1               5                   10                  15

Gln Asp Lys Arg Phe Val Cys Lys His Ser Met Val Asp Arg Gly
            20                  25                  30

<210> SEQ ID NO 51
<211> LENGTH: 31
<212> TYPE: PRT
<213> ORGANISM: Artificial Sequence
<220> FEATURE:
<223> OTHER INFORMATION: Synthetic construct

<400> SEQUENCE: 51

Thr Glu Ser Arg Cys Pro Ile Gln Gly Glu Pro Ser Leu Asn Glu Glu
1               5                   10                  15

Gln Asp Lys Arg Phe Val Cys Lys His Ser Met Val Asp Arg Gly
            20                  25                  30

<210> SEQ ID NO 52
<211> LENGTH: 31
<212> TYPE: PRT
<213> ORGANISM: Artificial Sequence
<220> FEATURE:
<223> OTHER INFORMATION: Synthetic construct
```

<400> SEQUENCE: 52

Thr Asp Ser Arg Cys Pro Thr Gln Gly Glu Pro Thr Leu Asn Glu Glu
1               5                   10                  15
Gln Asp Lys Arg Phe Val Cys Lys His Ser Met Val Asp Arg Gly
            20                  25                  30

<210> SEQ ID NO 53
<211> LENGTH: 31
<212> TYPE: PRT
<213> ORGANISM: Artificial Sequence
<220> FEATURE:
<223> OTHER INFORMATION: Synthetic construct

<400> SEQUENCE: 53

Thr Asp Ser Arg Cys Pro Thr Gln Gly Glu Ala Ile Leu Pro Glu Glu
1               5                   10                  15
Gln Asp Gln Asn Tyr Val Cys Lys His Thr Tyr Val Asp Arg Gly
            20                  25                  30

<210> SEQ ID NO 54
<211> LENGTH: 31
<212> TYPE: PRT
<213> ORGANISM: Artificial Sequence
<220> FEATURE:
<223> OTHER INFORMATION: Synthetic construct

<400> SEQUENCE: 54

Thr Asp Ser Arg Cys Pro Thr Gln Gly Glu Ala Val Leu Pro Glu Glu
1               5                   10                  15
Gln Asp Gln Asn Tyr Val Cys Lys His Thr Tyr Val Asp Arg Gly
            20                  25                  30

<210> SEQ ID NO 55
<211> LENGTH: 31
<212> TYPE: PRT
<213> ORGANISM: Artificial Sequence
<220> FEATURE:
<223> OTHER INFORMATION: Synthetic construct

<400> SEQUENCE: 55

Thr Asp Ser Arg Cys Pro Thr Gln Gly Glu Ala Ile Leu Pro Glu Glu
1               5                   10                  15
Gln Asp Gln Asn Tyr Val Cys Lys His Thr Tyr Val Asp Arg Gly
            20                  25                  30

<210> SEQ ID NO 56
<211> LENGTH: 31
<212> TYPE: PRT
<213> ORGANISM: Artificial Sequence
<220> FEATURE:
<223> OTHER INFORMATION: Synthetic construct

<400> SEQUENCE: 56

Thr Asp Ser Arg Cys Pro Thr Gln Gly Glu Ala Ile Leu Pro Glu Glu
1               5                   10                  15
Gln Asp Gln Asn Tyr Val Cys Lys His Thr Tyr Val Asp Arg Gly
            20                  25                  30

<210> SEQ ID NO 57
<211> LENGTH: 31
<212> TYPE: PRT
<213> ORGANISM: Artificial Sequence
<220> FEATURE:

<223> OTHER INFORMATION: Synthetic construct

<400> SEQUENCE: 57

Thr Asp Ser Arg Cys Pro Thr Gln Gly Glu Ala Val Leu Pro Glu Glu
1               5                   10                  15

Gln Asp Gln Asn Tyr Val Cys Lys His Thr Tyr Val Asp Arg Gly
            20                  25                  30

<210> SEQ ID NO 58
<211> LENGTH: 31
<212> TYPE: PRT
<213> ORGANISM: Artificial Sequence
<220> FEATURE:
<223> OTHER INFORMATION: Synthetic construct

<400> SEQUENCE: 58

Thr Ala Thr Arg Cys Pro Thr Gln Gly Glu Pro Tyr Leu Lys Glu Glu
1               5                   10                  15

Gln Asp Gln Gln Tyr Ile Cys Arg Arg Asp Val Val Asp Arg Gly
            20                  25                  30

<210> SEQ ID NO 59
<211> LENGTH: 31
<212> TYPE: PRT
<213> ORGANISM: Artificial Sequence
<220> FEATURE:
<223> OTHER INFORMATION: Synthetic construct

<400> SEQUENCE: 59

Thr Ala Thr Arg Cys Pro Thr Gln Gly Glu Pro Tyr Leu Lys Glu Glu
1               5                   10                  15

Gln Asp Gln Gln Tyr Ile Cys Arg Arg Asp Val Val Asp Arg Gly
            20                  25                  30

<210> SEQ ID NO 60
<211> LENGTH: 31
<212> TYPE: PRT
<213> ORGANISM: Artificial Sequence
<220> FEATURE:
<223> OTHER INFORMATION: Synthetic construct

<400> SEQUENCE: 60

Thr Ala Thr Arg Cys Pro Thr Gln Gly Glu Pro Tyr Leu Lys Glu Glu
1               5                   10                  15

Gln Asp Gln Gln Tyr Ile Cys Arg Arg Asp Val Val Asp Arg Gly
            20                  25                  30

<210> SEQ ID NO 61
<211> LENGTH: 31
<212> TYPE: PRT
<213> ORGANISM: Artificial Sequence
<220> FEATURE:
<223> OTHER INFORMATION: Synthetic construct

<400> SEQUENCE: 61

Thr Ala Thr Arg Cys Pro Thr Gln Gly Glu Pro Tyr Leu Lys Glu Glu
1               5                   10                  15

Gln Asp Gln Gln Tyr Ile Cys Arg Arg Asp Met Val Asp Arg Gly
            20                  25                  30

<210> SEQ ID NO 62
<211> LENGTH: 31
<212> TYPE: PRT
<213> ORGANISM: Artificial Sequence
<220> FEATURE:
<223> OTHER INFORMATION: Synthetic construct

<400> SEQUENCE: 62

Thr Ala Thr Arg Cys Pro Thr Gln Gly Glu Pro Tyr Leu Lys Glu Glu
1               5                   10                  15

Gln Asp Gln Gln Tyr Ile Cys Arg Arg Asp Val Val Asp Arg Gly
            20                  25                  30

<210> SEQ ID NO 63
<211> LENGTH: 31
<212> TYPE: PRT
<213> ORGANISM: Artificial Sequence
<220> FEATURE:
<223> OTHER INFORMATION: Synthetic construct

<400> SEQUENCE: 63

Thr Arg Ala Ala Cys Pro Thr Met Gly Glu Ala His Asn Glu Lys Arg
1               5                   10                  15

Ala Asp Pro Ala Phe Val Cys Lys Gln Gly Val Val Asp Arg Gly
            20                  25                  30

<210> SEQ ID NO 64
<211> LENGTH: 31
<212> TYPE: PRT
<213> ORGANISM: Artificial Sequence
<220> FEATURE:
<223> OTHER INFORMATION: Synthetic construct

<400> SEQUENCE: 64

Thr Lys Ala Ala Cys Pro Thr Met Gly Glu Ala His Asn Asp Lys Arg
1               5                   10                  15

Ala Asp Pro Ala Phe Val Cys Arg Gln Gly Val Val Asp Arg Gly
            20                  25                  30

<210> SEQ ID NO 65
<211> LENGTH: 31
<212> TYPE: PRT
<213> ORGANISM: Artificial Sequence
<220> FEATURE:
<223> OTHER INFORMATION: Synthetic construct

<400> SEQUENCE: 65

Thr Lys Ala Ala Cys Pro Thr Met Gly Glu Ala His Asn Asp Lys Arg
1               5                   10                  15

Ala Asp Pro Ser Phe Val Cys Lys Gln Gly Val Val Asp Arg Gly
            20                  25                  30

<210> SEQ ID NO 66
<211> LENGTH: 31
<212> TYPE: PRT
<213> ORGANISM: Artificial Sequence
<220> FEATURE:
<223> OTHER INFORMATION: Synthetic construct

<400> SEQUENCE: 66

Thr Val Ala Arg Cys Pro Thr Thr Gly Glu Ala His Asn Glu Lys Arg
1               5                   10                  15

Ala Asp Ser Ser Tyr Val Cys Lys Gln Gly Phe Thr Asp Arg Gly
            20                  25                  30

<210> SEQ ID NO 67
<211> LENGTH: 31
<212> TYPE: PRT

```
<213> ORGANISM: Artificial Sequence
<220> FEATURE:
<223> OTHER INFORMATION: Synthetic construct

<400> SEQUENCE: 67

Thr Val Ala Arg Cys Pro Thr Thr Gly Glu Ala His Asn Glu Lys Arg
1               5                   10                  15

Ala Asp Ser Ser Tyr Val Cys Lys Gln Gly Phe Thr Asp Arg Gly
            20                  25                  30

<210> SEQ ID NO 68
<211> LENGTH: 31
<212> TYPE: PRT
<213> ORGANISM: Artificial Sequence
<220> FEATURE:
<223> OTHER INFORMATION: Synthetic construct

<400> SEQUENCE: 68

Thr Val Ala Arg Cys Pro Thr Thr Gly Glu Ala His Asn Thr Lys Arg
1               5                   10                  15

Ser Asp Pro Thr Phe Val Cys Lys Arg Asp Val Val Asp Arg Gly
            20                  25                  30

<210> SEQ ID NO 69
<211> LENGTH: 31
<212> TYPE: PRT
<213> ORGANISM: Artificial Sequence
<220> FEATURE:
<223> OTHER INFORMATION: Synthetic construct

<400> SEQUENCE: 69

Ile Asp Asp Lys Cys Pro Ser Thr Gly Glu Ala His Leu Ala Glu Glu
1               5                   10                  15

Asn Glu Gly Asp Asn Ala Cys Lys Arg Thr Tyr Ser Asp Arg Gly
            20                  25                  30

<210> SEQ ID NO 70
<211> LENGTH: 31
<212> TYPE: PRT
<213> ORGANISM: Artificial Sequence
<220> FEATURE:
<223> OTHER INFORMATION: Synthetic construct

<400> SEQUENCE: 70

Ile Asn Asp Lys Cys Pro Ser Thr Gly Glu Ala His Leu Ala Glu Glu
1               5                   10                  15

Asn Asp Gly Asp Asn Ala Cys Lys Arg Thr Tyr Ser Asp Arg Gly
            20                  25                  30

<210> SEQ ID NO 71
<211> LENGTH: 31
<212> TYPE: PRT
<213> ORGANISM: Artificial Sequence
<220> FEATURE:
<223> OTHER INFORMATION: Synthetic construct

<400> SEQUENCE: 71

Ile Asn Asp Lys Cys Pro Ser Thr Gly Glu Ala His Leu Ala Glu Glu
1               5                   10                  15

Asn Asp Gly Asp Asn Ala Cys Lys Arg Thr Tyr Ser Asp Arg Gly
            20                  25                  30

<210> SEQ ID NO 72
<211> LENGTH: 31
```

```
<212> TYPE: PRT
<213> ORGANISM: Artificial Sequence
<220> FEATURE:
<223> OTHER INFORMATION: Synthetic construct

<400> SEQUENCE: 72

Ile Asn Asp Lys Cys Pro Ser Thr Gly Glu Ala His Leu Ala Glu Glu
1               5                   10                  15

Asn Glu Gly Asp Asn Ala Cys Lys Arg Thr Tyr Ser Asp Arg Gly
            20                  25                  30

<210> SEQ ID NO 73
<211> LENGTH: 31
<212> TYPE: PRT
<213> ORGANISM: Artificial Sequence
<220> FEATURE:
<223> OTHER INFORMATION: Synthetic construct

<400> SEQUENCE: 73

Ile Asn Asp Lys Cys Pro Ser Thr Gly Glu Ala His Leu Ala Glu Glu
1               5                   10                  15

Asn Glu Gly Asp Asn Ala Cys Lys Arg Thr Tyr Ser Asp Arg Gly
            20                  25                  30

<210> SEQ ID NO 74
<211> LENGTH: 31
<212> TYPE: PRT
<213> ORGANISM: Artificial Sequence
<220> FEATURE:
<223> OTHER INFORMATION: Synthetic construct

<400> SEQUENCE: 74

Ile Asn Asp Lys Cys Pro Ser Thr Gly Glu Ala His Leu Ala Glu Glu
1               5                   10                  15

Asn Glu Gly Asp His Ala Cys Lys Arg Thr Tyr Ser Asp Arg Gly
            20                  25                  30

<210> SEQ ID NO 75
<211> LENGTH: 31
<212> TYPE: PRT
<213> ORGANISM: Artificial Sequence
<220> FEATURE:
<223> OTHER INFORMATION: Synthetic construct

<400> SEQUENCE: 75

Ile Asn Asp Lys Cys Pro Ser Thr Gly Glu Ala His Leu Ala Glu Glu
1               5                   10                  15

Asn Asp Gly Asp Asn Ala Cys Lys Arg Thr Tyr Ser Asp Arg Gly
            20                  25                  30

<210> SEQ ID NO 76
<211> LENGTH: 31
<212> TYPE: PRT
<213> ORGANISM: Artificial Sequence
<220> FEATURE:
<223> OTHER INFORMATION: Synthetic construct

<400> SEQUENCE: 76

Ile Asn Asp Lys Cys Pro Ser Thr Gly Glu Ala His Leu Ala Glu Glu
1               5                   10                  15

Asn Glu Gly Asp Asn Ala Cys Lys Arg Thr Tyr Ser Asp Arg Gly
            20                  25                  30

<210> SEQ ID NO 77
```

```
<211> LENGTH: 31
<212> TYPE: PRT
<213> ORGANISM: Artificial Sequence
<220> FEATURE:
<223> OTHER INFORMATION: Synthetic construct

<400> SEQUENCE: 77

Ile Asn Asp Lys Cys Pro Ser Thr Gly Glu Ala His Leu Ala Glu Glu
1               5                   10                  15

Asn Glu Gly Asp Asn Ala Cys Lys Arg Thr Tyr Ser Asp Arg Gly
            20                  25                  30

<210> SEQ ID NO 78
<211> LENGTH: 31
<212> TYPE: PRT
<213> ORGANISM: Artificial Sequence
<220> FEATURE:
<223> OTHER INFORMATION: Synthetic construct

<400> SEQUENCE: 78

Ile Asn Asp Lys Cys Pro Ser Thr Gly Glu Ala His Leu Ala Glu Glu
1               5                   10                  15

Asn Glu Gly Asp Asn Ala Cys Lys Arg Thr Tyr Ser Asp Arg Gly
            20                  25                  30

<210> SEQ ID NO 79
<211> LENGTH: 31
<212> TYPE: PRT
<213> ORGANISM: Artificial Sequence
<220> FEATURE:
<223> OTHER INFORMATION: Synthetic construct

<400> SEQUENCE: 79

Ser Asp Ser Arg Cys Pro Thr Gln Gly Glu Ala Tyr Leu Asp Lys Gln
1               5                   10                  15

Ser Asp Thr Gln Tyr Val Cys Lys Arg Thr Leu Val Asp Arg Gly
            20                  25                  30

<210> SEQ ID NO 80
<211> LENGTH: 31
<212> TYPE: PRT
<213> ORGANISM: Artificial Sequence
<220> FEATURE:
<223> OTHER INFORMATION: Synthetic construct

<400> SEQUENCE: 80

Ser Asp Ser Arg Cys Pro Thr Gln Gly Glu Ala Tyr Leu Asp Lys Gln
1               5                   10                  15

Ser Asp Thr Gln Tyr Val Cys Lys Arg Thr Leu Val Asp Arg Gly
            20                  25                  30

<210> SEQ ID NO 81
<211> LENGTH: 31
<212> TYPE: PRT
<213> ORGANISM: Artificial Sequence
<220> FEATURE:
<223> OTHER INFORMATION: Synthetic construct

<400> SEQUENCE: 81

Val Val Ala Arg Cys Pro Ala Met Gly Pro Ala Thr Leu Pro Glu Glu
1               5                   10                  15

His Gln Ala Ser Thr Val Cys Arg Arg Asp Gln Ser Asp Arg Gly
            20                  25                  30
```

```
<210> SEQ ID NO 82
<211> LENGTH: 31
<212> TYPE: PRT
<213> ORGANISM: Artificial Sequence
<220> FEATURE:
<223> OTHER INFORMATION: Synthetic construct

<400> SEQUENCE: 82

Ile Ala Thr Ala Cys Pro Ser Asn Gly Glu Ala Lys Leu Asp Glu Glu
1               5                   10                  15

His Ile Lys Glu Tyr Ala Cys Lys Arg Leu Tyr Ser Asp Arg Gly
            20                  25                  30

<210> SEQ ID NO 83
<211> LENGTH: 31
<212> TYPE: PRT
<213> ORGANISM: Artificial Sequence
<220> FEATURE:
<223> OTHER INFORMATION: Synthetic construct

<400> SEQUENCE: 83

Ile Ser Ala Ala Cys Pro Ala Val Gln Leu Thr Glu Asn Ser Lys Ala
1               5                   10                  15

Thr Asp Ser Asn Tyr Leu Cys Arg Arg Gly Val Thr Asn Arg Gly
            20                  25                  30

<210> SEQ ID NO 84
<211> LENGTH: 31
<212> TYPE: PRT
<213> ORGANISM: Artificial Sequence
<220> FEATURE:
<223> OTHER INFORMATION: Synthetic construct

<400> SEQUENCE: 84

Val Gln Thr Ala Cys Pro Thr Asn Gly Glu Ala Lys Leu Glu Glu Glu
1               5                   10                  15

Ala Ser Ala Glu Tyr Glu Cys Lys Lys Thr Tyr Ser Asp Arg Gly
            20                  25                  30

<210> SEQ ID NO 85
<211> LENGTH: 31
<212> TYPE: PRT
<213> ORGANISM: Artificial Sequence
<220> FEATURE:
<223> OTHER INFORMATION: Synthetic construct

<400> SEQUENCE: 85

Thr Glu Ala Arg Cys Pro Thr Met Gly Glu Ala His Asn Ser Lys Ser
1               5                   10                  15

Leu Asp Ala Ser Tyr Val Cys Lys Ser Ser Tyr Val Asp Arg Gly
            20                  25                  30

<210> SEQ ID NO 86
<211> LENGTH: 31
<212> TYPE: PRT
<213> ORGANISM: Artificial Sequence
<220> FEATURE:
<223> OTHER INFORMATION: Synthetic construct

<400> SEQUENCE: 86

Val Glu Thr Arg Cys Pro Thr Met Gly Glu Ala His Asn Ser Lys Ser
1               5                   10                  15

Ser Asp Ala Ala Tyr Val Cys Lys Lys Gly Phe Ser Asp Arg Gly
            20                  25                  30
```

```
<210> SEQ ID NO 87
<211> LENGTH: 31
<212> TYPE: PRT
<213> ORGANISM: Artificial Sequence
<220> FEATURE:
<223> OTHER INFORMATION: Synthetic construct

<400> SEQUENCE: 87

Val Ala Ala Arg Cys Pro Ala Met Gly Pro Ala Thr Leu Pro Glu Glu
1               5                   10                  15

His Gln Ala Ser Thr Val Cys Arg Arg Asp Gln Ser Asp Arg Gly
            20                  25                  30

<210> SEQ ID NO 88
<211> LENGTH: 31
<212> TYPE: PRT
<213> ORGANISM: Artificial Sequence
<220> FEATURE:
<223> OTHER INFORMATION: Synthetic construct

<400> SEQUENCE: 88

Val Ala Ala Arg Cys Pro Thr Met Gly Pro Ala Thr Leu Pro Glu Glu
1               5                   10                  15

His Gln Ser Gly Thr Val Cys Lys Arg Asp Gln Ser Asp Arg Gly
            20                  25                  30

<210> SEQ ID NO 89
<211> LENGTH: 31
<212> TYPE: PRT
<213> ORGANISM: Artificial Sequence
<220> FEATURE:
<223> OTHER INFORMATION: Synthetic construct

<400> SEQUENCE: 89

Val Ala Ala Arg Cys Pro Thr Met Gly Pro Ala Thr Leu Pro Glu Glu
1               5                   10                  15

His Gln Ser Gly Thr Val Cys Lys Arg Asp Gln Ser Asp Arg Gly
            20                  25                  30

<210> SEQ ID NO 90
<211> LENGTH: 31
<212> TYPE: PRT
<213> ORGANISM: Artificial Sequence
<220> FEATURE:
<223> OTHER INFORMATION: Synthetic construct

<400> SEQUENCE: 90

Val Ala Ala Arg Cys Pro Thr Met Gly Pro Ala Val Leu Thr Glu Glu
1               5                   10                  15

Arg Gln Ile Gly Thr Val Cys Lys Arg Asp Gln Ser Asp Arg Gly
            20                  25                  30

<210> SEQ ID NO 91
<211> LENGTH: 31
<212> TYPE: PRT
<213> ORGANISM: Artificial Sequence
<220> FEATURE:
<223> OTHER INFORMATION: Synthetic construct

<400> SEQUENCE: 91

Val Ala Ala Arg Cys Pro Thr Met Gly Pro Ala Ala Leu Ala Glu Glu
1               5                   10                  15

Arg Gln Ile Gly Thr Val Cys Lys Arg Asp Gln Ser Asp Arg Gly
            20                  25                  30
```

```
<210> SEQ ID NO 92
<211> LENGTH: 31
<212> TYPE: PRT
<213> ORGANISM: Artificial Sequence
<220> FEATURE:
<223> OTHER INFORMATION: Synthetic construct

<400> SEQUENCE: 92

Val Ala Ala Arg Cys Pro Thr Met Gly Pro Ala Val Leu Thr Glu Glu
1               5                   10                  15

Arg Gln Ile Gly Thr Val Cys Lys Arg Asp Gln Ser Asp Arg Gly
            20                  25                  30

<210> SEQ ID NO 93
<211> LENGTH: 31
<212> TYPE: PRT
<213> ORGANISM: Artificial Sequence
<220> FEATURE:
<223> OTHER INFORMATION: Synthetic construct

<400> SEQUENCE: 93

Val Ala Ala Arg Cys Pro Thr Met Gly Pro Ala Val Leu Thr Glu Glu
1               5                   10                  15

His Gln Ile Gly Thr Val Cys Lys Arg Asp Gln Ser Asp Arg Gly
            20                  25                  30

<210> SEQ ID NO 94
<211> LENGTH: 31
<212> TYPE: PRT
<213> ORGANISM: Artificial Sequence
<220> FEATURE:
<223> OTHER INFORMATION: Synthetic construct

<400> SEQUENCE: 94

Val Ala Ala Arg Cys Pro Thr Met Gly Pro Ala Val Leu Thr Glu Glu
1               5                   10                  15

Arg Gln Ile Gly Thr Val Cys Lys Arg Asp Gln Ser Asp Arg Gly
            20                  25                  30

<210> SEQ ID NO 95
<211> LENGTH: 31
<212> TYPE: PRT
<213> ORGANISM: Artificial Sequence
<220> FEATURE:
<223> OTHER INFORMATION: Synthetic construct

<400> SEQUENCE: 95

Val Ala Ala Arg Cys Pro Thr Met Gly Pro Ala Ala Leu Ala Glu Glu
1               5                   10                  15

Arg Gln Ile Gly Thr Val Cys Lys Arg Asp Gln Ser Asp Arg Gly
            20                  25                  30

<210> SEQ ID NO 96
<211> LENGTH: 31
<212> TYPE: PRT
<213> ORGANISM: Artificial Sequence
<220> FEATURE:
<223> OTHER INFORMATION: Synthetic construct

<400> SEQUENCE: 96

Thr Val Ser Asn Cys Pro Thr Thr Gly Glu Ser His Asn Thr Lys Arg
1               5                   10                  15

Ala Asp His Asn Tyr Leu Cys Lys Arg Gly Val Thr Asp Arg Gly
```

20          25          30

<210> SEQ ID NO 97
<211> LENGTH: 31
<212> TYPE: PRT
<213> ORGANISM: Artificial Sequence
<220> FEATURE:
<223> OTHER INFORMATION: Synthetic construct

<400> SEQUENCE: 97

Val Ala Ala Arg Cys Pro Ala Met Gly Pro Ala Thr Leu Asp Glu Glu
1               5                   10                  15

His Gln Ser Gly Thr Val Cys Lys Arg Asp Gln Ser Asp Arg Gly
            20                  25                  30

<210> SEQ ID NO 98
<211> LENGTH: 31
<212> TYPE: PRT
<213> ORGANISM: Artificial Sequence
<220> FEATURE:
<223> OTHER INFORMATION: Synthetic construct

<400> SEQUENCE: 98

Ser Glu Ala Arg Cys Pro Thr Met Gly Glu Ala His Asn Pro Lys Ala
1               5                   10                  15

Leu Asp Ser Asn Tyr Leu Cys Lys Ser Thr Tyr Val Asp Arg Gly
            20                  25                  30

<210> SEQ ID NO 99
<211> LENGTH: 31
<212> TYPE: PRT
<213> ORGANISM: Artificial Sequence
<220> FEATURE:
<223> OTHER INFORMATION: Synthetic construct

<400> SEQUENCE: 99

Val Ala Ala Arg Cys Pro Thr Met Gly Pro Ala Thr Leu Ala Glu Glu
1               5                   10                  15

His Gln Gly Gly Thr Val Cys Lys Arg Asp Gln Ser Asp Arg Gly
            20                  25                  30

<210> SEQ ID NO 100
<211> LENGTH: 31
<212> TYPE: PRT
<213> ORGANISM: Artificial Sequence
<220> FEATURE:
<223> OTHER INFORMATION: Synthetic construct

<400> SEQUENCE: 100

Val Ala Ala Arg Cys Pro Thr Met Gly Pro Ala Thr Leu Ala Glu Glu
1               5                   10                  15

His Gln Ser Gly Thr Val Cys Lys Arg Asp Gln Ser Asp Arg Gly
            20                  25                  30

<210> SEQ ID NO 101
<211> LENGTH: 31
<212> TYPE: PRT
<213> ORGANISM: Artificial Sequence
<220> FEATURE:
<223> OTHER INFORMATION: Synthetic construct

<400> SEQUENCE: 101

Val Ala Ala Arg Cys Pro Thr Met Gly Pro Ala Thr Leu Ala Glu Glu
1               5                   10                  15

His Gln Gly Gly Thr Val Cys Lys Arg Asp Gln Ser Asp Arg Gly
            20                  25                  30

<210> SEQ ID NO 102
<211> LENGTH: 31
<212> TYPE: PRT
<213> ORGANISM: Artificial Sequence
<220> FEATURE:
<223> OTHER INFORMATION: Synthetic construct

<400> SEQUENCE: 102

Val Glu Ala Arg Cys Pro Thr Thr Gly Pro Ala Thr Leu Pro Glu Glu
1               5                   10                  15

His Gln Ala Asn Met Val Cys Lys Arg Asp Gln Ser Asp Arg Gly
            20                  25                  30

<210> SEQ ID NO 103
<211> LENGTH: 31
<212> TYPE: PRT
<213> ORGANISM: Artificial Sequence
<220> FEATURE:
<223> OTHER INFORMATION: Synthetic construct

<400> SEQUENCE: 103

Thr Val Ser Asn Cys Pro Thr Thr Gly Glu Ala His Asn Pro Lys Arg
1               5                   10                  15

Ala Glu Asp Thr Tyr Val Cys Lys Ser Gly Val Thr Ser Arg Gly
            20                  25                  30

<210> SEQ ID NO 104
<211> LENGTH: 31
<212> TYPE: PRT
<213> ORGANISM: Artificial Sequence
<220> FEATURE:
<223> OTHER INFORMATION: Synthetic construct

<400> SEQUENCE: 104

Ala Thr Gly Ala Cys Pro Thr Met Gly Asp Ala His Met Ser Glu Glu
1               5                   10                  15

Gly Asn Glu Glu Trp Glu Cys Lys Arg Ser Tyr Ser Asp Arg Gly
            20                  25                  30

<210> SEQ ID NO 105
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: any amino acid (e.g., R, H, or K, such as R or
      K)
<220> FEATURE:
<221> NAME/KEY: MISC_FEATURE
<222> LOCATION: (3)..(3)
<223> OTHER INFORMATION: any amino acid (e.g., R, H, Q, K, T, N, or S,
      such as R, H, Q, K, or S)
<220> FEATURE:
<221> NAME/KEY: MISC_FEATURE
<222> LOCATION: (4)..(4)
<223> OTHER INFORMATION: any amino acid (e.g., T, S, G, D, E, I, V, or
      L, such as T, S, G, D, or L)
<220> FEATURE:
<221> NAME/KEY: MISC_FEATURE
<222> LOCATION: (5)..(5)
<223> OTHER INFORMATION: any amino acid (e.g., F, M, Y, W, V, A, I, L,
      N, or Q, such as F, M, Y, V, Y, L, or Q)
<220> FEATURE:

```
<221> NAME/KEY: MISC_FEATURE
<222> LOCATION: (6)..(6)
<223> OTHER INFORMATION: any amino acid (e.g., V, I, L, M, A, T, or S,
      such as V, T, or S)
<220> FEATURE:
<221> NAME/KEY: MISC_FEATURE
<222> LOCATION: (7)..(7)
<223> OTHER INFORMATION: any amino acid (e.g., D, E, N, or Q, such as D
      or N)

<400> SEQUENCE: 105

Cys Xaa Xaa Xaa Xaa Xaa Xaa Arg Gly
1               5

<210> SEQ ID NO 106
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: any amino acid (e.g., T, I, S, L, V, or A, such
      as T, I, S, V, or A)
<220> FEATURE:
<221> NAME/KEY: MISC_FEATURE
<222> LOCATION: (2)..(2)
<223> OTHER INFORMATION: any amino acid (e.g., D, E, R, H, K, A, V, I,
      L, M, N, S, Q, or T, such as D, E, R, K, A, V, N, S, Q, or T)
<220> FEATURE:
<221> NAME/KEY: MISC_FEATURE
<222> LOCATION: (3)..(3)
<223> OTHER INFORMATION: any amino acid (e.g., S, T, A, V, I, L, D, E,
      or G, such as S, T, A, D, or G)
<220> FEATURE:
<221> NAME/KEY: MISC_FEATURE
<222> LOCATION: (4)..(4)
<223> OTHER INFORMATION: any amino acid (e.g., R, A, G, V, I, L, K, H,
      Q, or N, such as R, A, K, or N)

<400> SEQUENCE: 106

Xaa Xaa Xaa Xaa Cys Pro
1               5

<210> SEQ ID NO 107
<211> LENGTH: 28
<212> TYPE: PRT
<213> ORGANISM: Artificial Sequence
<220> FEATURE:
<223> OTHER INFORMATION: Synthetic construct

<400> SEQUENCE: 107

Val Thr Phe Lys Thr Ala His Ala Lys Lys Gln Glu Val Val Val Leu
1               5                   10                  15

Gly Ser Gln Glu Gly Ala Met His Thr Ala Leu Thr
            20                  25

<210> SEQ ID NO 108
<211> LENGTH: 28
<212> TYPE: PRT
<213> ORGANISM: Artificial Sequence
<220> FEATURE:
<223> OTHER INFORMATION: Synthetic construct

<400> SEQUENCE: 108

Val Thr Phe Lys Thr Ala His Ala Lys Lys Gln Glu Val Val Val Leu
1               5                   10                  15

Gly Ser Gln Glu Gly Ala Met His Thr Ala Leu Thr
            20                  25
```

<210> SEQ ID NO 109
<211> LENGTH: 28
<212> TYPE: PRT
<213> ORGANISM: Artificial Sequence
<220> FEATURE:
<223> OTHER INFORMATION: Synthetic construct

<400> SEQUENCE: 109

Val Thr Phe Lys Thr Ala His Ala Lys Lys Gln Glu Val Val Val Leu
1               5                   10                  15

Gly Ser Gln Glu Gly Ala Met His Thr Ala Leu Thr
            20                  25

<210> SEQ ID NO 110
<211> LENGTH: 28
<212> TYPE: PRT
<213> ORGANISM: Artificial Sequence
<220> FEATURE:
<223> OTHER INFORMATION: Synthetic construct

<400> SEQUENCE: 110

Val Thr Phe Lys Thr Ala His Ala Lys Lys Gln Glu Val Val Val Leu
1               5                   10                  15

Gly Ser Gln Glu Gly Ala Met His Thr Ala Leu Thr
            20                  25

<210> SEQ ID NO 111
<211> LENGTH: 28
<212> TYPE: PRT
<213> ORGANISM: Artificial Sequence
<220> FEATURE:
<223> OTHER INFORMATION: Synthetic construct

<400> SEQUENCE: 111

Val Thr Phe Lys Thr Ala His Ala Lys Lys Gln Glu Val Val Val Leu
1               5                   10                  15

Gly Ser Gln Glu Gly Ala Met His Thr Ala Leu Thr
            20                  25

<210> SEQ ID NO 112
<211> LENGTH: 28
<212> TYPE: PRT
<213> ORGANISM: Artificial Sequence
<220> FEATURE:
<223> OTHER INFORMATION: Synthetic construct

<400> SEQUENCE: 112

Val Thr Phe Lys Asn Pro His Ala Lys Lys Gln Asp Val Val Val Leu
1               5                   10                  15

Gly Ser Gln Glu Gly Ala Met His Thr Ala Leu Thr
            20                  25

<210> SEQ ID NO 113
<211> LENGTH: 28
<212> TYPE: PRT
<213> ORGANISM: Artificial Sequence
<220> FEATURE:
<223> OTHER INFORMATION: Synthetic construct

<400> SEQUENCE: 113

Val Thr Phe Lys Asn Pro His Ala Lys Lys Gln Asp Val Val Val Leu
1               5                   10                  15

Gly Ser Gln Glu Gly Ala Met Gln Thr Ala Leu Thr 20                  25

<210> SEQ ID NO 114
<211> LENGTH: 28
<212> TYPE: PRT
<213> ORGANISM: Artificial Sequence
<220> FEATURE:
<223> OTHER INFORMATION: Synthetic construct

<400> SEQUENCE: 114

Val Thr Phe Lys Asn Pro His Ala Lys Lys Gln Asp Val Val Val Leu
1               5                   10                  15

Gly Ser Gln Glu Gly Ala Met His Thr Ala Leu Thr
            20                  25

<210> SEQ ID NO 115
<211> LENGTH: 28
<212> TYPE: PRT
<213> ORGANISM: Artificial Sequence
<220> FEATURE:
<223> OTHER INFORMATION: Synthetic construct

<400> SEQUENCE: 115

Val Thr Phe Lys Asn Pro His Ala Lys Lys Gln Asp Val Val Val Leu
1               5                   10                  15

Gly Ser Gln Glu Gly Ala Met His Thr Ala Leu Thr
            20                  25

<210> SEQ ID NO 116
<211> LENGTH: 28
<212> TYPE: PRT
<213> ORGANISM: Artificial Sequence
<220> FEATURE:
<223> OTHER INFORMATION: Synthetic construct

<400> SEQUENCE: 116

Val Thr Phe Lys Asn Pro His Ala Lys Lys Gln Asp Val Val Val Leu
1               5                   10                  15

Gly Ser Gln Glu Gly Ala Met His Thr Ala Leu Thr
            20                  25

<210> SEQ ID NO 117
<211> LENGTH: 28
<212> TYPE: PRT
<213> ORGANISM: Artificial Sequence
<220> FEATURE:
<223> OTHER INFORMATION: Synthetic construct

<400> SEQUENCE: 117

Val Thr Phe Lys Asn Pro His Ala Lys Lys Gln Asp Val Val Val Leu
1               5                   10                  15

Gly Ser Gln Glu Gly Ala Met His Thr Ala Leu Thr
            20                  25

<210> SEQ ID NO 118
<211> LENGTH: 28
<212> TYPE: PRT
<213> ORGANISM: Artificial Sequence
<220> FEATURE:
<223> OTHER INFORMATION: Synthetic construct

<400> SEQUENCE: 118

Val Thr Phe Lys Asn Pro His Ala Lys Lys Gln Asp Val Val Val Leu
1               5                   10                  15

Gly Ser Gln Glu Gly Ala Met His Thr Ala Leu Thr
            20                  25

<210> SEQ ID NO 119
<211> LENGTH: 28
<212> TYPE: PRT
<213> ORGANISM: Artificial Sequence
<220> FEATURE:
<223> OTHER INFORMATION: Synthetic construct

<400> SEQUENCE: 119

Val Thr Phe Lys Asn Pro His Ala Lys Lys Gln Asp Val Val Val Leu
1               5                   10                  15

Gly Ser Gln Glu Gly Ala Met His Thr Ala Leu Thr
            20                  25

<210> SEQ ID NO 120
<211> LENGTH: 28
<212> TYPE: PRT
<213> ORGANISM: Artificial Sequence
<220> FEATURE:
<223> OTHER INFORMATION: Synthetic construct

<400> SEQUENCE: 120

Val Thr Phe Lys Asn Pro His Ala Lys Lys Gln Asp Val Val Val Leu
1               5                   10                  15

Gly Ser Gln Glu Gly Ala Met His Thr Ala Leu Thr
            20                  25

<210> SEQ ID NO 121
<211> LENGTH: 28
<212> TYPE: PRT
<213> ORGANISM: Artificial Sequence
<220> FEATURE:
<223> OTHER INFORMATION: Synthetic construct

<400> SEQUENCE: 121

Val Thr Phe Lys Asn Pro His Ala Lys Lys Gln Asp Val Val Val Leu
1               5                   10                  15

Gly Ser Gln Glu Gly Ala Met His Thr Ala Leu Thr
            20                  25

<210> SEQ ID NO 122
<211> LENGTH: 28
<212> TYPE: PRT
<213> ORGANISM: Artificial Sequence
<220> FEATURE:
<223> OTHER INFORMATION: Synthetic construct

<400> SEQUENCE: 122

Val Thr Phe Lys Asn Pro His Ala Lys Lys Gln Asp Val Val Val Leu
1               5                   10                  15

Gly Ser Gln Glu Gly Ala Met His Thr Ala Leu Thr
            20                  25

<210> SEQ ID NO 123
<211> LENGTH: 28
<212> TYPE: PRT
<213> ORGANISM: Artificial Sequence
<220> FEATURE:
<223> OTHER INFORMATION: Synthetic construct

<400> SEQUENCE: 123

Val Thr Phe Lys Asn Pro His Ala Lys Lys Gln Asp Val Val Val Leu
1               5                   10                  15

Gly Ser Gln Glu Gly Ala Met His Thr Ala Leu Thr
            20                  25

<210> SEQ ID NO 124
<211> LENGTH: 28
<212> TYPE: PRT
<213> ORGANISM: Artificial Sequence
<220> FEATURE:
<223> OTHER INFORMATION: Synthetic construct

<400> SEQUENCE: 124

Val Thr Phe Lys Asn Pro His Ala Lys Lys Gln Asp Val Val Val Leu
1               5                   10                  15

Gly Ser Gln Glu Gly Ala Met His Thr Ala Leu Thr
            20                  25

<210> SEQ ID NO 125
<211> LENGTH: 28
<212> TYPE: PRT
<213> ORGANISM: Artificial Sequence
<220> FEATURE:
<223> OTHER INFORMATION: Synthetic construct

<400> SEQUENCE: 125

Val Thr Phe Lys Asn Ala His Ala Lys Lys Gln Glu Val Val Val Leu
1               5                   10                  15

Gly Ser Gln Glu Gly Ala Met His Thr Ala Leu Thr
            20                  25

<210> SEQ ID NO 126
<211> LENGTH: 28
<212> TYPE: PRT
<213> ORGANISM: Artificial Sequence
<220> FEATURE:
<223> OTHER INFORMATION: Synthetic construct

<400> SEQUENCE: 126

Val Thr Phe Lys Asn Ala His Ala Lys Lys Gln Glu Val Val Val Leu
1               5                   10                  15

Gly Ser Gln Glu Gly Ala Met His Thr Ala Leu Thr
            20                  25

<210> SEQ ID NO 127
<211> LENGTH: 28
<212> TYPE: PRT
<213> ORGANISM: Artificial Sequence
<220> FEATURE:
<223> OTHER INFORMATION: Synthetic construct

<400> SEQUENCE: 127

Val Thr Phe Lys Asn Ala His Ala Lys Lys Gln Glu Val Val Val Leu
1               5                   10                  15

Gly Ser Gln Glu Gly Ala Met His Thr Ala Leu Thr
            20                  25

<210> SEQ ID NO 128
<211> LENGTH: 28
<212> TYPE: PRT
<213> ORGANISM: Artificial Sequence
<220> FEATURE:
<223> OTHER INFORMATION: Synthetic construct

<400> SEQUENCE: 128

Val Thr Phe Lys Asn Ala His Ala Lys Lys Gln Glu Val Val Val Leu

-continued

```
                1               5                  10                  15
Gly Ser Gln Glu Gly Ala Met His Thr Ala Leu Thr
            20                  25

<210> SEQ ID NO 129
<211> LENGTH: 28
<212> TYPE: PRT
<213> ORGANISM: Artificial Sequence
<220> FEATURE:
<223> OTHER INFORMATION: Synthetic construct

<400> SEQUENCE: 129

Val Thr Phe Lys Asn Ala His Ala Lys Lys Gln Glu Val Val Val Leu
1               5                  10                  15

Gly Ser Gln Glu Gly Ala Met His Thr Ala Leu Thr
            20                  25

<210> SEQ ID NO 130
<211> LENGTH: 28
<212> TYPE: PRT
<213> ORGANISM: Artificial Sequence
<220> FEATURE:
<223> OTHER INFORMATION: Synthetic construct

<400> SEQUENCE: 130

Val Thr Phe Lys Val Pro His Ala Lys Arg Gln Asp Val Thr Val Leu
1               5                  10                  15

Gly Ser Gln Glu Gly Ala Met His Ser Ala Leu Ala
            20                  25

<210> SEQ ID NO 131
<211> LENGTH: 28
<212> TYPE: PRT
<213> ORGANISM: Artificial Sequence
<220> FEATURE:
<223> OTHER INFORMATION: Synthetic construct

<400> SEQUENCE: 131

Val Thr Phe Lys Val Pro His Ala Lys Arg Gln Asp Val Thr Val Leu
1               5                  10                  15

Gly Ser Gln Glu Gly Ala Met His Ser Ala Leu Thr
            20                  25

<210> SEQ ID NO 132
<211> LENGTH: 28
<212> TYPE: PRT
<213> ORGANISM: Artificial Sequence
<220> FEATURE:
<223> OTHER INFORMATION: Synthetic construct

<400> SEQUENCE: 132

Val Thr Phe Lys Val Pro His Ala Lys Arg Gln Asp Val Thr Val Leu
1               5                  10                  15

Gly Ser Gln Glu Gly Ala Met His Ser Ala Leu Ala
            20                  25

<210> SEQ ID NO 133
<211> LENGTH: 28
<212> TYPE: PRT
<213> ORGANISM: Artificial Sequence
<220> FEATURE:
<223> OTHER INFORMATION: Synthetic construct

<400> SEQUENCE: 133
```

```
Val Thr Phe Lys Val Pro His Ala Lys Arg Gln Asp Val Thr Val Leu
1               5                   10                  15

Gly Ser Gln Glu Gly Ala Met His Ser Ala Leu Ala
            20                  25
```

<210> SEQ ID NO 134
<211> LENGTH: 28
<212> TYPE: PRT
<213> ORGANISM: Artificial Sequence
<220> FEATURE:
<223> OTHER INFORMATION: Synthetic construct

<400> SEQUENCE: 134

```
Val Thr Phe Lys Val Pro His Ala Lys Arg Gln Asp Val Thr Val Leu
1               5                   10                  15

Gly Ser Gln Glu Gly Ala Met His Ser Ala Leu Thr
            20                  25
```

<210> SEQ ID NO 135
<211> LENGTH: 28
<212> TYPE: PRT
<213> ORGANISM: Artificial Sequence
<220> FEATURE:
<223> OTHER INFORMATION: Synthetic construct

<400> SEQUENCE: 135

```
Met Glu Phe Glu Glu Pro His Ala Thr Lys Gln Ser Val Ala Leu
1               5                   10                  15

Gly Ser Gln Glu Gly Ala Leu His Gln Ala Leu Ala
            20                  25
```

<210> SEQ ID NO 136
<211> LENGTH: 28
<212> TYPE: PRT
<213> ORGANISM: Artificial Sequence
<220> FEATURE:
<223> OTHER INFORMATION: Synthetic construct

<400> SEQUENCE: 136

```
Met Glu Phe Glu Glu Pro His Ala Thr Lys Gln Ser Val Ile Ala Leu
1               5                   10                  15

Gly Ser Gln Glu Gly Ala Leu His Gln Ala Leu Ala
            20                  25
```

<210> SEQ ID NO 137
<211> LENGTH: 28
<212> TYPE: PRT
<213> ORGANISM: Artificial Sequence
<220> FEATURE:
<223> OTHER INFORMATION: Synthetic construct

<400> SEQUENCE: 137

```
Met Glu Phe Glu Glu Pro His Ala Thr Lys Gln Ser Val Ile Ala Leu
1               5                   10                  15

Gly Ser Gln Glu Gly Ala Leu His Gln Ala Leu Ala
            20                  25
```

<210> SEQ ID NO 138
<211> LENGTH: 28
<212> TYPE: PRT
<213> ORGANISM: Artificial Sequence
<220> FEATURE:
<223> OTHER INFORMATION: Synthetic construct

<400> SEQUENCE: 138

Met Glu Phe Glu Glu Ala His Ala Thr Lys Gln Ser Val Val Ala Leu
1               5                   10                  15

Gly Ser Gln Glu Gly Gly Leu His Gln Ala Leu Ala
            20                  25

<210> SEQ ID NO 139
<211> LENGTH: 28
<212> TYPE: PRT
<213> ORGANISM: Artificial Sequence
<220> FEATURE:
<223> OTHER INFORMATION: Synthetic construct

<400> SEQUENCE: 139

Met Glu Phe Glu Glu Ala His Ala Thr Lys Gln Ser Val Val Ala Leu
1               5                   10                  15

Gly Ser Gln Glu Gly Gly Leu His Gln Ala Leu Ala
            20                  25

<210> SEQ ID NO 140
<211> LENGTH: 28
<212> TYPE: PRT
<213> ORGANISM: Artificial Sequence
<220> FEATURE:
<223> OTHER INFORMATION: Synthetic construct

<400> SEQUENCE: 140

Val Glu Phe Glu Glu Pro His Ala Thr Lys Gln Thr Val Val Ala Leu
1               5                   10                  15

Gly Ser Gln Glu Gly Ala Leu His Thr Ala Leu Ala
            20                  25

<210> SEQ ID NO 141
<211> LENGTH: 28
<212> TYPE: PRT
<213> ORGANISM: Artificial Sequence
<220> FEATURE:
<223> OTHER INFORMATION: Synthetic construct

<400> SEQUENCE: 141

Val Glu Phe Glu Pro Pro His Ala Ala Thr Ile Arg Val Leu Ala Leu
1               5                   10                  15

Gly Asp Gln Glu Gly Ser Leu Lys Thr Ala Leu Thr
            20                  25

<210> SEQ ID NO 142
<211> LENGTH: 28
<212> TYPE: PRT
<213> ORGANISM: Artificial Sequence
<220> FEATURE:
<223> OTHER INFORMATION: Synthetic construct

<400> SEQUENCE: 142

Val Glu Phe Glu Pro Pro His Ala Ala Thr Ile Arg Val Leu Ala Leu
1               5                   10                  15

Gly Asn Gln Glu Gly Ser Leu Lys Thr Ala Leu Thr
            20                  25

<210> SEQ ID NO 143
<211> LENGTH: 28
<212> TYPE: PRT
<213> ORGANISM: Artificial Sequence
<220> FEATURE:
<223> OTHER INFORMATION: Synthetic construct

```
<400> SEQUENCE: 143

Val Glu Phe Glu Pro Pro His Ala Ala Thr Ile Arg Val Leu Ala Leu
1               5                   10                  15

Gly Asn Gln Glu Gly Ser Leu Lys Thr Ala Leu Thr
            20                  25

<210> SEQ ID NO 144
<211> LENGTH: 28
<212> TYPE: PRT
<213> ORGANISM: Artificial Sequence
<220> FEATURE:
<223> OTHER INFORMATION: Synthetic construct

<400> SEQUENCE: 144

Val Glu Phe Glu Pro Pro His Ala Ala Thr Ile Arg Val Leu Ala Leu
1               5                   10                  15

Gly Asn Gln Glu Gly Ser Leu Lys Thr Ala Leu Thr
            20                  25

<210> SEQ ID NO 145
<211> LENGTH: 28
<212> TYPE: PRT
<213> ORGANISM: Artificial Sequence
<220> FEATURE:
<223> OTHER INFORMATION: Synthetic construct

<400> SEQUENCE: 145

Val Glu Phe Glu Pro Pro His Ala Ala Thr Ile Arg Val Leu Ala Leu
1               5                   10                  15

Gly Asn Gln Glu Gly Ser Leu Lys Thr Ala Leu Thr
            20                  25

<210> SEQ ID NO 146
<211> LENGTH: 28
<212> TYPE: PRT
<213> ORGANISM: Artificial Sequence
<220> FEATURE:
<223> OTHER INFORMATION: Synthetic construct

<400> SEQUENCE: 146

Val Glu Phe Glu Pro Pro His Ala Ala Thr Ile Lys Val Leu Ala Leu
1               5                   10                  15

Gly Asn Gln Glu Gly Ser Leu Lys Thr Ala Leu Thr
            20                  25

<210> SEQ ID NO 147
<211> LENGTH: 28
<212> TYPE: PRT
<213> ORGANISM: Artificial Sequence
<220> FEATURE:
<223> OTHER INFORMATION: Synthetic construct

<400> SEQUENCE: 147

Val Glu Phe Glu Pro Pro His Ala Ala Thr Ile Arg Val Leu Ala Leu
1               5                   10                  15

Gly Asn Gln Glu Gly Ser Leu Lys Thr Ala Leu Thr
            20                  25

<210> SEQ ID NO 148
<211> LENGTH: 28
<212> TYPE: PRT
<213> ORGANISM: Artificial Sequence
<220> FEATURE:
<223> OTHER INFORMATION: Synthetic construct
```

<400> SEQUENCE: 148

Val Glu Phe Glu Pro Pro His Ala Ala Thr Ile Arg Val Leu Ala Leu
1               5                   10                  15

Gly Asn Gln Glu Gly Ser Leu Lys Thr Ala Leu Thr
            20                  25

<210> SEQ ID NO 149
<211> LENGTH: 28
<212> TYPE: PRT
<213> ORGANISM: Artificial Sequence
<220> FEATURE:
<223> OTHER INFORMATION: Synthetic construct

<400> SEQUENCE: 149

Val Glu Phe Glu Pro Pro His Ala Ala Thr Ile Arg Val Leu Ala Leu
1               5                   10                  15

Gly Asp Gln Glu Gly Ser Leu Lys Thr Ala Leu Thr
            20                  25

<210> SEQ ID NO 150
<211> LENGTH: 28
<212> TYPE: PRT
<213> ORGANISM: Artificial Sequence
<220> FEATURE:
<223> OTHER INFORMATION: Synthetic construct

<400> SEQUENCE: 150

Val Glu Phe Glu Pro Pro His Ala Ala Thr Ile Arg Val Leu Ala Leu
1               5                   10                  15

Gly Asn Gln Glu Gly Ser Leu Lys Thr Ala Leu Thr
            20                  25

<210> SEQ ID NO 151
<211> LENGTH: 28
<212> TYPE: PRT
<213> ORGANISM: Artificial Sequence
<220> FEATURE:
<223> OTHER INFORMATION: Synthetic construct

<400> SEQUENCE: 151

Val Glu Phe Lys Asp Ala His Ala Lys Arg Gln Thr Val Val Val Leu
1               5                   10                  15

Gly Ser Gln Glu Gly Ala Val His Thr Ala Leu Ala
            20                  25

<210> SEQ ID NO 152
<211> LENGTH: 28
<212> TYPE: PRT
<213> ORGANISM: Artificial Sequence
<220> FEATURE:
<223> OTHER INFORMATION: Synthetic construct

<400> SEQUENCE: 152

Val Glu Phe Lys Asp Ala His Ala Lys Arg Gln Thr Val Val Val Leu
1               5                   10                  15

Gly Ser Gln Glu Gly Ala Val His Thr Ala Leu Ala
            20                  25

<210> SEQ ID NO 153
<211> LENGTH: 28
<212> TYPE: PRT
<213> ORGANISM: Artificial Sequence
<220> FEATURE:

-continued

<223> OTHER INFORMATION: Synthetic construct

<400> SEQUENCE: 153

Val Glu Phe Gly Glu Pro His Ala Val Lys Met Asp Ile Phe Asn Leu
1               5                   10                  15

Gly Asp Gln Thr Gly Ile Leu Leu Lys Ser Leu Ala
            20                  25

<210> SEQ ID NO 154
<211> LENGTH: 28
<212> TYPE: PRT
<213> ORGANISM: Artificial Sequence
<220> FEATURE:
<223> OTHER INFORMATION: Synthetic construct

<400> SEQUENCE: 154

Val Glu Phe Gly Glu Pro His Ala Thr Thr Val Lys Val Leu Ala Leu
1               5                   10                  15

Gly Pro Gln Glu Gly Ala Leu Arg Asn Ala Leu Ala
            20                  25

<210> SEQ ID NO 155
<211> LENGTH: 28
<212> TYPE: PRT
<213> ORGANISM: Artificial Sequence
<220> FEATURE:
<223> OTHER INFORMATION: Synthetic construct

<400> SEQUENCE: 155

Val Glu Phe Gln Glu Pro His Ala Thr Lys Gln Glu Val Leu Ala Leu
1               5                   10                  15

Gly Ser Gln Glu Gly Ala Leu His Ser Ala Leu Ala
            20                  25

<210> SEQ ID NO 156
<211> LENGTH: 28
<212> TYPE: PRT
<213> ORGANISM: Artificial Sequence
<220> FEATURE:
<223> OTHER INFORMATION: Synthetic construct

<400> SEQUENCE: 156

Val Glu Phe Thr Glu Pro His Ala Thr Thr Met Thr Val Met Val Leu
1               5                   10                  15

Gly Ala Gln Glu Gly Ala Leu Arg Thr Ala Leu Ala
            20                  25

<210> SEQ ID NO 157
<211> LENGTH: 28
<212> TYPE: PRT
<213> ORGANISM: Artificial Sequence
<220> FEATURE:
<223> OTHER INFORMATION: Synthetic construct

<400> SEQUENCE: 157

Ile Glu Phe Glu Glu Pro His Ala Thr Arg Gln Thr Val Val Ala Leu
1               5                   10                  15

Gly Asn Gln Glu Gly Ala Leu His Thr Ala Leu Ala
            20                  25

<210> SEQ ID NO 158
<211> LENGTH: 28
<212> TYPE: PRT
<213> ORGANISM: Artificial Sequence
<220> FEATURE:
<223> OTHER INFORMATION: Synthetic construct

<400> SEQUENCE: 158

Val Glu Phe Gly Lys Thr His Ala Thr Lys Arg Glu Val Leu Ala Leu
1               5                   10                  15

Gly Ser Gln Glu Gly Thr Leu Gln Val Ala Leu Ala
            20                  25

<210> SEQ ID NO 159
<211> LENGTH: 28
<212> TYPE: PRT
<213> ORGANISM: Artificial Sequence
<220> FEATURE:
<223> OTHER INFORMATION: Synthetic construct

<400> SEQUENCE: 159

Val Glu Phe Gly Glu Pro His Ala Val Lys Met Asp Ile Phe Asn Leu
1               5                   10                  15

Gly Asp Gln Thr Gly Ile Leu Leu Lys Ser Leu Ala
            20                  25

<210> SEQ ID NO 160
<211> LENGTH: 28
<212> TYPE: PRT
<213> ORGANISM: Artificial Sequence
<220> FEATURE:
<223> OTHER INFORMATION: Synthetic construct

<400> SEQUENCE: 160

Val Glu Phe Gly Thr Pro His Ala Val Lys Met Asp Val Phe Asn Leu
1               5                   10                  15

Gly Asp Gln Thr Gly Val Leu Leu Lys Ser Leu Ala
            20                  25

<210> SEQ ID NO 161
<211> LENGTH: 28
<212> TYPE: PRT
<213> ORGANISM: Artificial Sequence
<220> FEATURE:
<223> OTHER INFORMATION: Synthetic construct

<400> SEQUENCE: 161

Val Glu Phe Gly Thr Pro His Ala Val Lys Met Asp Val Phe Asn Leu
1               5                   10                  15

Gly Asp Gln Thr Gly Val Leu Leu Lys Ser Leu Ala
            20                  25

<210> SEQ ID NO 162
<211> LENGTH: 28
<212> TYPE: PRT
<213> ORGANISM: Artificial Sequence
<220> FEATURE:
<223> OTHER INFORMATION: Synthetic construct

<400> SEQUENCE: 162

Val Glu Phe Gly Ala Pro His Ala Val Lys Met Asp Val Tyr Asn Leu
1               5                   10                  15

Gly Asp Gln Thr Gly Val Leu Leu Arg Ala Leu Ala
            20                  25

<210> SEQ ID NO 163
<211> LENGTH: 28
<212> TYPE: PRT

<213> ORGANISM: Artificial Sequence
<220> FEATURE:
<223> OTHER INFORMATION: Synthetic construct

<400> SEQUENCE: 163

Val Glu Phe Gly Ala Pro His Ala Val Lys Met Asp Val Tyr Asn Leu
1               5                   10                  15

Gly Asp Gln Thr Gly Val Leu Leu Lys Ala Leu Ala
            20                  25

<210> SEQ ID NO 164
<211> LENGTH: 28
<212> TYPE: PRT
<213> ORGANISM: Artificial Sequence
<220> FEATURE:
<223> OTHER INFORMATION: Synthetic construct

<400> SEQUENCE: 164

Val Glu Phe Gly Ala Pro His Ala Val Lys Met Asp Val Tyr Asn Leu
1               5                   10                  15

Gly Asp Gln Thr Gly Val Leu Leu Lys Ala Leu Ala
            20                  25

<210> SEQ ID NO 165
<211> LENGTH: 28
<212> TYPE: PRT
<213> ORGANISM: Artificial Sequence
<220> FEATURE:
<223> OTHER INFORMATION: Synthetic construct

<400> SEQUENCE: 165

Val Glu Phe Gly Val Pro His Ala Val Lys Met Asp Val Tyr Asn Leu
1               5                   10                  15

Gly Asp Gln Thr Gly Val Leu Leu Lys Ala Leu Ala
            20                  25

<210> SEQ ID NO 166
<211> LENGTH: 28
<212> TYPE: PRT
<213> ORGANISM: Artificial Sequence
<220> FEATURE:
<223> OTHER INFORMATION: Synthetic construct

<400> SEQUENCE: 166

Val Glu Phe Gly Ala Pro His Ala Val Lys Met Asp Val Tyr Asn Leu
1               5                   10                  15

Gly Asp Gln Thr Gly Val Leu Leu Lys Ala Leu Ala
            20                  25

<210> SEQ ID NO 167
<211> LENGTH: 28
<212> TYPE: PRT
<213> ORGANISM: Artificial Sequence
<220> FEATURE:
<223> OTHER INFORMATION: Synthetic construct

<400> SEQUENCE: 167

Val Glu Phe Gly Ala Pro His Ala Val Lys Met Asp Val Tyr Asn Leu
1               5                   10                  15

Gly Asp Gln Thr Gly Val Leu Leu Lys Ala Leu Ala
            20                  25

<210> SEQ ID NO 168
<211> LENGTH: 28

<212> TYPE: PRT
<213> ORGANISM: Artificial Sequence
<220> FEATURE:
<223> OTHER INFORMATION: Synthetic construct

<400> SEQUENCE: 168

Val Glu Phe Glu Glu Pro His Ala Thr Lys Gln Ser Val Val Ala Leu
1               5                   10                  15

Gly Ser Gln Glu Gly Ala Leu His Gln Ala Leu Ala
            20                  25

<210> SEQ ID NO 169
<211> LENGTH: 28
<212> TYPE: PRT
<213> ORGANISM: Artificial Sequence
<220> FEATURE:
<223> OTHER INFORMATION: Synthetic construct

<400> SEQUENCE: 169

Val Glu Phe Gly Val Pro His Ala Val Lys Met Asp Val Tyr Asn Leu
1               5                   10                  15

Gly Asp Gln Thr Gly Val Leu Leu Lys Ser Leu Ala
            20                  25

<210> SEQ ID NO 170
<211> LENGTH: 28
<212> TYPE: PRT
<213> ORGANISM: Artificial Sequence
<220> FEATURE:
<223> OTHER INFORMATION: Synthetic construct

<400> SEQUENCE: 170

Val Glu Phe Glu Glu Ala His Val Thr Arg Gln Thr Val Val Ala Leu
1               5                   10                  15

Ala Ala Gln Glu Gly Glu Leu His Ile Val Leu Ala
            20                  25

<210> SEQ ID NO 171
<211> LENGTH: 28
<212> TYPE: PRT
<213> ORGANISM: Artificial Sequence
<220> FEATURE:
<223> OTHER INFORMATION: Synthetic construct

<400> SEQUENCE: 171

Val Glu Phe Gly Ala Pro His Ala Val Lys Met Asp Val Tyr Asn Leu
1               5                   10                  15

Gly Asp Gln Thr Gly Val Leu Leu Lys Ala Leu Ala
            20                  25

<210> SEQ ID NO 172
<211> LENGTH: 28
<212> TYPE: PRT
<213> ORGANISM: Artificial Sequence
<220> FEATURE:
<223> OTHER INFORMATION: Synthetic construct

<400> SEQUENCE: 172

Val Glu Phe Gly Ala Pro His Ala Val Lys Met Asp Val Tyr Asn Leu
1               5                   10                  15

Gly Asp Gln Thr Gly Val Leu Leu Lys Ser Leu Ala
            20                  25

<210> SEQ ID NO 173

```
<211> LENGTH: 28
<212> TYPE: PRT
<213> ORGANISM: Artificial Sequence
<220> FEATURE:
<223> OTHER INFORMATION: Synthetic construct

<400> SEQUENCE: 173

Val Glu Phe Gly Ala Pro His Ala Val Lys Met Asp Val Tyr Asn Leu
1               5                   10                  15

Gly Asp Gln Thr Gly Val Leu Leu Lys Ala Leu Ala
            20                  25

<210> SEQ ID NO 174
<211> LENGTH: 28
<212> TYPE: PRT
<213> ORGANISM: Artificial Sequence
<220> FEATURE:
<223> OTHER INFORMATION: Synthetic construct

<400> SEQUENCE: 174

Val Glu Phe Gly Pro Pro His Ala Val Lys Met Asp Val Phe Asn Leu
1               5                   10                  15

Gly Asp Gln Thr Ala Val Leu Leu Lys Ser Leu Ala
            20                  25

<210> SEQ ID NO 175
<211> LENGTH: 28
<212> TYPE: PRT
<213> ORGANISM: Artificial Sequence
<220> FEATURE:
<223> OTHER INFORMATION: Synthetic construct

<400> SEQUENCE: 175

Leu Glu Phe Glu Glu Pro His Ala Thr Lys Gln Ser Val Val Ala Leu
1               5                   10                  15

Gly Ser Gln Glu Gly Ala Leu His Gln Ala Leu Ala
            20                  25

<210> SEQ ID NO 176
<211> LENGTH: 28
<212> TYPE: PRT
<213> ORGANISM: Artificial Sequence
<220> FEATURE:
<223> OTHER INFORMATION: Synthetic construct

<400> SEQUENCE: 176

Val Asp Phe Glu Glu Pro His Ala Val Thr Met Lys Ala Leu Val Leu
1               5                   10                  15

Gly Ser Gln Glu Gly Ala Leu Arg Thr Ala Leu Ser
            20                  25

<210> SEQ ID NO 177
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: any amino acid (e.g., R, K, D, E, G, N, Q, S,
      or T, such as K, E, G, Q, or T)
<220> FEATURE:
<221> NAME/KEY: MISC_FEATURE
<222> LOCATION: (3)..(3)
<223> OTHER INFORMATION: any amino acid (e.g., S, T, N, Q, D, E, G, P,
      R, H, K, I, L, V, or A, such as T, N, D, E, P, K, V, or A)
```

```
<220> FEATURE:
<221> NAME/KEY: MISC_FEATURE
<222> LOCATION: (4)..(4)
<223> OTHER INFORMATION: any amino acid (e.g., A, V, I, L, G, S, P, or
      T, such as A, P, or T)
<220> FEATURE:
<221> NAME/KEY: MISC_FEATURE
<222> LOCATION: (6)..(6)
<223> OTHER INFORMATION: any amino acid (e.g., A, V, I, L, or G, such as
      A or V)
<220> FEATURE:
<221> NAME/KEY: MISC_FEATURE
<222> LOCATION: (7)..(7)
<223> OTHER INFORMATION: any amino acid (e.g., R, K, S, T, A, V, I, or
      L, such as K, T, A, or V)
<220> FEATURE:
<221> NAME/KEY: MISC_FEATURE
<222> LOCATION: (8)..(8)
<223> OTHER INFORMATION: any amino acid (e.g., K, R, H, S, or T, such as
      K, R, or T)
<220> FEATURE:
<221> NAME/KEY: MISC_FEATURE
<222> LOCATION: (9)..(9)
<223> OTHER INFORMATION: any amino acid (e.g., N, Q, A, I, L, M, V, K,
      or R, such as Q, I, M, V, or R)
<220> FEATURE:
<221> NAME/KEY: MISC_FEATURE
<222> LOCATION: (10)..(10)
<223> OTHER INFORMATION: any amino acid (e.g., E, D, S, T, R, H, or K,
      such as E, D, S, T, R, or K)

<400> SEQUENCE: 177

Phe Xaa Xaa Xaa His Xaa Xaa Xaa Xaa Xaa
1               5                   10

<210> SEQ ID NO 178
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: any amino acid (e.g., G, A, V, I, or L, such as
      G or A)
<220> FEATURE:
<221> NAME/KEY: MISC_FEATURE
<222> LOCATION: (3)..(3)
<223> OTHER INFORMATION: any amino acid (e.g., S, T, D, E, N, Q, P, G,
      V, I, L, or A, such as S, D, N, P, or A)
<220> FEATURE:
<221> NAME/KEY: MISC_FEATURE
<222> LOCATION: (5)..(5)
<223> OTHER INFORMATION: any amino acid (e.g., E, D, S, or T, such as E
      or T)
<220> FEATURE:
<221> NAME/KEY: MISC_FEATURE
<222> LOCATION: (6)..(6)
<223> OTHER INFORMATION: any amino acid (e.g., G, A, V, I, or L, such as
      G or A)

<400> SEQUENCE: 178

Leu Xaa Xaa Gln Xaa Xaa
1               5

<210> SEQ ID NO 179
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
```

<223> OTHER INFORMATION: any amino acid (e.g., D, E, V, I, L, or A, such as D, E, or A)
<220> FEATURE:
<221> NAME/KEY: MISC_FEATURE
<222> LOCATION: (3)..(3)
<223> OTHER INFORMATION: any amino acid (e.g., S or T)
<220> FEATURE:
<221> NAME/KEY: MISC_FEATURE
<222> LOCATION: (7)..(7)
<223> OTHER INFORMATION: any amino acid (e.g., S, T, A, V, I, or L, such as T or I)
<220> FEATURE:
<221> NAME/KEY: MISC_FEATURE
<222> LOCATION: (8)..(8)
<223> OTHER INFORMATION: any amino acid (e.g., N, Q, A, V, I, or L, such as Q or L)
<220> FEATURE:
<221> NAME/KEY: MISC_FEATURE
<222> LOCATION: (11)..(11)
<223> OTHER INFORMATION: any amino acid (e.g., A, V, I, L, G, or P, such as A or P)
<220> FEATURE:
<221> NAME/KEY: MISC_FEATURE
<222> LOCATION: (12)..(12)
<223> OTHER INFORMATION: any amino acid (e.g., T, S, A, L, I, V, F, or Y, such as T, S, I, V, or Y)
<220> FEATURE:
<221> NAME/KEY: MISC_FEATURE
<222> LOCATION: (14)..(14)
<223> OTHER INFORMATION: any amino acid (e.g., A, V, I, L, N, Q, G, P, R, or K, such as V, N, P, or K)
<220> FEATURE:
<221> NAME/KEY: MISC_FEATURE
<222> LOCATION: (19)..(19)
<223> OTHER INFORMATION: any amino acid (e.g., A, V, I, L, S, T, K, R, N, or Q, such as A, T, K, or Q)
<220> FEATURE:
<221> NAME/KEY: MISC_FEATURE
<222> LOCATION: (20)..(20)
<223> OTHER INFORMATION: any amino acid (e.g., N, R, K, H, or Q, such as N, R, or Q)
<220> FEATURE:
<221> NAME/KEY: MISC_FEATURE
<222> LOCATION: (21)..(21)
<223> OTHER INFORMATION: any amino acid (e.g., F, M, V, I, L, or Y, such as F, L, or Y)
<220> FEATURE:
<221> NAME/KEY: MISC_FEATURE
<222> LOCATION: (22)..(22)
<223> OTHER INFORMATION: any amino acid (e.g., A, V, I, or L, such as V or L)
<220> FEATURE:
<221> NAME/KEY: MISC_FEATURE
<222> LOCATION: (24)..(24)
<223> OTHER INFORMATION: any amino acid (e.g., R, H, or K, such as R or K)
<220> FEATURE:
<221> NAME/KEY: MISC_FEATURE
<222> LOCATION: (25)..(25)
<223> OTHER INFORMATION: any amino acid (e.g., R, K, or H, such as R or H)
<220> FEATURE:
<221> NAME/KEY: MISC_FEATURE
<222> LOCATION: (26)..(26)
<223> OTHER INFORMATION: any amino acid (e.g., T, S, E, or D, such as T, S, or D)
<220> FEATURE:
<221> NAME/KEY: MISC_FEATURE
<222> LOCATION: (27)..(27)
<223> OTHER INFORMATION: any amino acid (e.g., F, M, I, L, Y, or V, such as F, M, Y, or V)

<400> SEQUENCE: 179

```
Thr Xaa Xaa Arg Cys Pro Xaa Xaa Gly Glu Xaa Xaa Leu Xaa Glu Glu
1               5                   10                  15

Gln Asp Xaa Xaa Xaa Xaa Cys Xaa Xaa Xaa Xaa Val Asp Arg Gly
            20                  25                  30
```

```
<210> SEQ ID NO 180
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: any amino acid (e.g., S, T, N, Q, I, L, A, or
      V, such as T, N, or V)
<220> FEATURE:
<221> NAME/KEY: MISC_FEATURE
<222> LOCATION: (6)..(6)
<223> OTHER INFORMATION: any amino acid (e.g., A, V, I, L, G or P, such
      as A or P)
<220> FEATURE:
<221> NAME/KEY: MISC_FEATURE
<222> LOCATION: (10)..(10)
<223> OTHER INFORMATION: any amino acid (e.g., K, R, or H, such as K or
      R)
<220> FEATURE:
<221> NAME/KEY: MISC_FEATURE
<222> LOCATION: (12)..(12)
<223> OTHER INFORMATION: any amino acid (e.g., E or D)
<220> FEATURE:
<221> NAME/KEY: MISC_FEATURE
<222> LOCATION: (14)..(14)
<223> OTHER INFORMATION: any amino acid (e.g., A, V, I, L, S, or T, such
      as V or T)
<220> FEATURE:
<221> NAME/KEY: MISC_FEATURE
<222> LOCATION: (24)..(24)
<223> OTHER INFORMATION: any amino acid (e.g., R, H, K, N, or Q, such as
      H or Q)
<220> FEATURE:
<221> NAME/KEY: MISC_FEATURE
<222> LOCATION: (25)..(25)
<223> OTHER INFORMATION: any amino acid (e.g., S or T)
<220> FEATURE:
<221> NAME/KEY: MISC_FEATURE
<222> LOCATION: (28)..(28)
<223> OTHER INFORMATION: any amino acid (e.g., S, T, V, I, L, or A, such
      as T or A)

<400> SEQUENCE: 180

Val Thr Phe Lys Xaa Xaa His Ala Lys Xaa Gln Xaa Val Xaa Val Leu
1               5                   10                  15

Gly Ser Gln Glu Gly Ala Met Xaa Xaa Ala Leu Xaa
            20                  25

<210> SEQ ID NO 181
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: any amino acid (e.g., R, H, or K, such as R or
      K)
<220> FEATURE:
<221> NAME/KEY: MISC_FEATURE
<222> LOCATION: (3)..(3)
<223> OTHER INFORMATION: any amino acid (e.g., R, K, or H, such as R or
      H)
<220> FEATURE:
<221> NAME/KEY: MISC_FEATURE
<222> LOCATION: (4)..(4)
<223> OTHER INFORMATION: any amino acid (e.g., T, S, E, or D, such as T,
      S, or D)
<220> FEATURE:
<221> NAME/KEY: MISC_FEATURE
```

```
<222> LOCATION: (5)..(5)
<223> OTHER INFORMATION: any amino acid (e.g., F, M, I, L, Y, or V, such
      as F, M, Y, or V)

<400> SEQUENCE: 181

Cys Xaa Xaa Xaa Xaa Val Asp Arg Gly
1               5

<210> SEQ ID NO 182
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: any amino acid (e.g., D, E, V, I, L, or A, such
      as D, E, or A)
<220> FEATURE:
<221> NAME/KEY: MISC_FEATURE
<222> LOCATION: (3)..(3)
<223> OTHER INFORMATION: any amino acid (e.g., S or T)

<400> SEQUENCE: 182

Thr Xaa Xaa Arg Cys Pro
1               5

<210> SEQ ID NO 183
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: any amino acid (e.g., S, T, N, Q, I, L, A, or
      V, such as T, N, or V)
<220> FEATURE:
<221> NAME/KEY: MISC_FEATURE
<222> LOCATION: (6)..(6)
<223> OTHER INFORMATION: any amino acid (e.g., A, V, I, L, G or P, such
      as A or P)
<220> FEATURE:
<221> NAME/KEY: MISC_FEATURE
<222> LOCATION: (10)..(10)
<223> OTHER INFORMATION: any amino acid (e.g., K, R, or H, such as K or
      R)
<220> FEATURE:
<221> NAME/KEY: MISC_FEATURE
<222> LOCATION: (12)..(12)
<223> OTHER INFORMATION: any amino acid (e.g., E or D)

<400> SEQUENCE: 183

Val Thr Phe Lys Xaa Xaa His Ala Lys Xaa Gln Xaa
1               5                   10

<210> SEQ ID NO 184
<211> LENGTH: 6
<212> TYPE: PRT
<213> ORGANISM: Artificial Sequence
<220> FEATURE:
<223> OTHER INFORMATION: Synthetic construct

<400> SEQUENCE: 184

Leu Gly Ser Gln Glu Gly
1               5

<210> SEQ ID NO 185
<211> LENGTH: 31
```

```
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: any amino acid (e.g., T, S, A, V, L, or I, such
      as T, S, V, or I)
<220> FEATURE:
<221> NAME/KEY: MISC_FEATURE
<222> LOCATION: (2)..(2)
<223> OTHER INFORMATION: any amino acid (e.g., D, E, A, I, L, R, H, K,
      V, T, or S, such as D, E, A, R, K, V, or S)
<220> FEATURE:
<221> NAME/KEY: MISC_FEATURE
<222> LOCATION: (3)..(3)
<223> OTHER INFORMATION: any amino acid (e.g., S, T, A, V, I, or L, such
      as S, T, or A)
<220> FEATURE:
<221> NAME/KEY: MISC_FEATURE
<222> LOCATION: (4)..(4)
<223> OTHER INFORMATION: any amino acid (e.g., A, V, I, L, R, K, N, or
      Q, such as R, A, or N)
<220> FEATURE:
<221> NAME/KEY: MISC_FEATURE
<222> LOCATION: (7)..(7)
<223> OTHER INFORMATION: any amino acid (e.g., A, V, I, L, S, or T, such
      as T, I, or A)
<220> FEATURE:
<221> NAME/KEY: MISC_FEATURE
<222> LOCATION: (8)..(8)
<223> OTHER INFORMATION: any amino acid (e.g., N, Q, A, V, I, L, M, S,
      or T, such as Q, V, L, M, or T)
<220> FEATURE:
<221> NAME/KEY: MISC_FEATURE
<222> LOCATION: (9)..(9)
<223> OTHER INFORMATION: any amino acid (e.g., G, N, or Q, such as G or
      Q)
<220> FEATURE:
<221> NAME/KEY: MISC_FEATURE
<222> LOCATION: (10)..(10)
<223> OTHER INFORMATION: any amino acid (e.g., D, E, P, G, A, V, I, or
      L, such as E, P, or L)
<220> FEATURE:
<221> NAME/KEY: MISC_FEATURE
<222> LOCATION: (11)..(11)
<223> OTHER INFORMATION: any amino acid (e.g., A, V, I, L, P, G, T, or
      S, such as A, P, T, or S)
<220> FEATURE:
<221> NAME/KEY: MISC_FEATURE
<222> LOCATION: (12)..(12)
<223> OTHER INFORMATION: any amino acid (e.g., T, S, I, V, L, Y, F, H,
      D, E, or A, such as T, S, I, V, Y, H, E, or A)
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: any amino acid (e.g., V, A, I, L, N, Q, P, R,
      K, E, D, T, or S, such as V, A, N, P, K, E, D, T, or S)
<220> FEATURE:
<221> NAME/KEY: MISC_FEATURE
<222> LOCATION: (15)..(15)
<223> OTHER INFORMATION: any amino acid (e.g., D, E, R, or K, such as E
      or K)
<220> FEATURE:
<221> NAME/KEY: MISC_FEATURE
<222> LOCATION: (16)..(16)
<223> OTHER INFORMATION: any amino acid (e.g., E, R, Q, A, or S)
<220> FEATURE:
<221> NAME/KEY: MISC_FEATURE
<222> LOCATION: (17)..(17)
<223> OTHER INFORMATION: any amino acid (e.g., N, Q, A, V, I, L, S, T,
      H, K, or R, such as Q, A, L, S, T, H, or R)
<220> FEATURE:
<221> NAME/KEY: MISC_FEATURE
```

```
<222> LOCATION: (18)..(18)
<223> OTHER INFORMATION: any amino acid (e.g., D, Q, N, or E, such as D,
      Q, or E)
<220> FEATURE:
<221> NAME/KEY: MISC_FEATURE
<222> LOCATION: (19)..(19)
<223> OTHER INFORMATION: any amino acid (e.g., A, V, I, L, S, T, K, R,
      Q, P, H, G, E, or D, such as A, I, S, T, K, Q, P, H, G, or D)
<220> FEATURE:
<221> NAME/KEY: MISC_FEATURE
<222> LOCATION: (20)..(20)
<223> OTHER INFORMATION: any amino acid (e.g., N, Q, K, R, A, V, I, L,
      S, T, or G, such as N, Q, R, A, S, T, or G)
<220> FEATURE:
<221> NAME/KEY: MISC_FEATURE
<222> LOCATION: (21)..(21)
<223> OTHER INFORMATION: any amino acid (e.g., F, A, V, I, L, Y, S, T,
      or M, such as F, L, Y, T, or M)
<220> FEATURE:
<221> NAME/KEY: MISC_FEATURE
<222> LOCATION: (22)..(22)
<223> OTHER INFORMATION: any amino acid (e.g., A, V, I, or L, such as V,
      I, or L)
<220> FEATURE:
<221> NAME/KEY: MISC_FEATURE
<222> LOCATION: (24)..(24)
<223> OTHER INFORMATION: any amino acid (e.g., R or K)
<220> FEATURE:
<221> NAME/KEY: MISC_FEATURE
<222> LOCATION: (25)..(25)
<223> OTHER INFORMATION: any amino acid (e.g., R, K, S, T, H, N, or Q,
      such as R, K, S, H, or Q)
<220> FEATURE:
<221> NAME/KEY: MISC_FEATURE
<222> LOCATION: (26)..(26)
<223> OTHER INFORMATION: any amino acid (e.g., S, T, G, E, or D, such as
      S, T, G, or D)
<220> FEATURE:
<221> NAME/KEY: MISC_FEATURE
<222> LOCATION: (27)..(27)
<223> OTHER INFORMATION: any amino acid (e.g., F, A, V, I, L, M, Y, N,
      or Q, such as F, V, L, M, Y, or Q)
<220> FEATURE:
<221> NAME/KEY: MISC_FEATURE
<222> LOCATION: (28)..(28)
<223> OTHER INFORMATION: any amino acid (e.g., A, V, I, L, T, or S, such
      as V, T, or S)
<220> FEATURE:
<221> NAME/KEY: MISC_FEATURE
<222> LOCATION: (29)..(29)
<223> OTHER INFORMATION: any amino acid (e.g., E, D, Q, or N, such as D
      or N)

<400> SEQUENCE: 185

Xaa Xaa Xaa Xaa Cys Pro Xaa Xaa Xaa Xaa Xaa Xaa Xaa Xaa Xaa
1               5                   10                  15

Xaa Xaa Xaa Xaa Xaa Xaa Cys Xaa Xaa Xaa Xaa Xaa Arg Gly
            20                  25                  30

<210> SEQ ID NO 186
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: any amino acid (e.g., A, V, I, L, N, or Q, such
      as V, I, L, or N)
<220> FEATURE:
<221> NAME/KEY: MISC_FEATURE
<222> LOCATION: (2)..(2)
<223> OTHER INFORMATION: any amino acid (e.g., S, T, D, or E, such as T
      or E)
<220> FEATURE:
```

-continued

```
<221> NAME/KEY: MISC_FEATURE
<222> LOCATION: (4)..(4)
<223> OTHER INFORMATION: any amino acid (e.g., K, R, E, D, G, N, or Q ,
      such as K, E, G, or Q)
<220> FEATURE:
<221> NAME/KEY: MISC_FEATURE
<222> LOCATION: (5)..(5)
<223> OTHER INFORMATION: any amino acid (e.g., S, T, N, Q, D, E, A, V,
      I, L, K, R, P or G, such as T, N, D, E, A, V, K, or P)
<220> FEATURE:
<221> NAME/KEY: MISC_FEATURE
<222> LOCATION: (6)..(6)
<223> OTHER INFORMATION: any amino acid (e.g., A, V, I, L, P, G, S, or
      T, such as A, P, or T)
<220> FEATURE:
<221> NAME/KEY: MISC_FEATURE
<222> LOCATION: (8)..(8)
<223> OTHER INFORMATION: any amino acid (e.g., A, V, I, or L, such as A
      or V)
<220> FEATURE:
<221> NAME/KEY: MISC_FEATURE
<222> LOCATION: (9)..(9)
<223> OTHER INFORMATION: any amino acid (e.g., K, R, S, T, A, V, I, or
      L, such as K, T, or V)
<220> FEATURE:
<221> NAME/KEY: MISC_FEATURE
<222> LOCATION: (10)..(10)
<223> OTHER INFORMATION: any amino acid (e.g., K, R or H)
<220> FEATURE:
<221> NAME/KEY: MISC_FEATURE
<222> LOCATION: (11)..(11)
<223> OTHER INFORMATION: any amino acid (e.g., N, Q, M, S, or T, such as
      Q or M)
<220> FEATURE:
<221> NAME/KEY: MISC_FEATURE
<222> LOCATION: (12)..(12)
<223> OTHER INFORMATION: any amino acid (e.g., E, D, S, or T)
<220> FEATURE:
<221> NAME/KEY: MISC_FEATURE
<222> LOCATION: (13)..(13)
<223> OTHER INFORMATION: any amino acid (e.g., A, V, I, or L, such as V
      or I)
<220> FEATURE:
<221> NAME/KEY: MISC_FEATURE
<222> LOCATION: (14)..(14)
<223> OTHER INFORMATION: any amino acid (e.g., A, V, I, L, S, T, F, or
      Y, such as V, T, I, or F)
<220> FEATURE:
<221> NAME/KEY: MISC_FEATURE
<222> LOCATION: (15)..(15)
<223> OTHER INFORMATION: any amino acid (e.g., A, V, I, L, N or Q, such
      as A, V, or N)
<220> FEATURE:
<221> NAME/KEY: MISC_FEATURE
<222> LOCATION: (17)..(17)
<223> OTHER INFORMATION: any amino acid (e.g., A, V, I, L, or G, such as
      G or A)
<220> FEATURE:
<221> NAME/KEY: MISC_FEATURE
<222> LOCATION: (18)..(18)
<223> OTHER INFORMATION: any amino acid (e.g., A, V, I, L, S, T, E, D,
      N, Q, or G, such as S, D, N, or A)
<220> FEATURE:
<221> NAME/KEY: MISC_FEATURE
<222> LOCATION: (20)..(20)
<223> OTHER INFORMATION: any amino acid (e.g., D, E, S, or T, such as E
      or T)
<220> FEATURE:
<221> NAME/KEY: MISC_FEATURE
<222> LOCATION: (21)..(21)
<223> OTHER INFORMATION: any amino acid (e.g., A, V, I, L, or G, such as
      G or A)
<220> FEATURE:
<221> NAME/KEY: MISC_FEATURE
<222> LOCATION: (22)..(22)
<223> OTHER INFORMATION: any amino acid (e.g., A, V, I, L, G, E, D, S,
      or T, such as A, I, V, G, T, or E)
<220> FEATURE:
<221> NAME/KEY: MISC_FEATURE
```

```
<222> LOCATION: (23)..(23)
<223> OTHER INFORMATION: any amino acid (e.g., A, V, I, L, or M, such as
      V, L, or M)
<220> FEATURE:
<221> NAME/KEY: MISC_FEATURE
<222> LOCATION: (24)..(24)
<223> OTHER INFORMATION: any amino acid (e.g., A, V, I, L, H, K, R, Q,
      or N, such as H, Q, or L)
<220> FEATURE:
<221> NAME/KEY: MISC_FEATURE
<222> LOCATION: (25)..(25)
<223> OTHER INFORMATION: any amino acid (e.g., A, V, I, L, S, T, N, Q,
      K, or R, such as V, I, L, S, T, Q, K, or R)
<220> FEATURE:
<221> NAME/KEY: MISC_FEATURE
<222> LOCATION: (26)..(26)
<223> OTHER INFORMATION: any amino acid (e.g., A, V, I, L, S, or T, such
      as A, V, or S)
<220> FEATURE:
<221> NAME/KEY: MISC_FEATURE
<222> LOCATION: (28)..(28)
<223> OTHER INFORMATION: any amino acid (e.g., A, V, I, L, S, or T, such
      as A or T)

<400> SEQUENCE: 186

Xaa Xaa Phe Xaa Xaa Xaa His Xaa Xaa Xaa Xaa Xaa Xaa Xaa Xaa Leu
1               5                   10                  15

Xaa Xaa Gln Xaa Xaa Xaa Xaa Xaa Xaa Leu Xaa
            20                  25

<210> SEQ ID NO 187
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: any amino acid (e.g., R or K)
<220> FEATURE:
<221> NAME/KEY: MISC_FEATURE
<222> LOCATION: (3)..(3)
<223> OTHER INFORMATION: any amino acid (e.g., R, K, S, T, H, N, or Q,
      such as R, K, S, H, or Q)
<220> FEATURE:
<221> NAME/KEY: MISC_FEATURE
<222> LOCATION: (4)..(4)
<223> OTHER INFORMATION: any amino acid (e.g., S, T, G, E, or D, such as
      S, T, G, or D)
<220> FEATURE:
<221> NAME/KEY: MISC_FEATURE
<222> LOCATION: (5)..(5)
<223> OTHER INFORMATION: any amino acid (e.g., F, A, V, I, L, M, Y, N,
      or Q, such as  F, V, L, M, Y, or Q)
<220> FEATURE:
<221> NAME/KEY: MISC_FEATURE
<222> LOCATION: (6)..(6)
<223> OTHER INFORMATION: any amino acid (e.g., A, V, I, L, T, or S, such
      as V, T, or S)
<220> FEATURE:
<221> NAME/KEY: MISC_FEATURE
<222> LOCATION: (7)..(7)
<223> OTHER INFORMATION: any amino acid (e.g., E, D, Q, or N, such as D
      or N)

<400> SEQUENCE: 187

Cys Xaa Xaa Xaa Xaa Xaa Xaa Arg Gly
1               5

<210> SEQ ID NO 188
<211> LENGTH: 6
<212> TYPE: PRT
<213> ORGANISM: Artificial Sequence
```

```
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: any amino acid (e.g., T, S, A, V, L, or I, such
      as T, S, V, or I)
<220> FEATURE:
<221> NAME/KEY: MISC_FEATURE
<222> LOCATION: (2)..(2)
<223> OTHER INFORMATION: any amino acid (e.g., D, E, A, I, L, R, H, K,
      V, T, or S, such as D, E, A, R, K, V, or S)
<220> FEATURE:
<221> NAME/KEY: MISC_FEATURE
<222> LOCATION: (3)..(3)
<223> OTHER INFORMATION: any amino acid (e.g., S, T, A, V, I, or L, such
      as S, T, or A)

<400> SEQUENCE: 188

Xaa Xaa Xaa Arg Cys Pro
1               5

<210> SEQ ID NO 189
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: any amino acid (e.g., A, V, I, L, N, or Q, such
      as V, I, L, or N)
<220> FEATURE:
<221> NAME/KEY: MISC_FEATURE
<222> LOCATION: (2)..(2)
<223> OTHER INFORMATION: any amino acid (e.g., S, T, D, or E (e.g., T or
      E))
<220> FEATURE:
<221> NAME/KEY: MISC_FEATURE
<222> LOCATION: (4)..(4)
<223> OTHER INFORMATION: any amino acid (e.g., K, R, E, D, G, N, or Q
      (e.g., K, E, G, or Q))
<220> FEATURE:
<221> NAME/KEY: MISC_FEATURE
<222> LOCATION: (5)..(5)
<223> OTHER INFORMATION: any amino acid (e.g., S, T, N, Q, D, E, A, V,
      I, L, K, R, P or G (e.g., T, N, D, E, A, V, K, or P))
<220> FEATURE:
<221> NAME/KEY: MISC_FEATURE
<222> LOCATION: (6)..(6)
<223> OTHER INFORMATION: any amino acid (e.g., A, V, I, L, P, G, S, or T
      (e.g., A, P, or T))
<220> FEATURE:
<221> NAME/KEY: MISC_FEATURE
<222> LOCATION: (8)..(8)
<223> OTHER INFORMATION: any amino acid (e.g., A, V, I, or L (e.g., A or
      V))
<220> FEATURE:
<221> NAME/KEY: MISC_FEATURE
<222> LOCATION: (9)..(9)
<223> OTHER INFORMATION: any amino acid (e.g., K, R, S, T, A, V, I, or L
      (e.g., K, T, or V))
<220> FEATURE:
<221> NAME/KEY: MISC_FEATURE
<222> LOCATION: (10)..(10)
<223> OTHER INFORMATION: any amino acid (e.g., K, R or H)
<220> FEATURE:
<221> NAME/KEY: MISC_FEATURE
<222> LOCATION: (11)..(11)
<223> OTHER INFORMATION: any amino acid (e.g., N, Q, M, S, or T (e.g., Q
      or M))
<220> FEATURE:
<221> NAME/KEY: MISC_FEATURE
<222> LOCATION: (12)..(12)
<223> OTHER INFORMATION: any amino acid (e.g., E, D, S, or T)
```

<400> SEQUENCE: 189

Xaa Xaa Phe Xaa Xaa Xaa His Xaa Xaa Xaa Xaa Xaa
1               5                   10

<210> SEQ ID NO 190
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: any amino acid (e.g., A, V, I, L, P, G, S, or T
      (e.g., A, P, or T))
<220> FEATURE:
<221> NAME/KEY: MISC_FEATURE
<222> LOCATION: (3)..(3)
<223> OTHER INFORMATION: any amino acid (e.g., A, V, I, or L (e.g., A or
      V))
<220> FEATURE:
<221> NAME/KEY: MISC_FEATURE
<222> LOCATION: (4)..(4)
<223> OTHER INFORMATION: any amino acid (e.g., K, R, S, T, A, V, I, or L
      (e.g., K, T, or V))
<220> FEATURE:
<221> NAME/KEY: MISC_FEATURE
<222> LOCATION: (5)..(5)
<223> OTHER INFORMATION: any amino acid (e.g., K, R or H)

<400> SEQUENCE: 190

Xaa His Xaa Xaa Xaa
1               5

<210> SEQ ID NO 191
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: any amino acid (e.g., A, V, I, L, or G (e.g., G
      or A))
<220> FEATURE:
<221> NAME/KEY: MISC_FEATURE
<222> LOCATION: (3)..(3)
<223> OTHER INFORMATION: any amino acid (e.g., A, V, I, L, S, T, E, D,
      N, Q, or G (e.g., S, D, N, or A))
<220> FEATURE:
<221> NAME/KEY: MISC_FEATURE
<222> LOCATION: (5)..(5)
<223> OTHER INFORMATION: any amino acid (e.g., D, E, S, or T (e.g., E or
      T))
<220> FEATURE:
<221> NAME/KEY: MISC_FEATURE
<222> LOCATION: (6)..(6)
<223> OTHER INFORMATION: any amino acid (e.g., A, V, I, L, or G (e.g., G
      or A))

<400> SEQUENCE: 191

Leu Xaa Xaa Gln Xaa Xaa
1               5

<210> SEQ ID NO 192
<211> LENGTH: 495
<212> TYPE: PRT
<213> ORGANISM: Dengue virus

<400> SEQUENCE: 192

Met Arg Cys Ile Gly Ile Ser Asn Arg Asp Phe Val Glu Gly Val Ser

-continued

```
1               5                   10                  15
Gly Gly Ser Trp Val Asp Ile Val Leu Glu His Gly Ser Cys Val Thr
                20                  25                  30
Thr Met Ala Lys Asn Lys Pro Thr Leu Asp Phe Glu Leu Ile Glu Thr
                35                  40                  45
Glu Ala Lys Gln Pro Ala Thr Leu Arg Lys Tyr Cys Ile Glu Ala Lys
                50                  55                  60
Leu Thr Asn Thr Thr Thr Asp Ser Arg Cys Pro Thr Gln Gly Glu Pro
65                  70                  75                  80
Ser Leu Asn Glu Glu Gln Asp Lys Arg Phe Val Cys Lys His Ser Met
                85                  90                  95
Val Asp Arg Gly Trp Gly Asn Gly Cys Gly Leu Phe Gly Lys Gly Gly
                100                 105                 110
Ile Val Thr Cys Ala Met Phe Thr Cys Lys Lys Asn Met Lys Gly Lys
                115                 120                 125
Val Val Gln Pro Glu Asn Leu Glu Tyr Thr Ile Val Ile Thr Pro His
                130                 135                 140
Ser Gly Glu Glu His Ala Val Gly Asn Asp Thr Gly Lys His Gly Lys
145                 150                 155                 160
Glu Ile Lys Ile Thr Pro Gln Ser Ser Ile Thr Glu Ala Glu Leu Thr
                165                 170                 175
Gly Tyr Gly Thr Val Thr Met Glu Cys Ser Pro Arg Thr Gly Leu Asp
                180                 185                 190
Phe Asn Glu Met Val Leu Leu Gln Met Glu Asn Lys Ala Trp Leu Val
                195                 200                 205
His Arg Gln Trp Phe Leu Asp Leu Pro Leu Pro Trp Leu Pro Gly Ala
                210                 215                 220
Asp Thr Gln Gly Ser Asn Trp Ile Gln Lys Glu Thr Leu Val Thr Phe
225                 230                 235                 240
Lys Asn Pro His Ala Lys Lys Gln Asp Val Val Val Leu Gly Ser Gln
                245                 250                 255
Glu Gly Ala Met His Thr Ala Leu Thr Gly Ala Thr Glu Ile Gln Met
                260                 265                 270
Ser Ser Gly Asn Leu Leu Phe Thr Gly His Leu Lys Cys Arg Leu Arg
                275                 280                 285
Met Asp Lys Leu Gln Leu Lys Gly Met Ser Tyr Ser Met Cys Thr Gly
                290                 295                 300
Lys Phe Lys Val Val Lys Glu Ile Ala Glu Thr Gln His Gly Thr Ile
305                 310                 315                 320
Val Ile Arg Val Gln Tyr Glu Gly Asp Gly Ser Pro Cys Lys Ile Pro
                325                 330                 335
Phe Glu Ile Met Asp Leu Glu Lys Arg His Val Leu Gly Arg Leu Ile
                340                 345                 350
Thr Val Asn Pro Ile Val Thr Glu Lys Asp Ser Pro Val Asn Ile Glu
                355                 360                 365
Ala Glu Pro Pro Phe Gly Asp Ser Tyr Ile Ile Ile Gly Val Glu Pro
                370                 375                 380
Gly Gln Leu Lys Leu Asn Trp Phe Lys Lys Gly Ser Ser Ile Gly Gln
385                 390                 395                 400
Met Ile Glu Thr Thr Met Arg Gly Ala Lys Arg Met Ala Ile Leu Gly
                405                 410                 415
Asp Thr Ala Trp Asp Phe Gly Ser Leu Gly Gly Val Phe Thr Ser Ile
                420                 425                 430
```

```
Gly Lys Ala Leu His Gln Val Phe Gly Ala Ile Tyr Gly Ala Phe
        435                 440                 445

Ser Gly Val Ser Trp Ile Met Lys Ile Leu Ile Gly Val Ile Thr
    450                 455                 460

Trp Ile Gly Met Asn Ser Arg Ser Thr Ser Leu Ser Val Ser Leu Val
465                 470                 475                 480

Leu Val Gly Val Val Thr Leu Tyr Leu Gly Val Met Val Gln Ala
                485                 490                 495

<210> SEQ ID NO 193
<211> LENGTH: 20
<212> TYPE: PRT
<213> ORGANISM: Artificial Sequence
<220> FEATURE:
<223> OTHER INFORMATION: Synthetic construct

<400> SEQUENCE: 193

Phe Trp Phe Thr Leu Ile Lys Thr Gln Ala Lys Gln Pro Ala Arg Tyr
1               5                   10                  15

Arg Arg Phe Cys
            20

<210> SEQ ID NO 194
<211> LENGTH: 33
<212> TYPE: PRT
<213> ORGANISM: Artificial Sequence
<220> FEATURE:
<223> OTHER INFORMATION: Synthetic construct

<400> SEQUENCE: 194

Met Ala Ile Leu Gly Asp Thr Ala Trp Asp Phe Gly Ser Leu Gly Gly
1               5                   10                  15

Val Phe Thr Ser Ile Gly Lys Ala Leu His Gln Val Phe Gly Ala Ile
                20                  25                  30

Tyr

<210> SEQ ID NO 195
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(7)
<223> OTHER INFORMATION: alpha-keto linkage
<220> FEATURE:
<221> NAME/KEY: MOD_RES
<222> LOCATION: (8)..(8)
<223> OTHER INFORMATION: AMIDATION

<400> SEQUENCE: 195

Phe Ala Ala Gly Arg Arg Ser Leu
1               5

<210> SEQ ID NO 196
<211> LENGTH: 6
<212> TYPE: PRT
<213> ORGANISM: Artificial Sequence
<220> FEATURE:
<223> OTHER INFORMATION: Synthetic construct
```

-continued

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: FORMYLATION

<400> SEQUENCE: 196

Phe Ala Ala Gly Arg Arg
1               5

<210> SEQ ID NO 197
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(8)
<223> OTHER INFORMATION: cyclic peptide

<400> SEQUENCE: 197

Gly Lys Arg Lys Ser Gly Cys Ala
1               5

<210> SEQ ID NO 198
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(7)
<223> OTHER INFORMATION: cyclic peptide

<400> SEQUENCE: 198

Cys Gly Lys Arg Lys Ser Cys
1               5

<210> SEQ ID NO 199
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: D amino acid
<220> FEATURE:
<221> NAME/KEY: MISC_FEATURE
<222> LOCATION: (6)..(6)
<223> OTHER INFORMATION: homoF
<220> FEATURE:
<221> NAME/KEY: MISC_FEATURE
<222> LOCATION: (7)..(7)
<223> OTHER INFORMATION: 1Nal
<220> FEATURE:
<221> NAME/KEY: MISC_FEATURE
<222> LOCATION: (8)..(8)
<223> OTHER INFORMATION: D amino acid

<400> SEQUENCE: 199

Arg Arg Arg Lys Ala Xaa Xaa Phe
1               5

<210> SEQ ID NO 200
```

```
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bz-Nle
<220> FEATURE:
<221> NAME/KEY: MOD_RES
<222> LOCATION: (1)..(1)
<223> OTHER INFORMATION: B(OH)2 modification

<400> SEQUENCE: 200

Xaa Lys Arg
1

<210> SEQ ID NO 201
<211> LENGTH: 29
<212> TYPE: PRT
<213> ORGANISM: Artificial Sequence
<220> FEATURE:
<223> OTHER INFORMATION: Synthetic construct

<400> SEQUENCE: 201

Ala Trp Asp Phe Gly Ser Leu Gly Gly Val Phe Thr Ser Ile Gly Lys
1               5                   10                  15

Ala Leu His Gln Val Phe Gly Ala Ile Tyr Gly Ala Ala
            20                  25

<210> SEQ ID NO 202
<211> LENGTH: 29
<212> TYPE: PRT
<213> ORGANISM: Artificial Sequence
<220> FEATURE:
<223> OTHER INFORMATION: Synthetic construct

<400> SEQUENCE: 202

Ala Trp Asp Phe Gly Ser Leu Gly Gly Val Phe Thr Ser Ile Gly Lys
1               5                   10                  15

Ala Leu His Gln Val Phe Gly Trp Trp Trp Gly Ala Ala
            20                  25

<210> SEQ ID NO 203
<211> LENGTH: 41
<212> TYPE: PRT
<213> ORGANISM: Artificial Sequence
<220> FEATURE:
<223> OTHER INFORMATION: Synthetic construct

<400> SEQUENCE: 203

Ser Val Ala Leu Val Pro His Val Gly Met Gly Leu Glu Thr Arg Thr
1               5                   10                  15

Glu Thr Trp Met Ser Ser Glu Gly Ala Trp Lys His Val Gln Arg Ile
            20                  25                  30

Glu Thr Trp Ile Leu Arg His Pro Gly
        35                  40

<210> SEQ ID NO 204
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 204

Arg Thr Ser Lys Lys Arg
1               5

<210> SEQ ID NO 205
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (4)..(4)
<223> OTHER INFORMATION: AMIDATION

<400> SEQUENCE: 205

Trp Tyr Cys Trp
1

<210> SEQ ID NO 206
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Bz- modification
<220> FEATURE:
<221> NAME/KEY: MOD_RES
<222> LOCATION: (4)..(4)
<223> OTHER INFORMATION: -H modification

<400> SEQUENCE: 206

Ala Lys Arg Arg
1

<210> SEQ ID NO 207
<211> LENGTH: 3
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Bz-nK
<220> FEATURE:
<221> NAME/KEY: MISC_FEATURE
<222> LOCATION: (3)..(3)
<223> OTHER INFORMATION: B(OH)2 modification

<400> SEQUENCE: 207

Xaa Arg Arg
1
```